United States Patent
Xu et al.

(10) Patent No.: US 12,091,554 B2
(45) Date of Patent: Sep. 17, 2024

(54) SUBSTITUTED POLYFLUORENE COMPOUNDS

(71) Applicant: BIOLEGEND, INC., San Diego, CA (US)

(72) Inventors: Xinshe Xu, San Diego, CA (US); Jing Wang, San Diego, CA (US)

(73) Assignee: Biolegend, Inc., San Diego, CA (US)

( * ) Notice: Subject to any disclaimer, the term of this patent is extended or adjusted under 35 U.S.C. 154(b) by 178 days.

(21) Appl. No.: 17/469,792

(22) Filed: Sep. 8, 2021

(65) Prior Publication Data

US 2022/0002552 A1    Jan. 6, 2022

Related U.S. Application Data

(63) Continuation of application No. 16/240,024, filed on Jan. 4, 2019, now Pat. No. 11,155,714, which is a continuation of application No. PCT/US2017/041187, filed on Jul. 7, 2017.

(60) Provisional application No. 62/360,155, filed on Jul. 8, 2016.

(51) Int. Cl.
| | |
|---|---|
| *C09B 69/10* | (2006.01) |
| *C07C 25/22* | (2006.01) |
| *C07C 35/50* | (2006.01) |
| *C07C 211/60* | (2006.01) |
| *C07C 237/04* | (2006.01) |
| *C07D 211/18* | (2006.01) |
| *C07D 235/02* | (2006.01) |
| *C07D 311/96* | (2006.01) |
| *C08G 81/00* | (2006.01) |
| *C09B 57/00* | (2006.01) |
| *G01N 21/64* | (2006.01) |

(52) U.S. Cl.
CPC ............ *C09B 69/109* (2013.01); *C07C 25/22* (2013.01); *C07C 35/50* (2013.01); *C07C 211/60* (2013.01); *C07C 237/04* (2013.01); *C07D 211/18* (2013.01); *C07D 235/02* (2013.01); *C07D 311/96* (2013.01); *C08G 81/00* (2013.01); *C09B 57/00* (2013.01); *C09B 69/10* (2013.01); *G01N 21/6428* (2013.01); *G01N 2021/6439* (2013.01)

(58) Field of Classification Search
CPC ....... C07C 211/60; C07C 25/22; C07C 35/50; C07C 237/04; C07D 235/02; C07D 311/96; C07D 211/18; C09B 69/109; C09B 69/10; C09B 57/00; G01N 21/6428; G01N 2021/6439; C08G 81/00
See application file for complete search history.

(56) References Cited

U.S. PATENT DOCUMENTS

| | | | |
|---|---|---|---|
| 4,436,745 A | 3/1984 | York, Jr. | |
| 6,387,893 B1 | 5/2002 | Evans et al. | |
| 6,512,083 B1 * | 1/2003 | Woo ............ | C07C 211/48 |
| | | | 427/407.1 |
| 7,144,950 B2 | 12/2006 | Bazan et al. | |
| 7,214,489 B2 | 5/2007 | Bazan et al. | |
| 7,270,956 B2 | 9/2007 | Bazan et al. | |
| 7,629,448 B2 | 12/2009 | Bazan et al. | |
| 7,666,594 B2 | 2/2010 | Bazan et al. | |
| 7,811,755 B2 | 10/2010 | Bazan et al. | |
| 7,897,684 B2 | 3/2011 | Bazan et al. | |
| 7,914,984 B2 | 3/2011 | Bazan et al. | |
| 8,101,416 B2 | 1/2012 | Bazan et al. | |
| 8,110,673 B2 | 2/2012 | Bazan et al. | |
| 8,158,444 B2 | 4/2012 | Gaylord et al. | |
| 8,227,187 B2 | 7/2012 | Bazan et al. | |
| 8,338,532 B2 | 12/2012 | Bazan et al. | |
| 8,354,239 B2 | 1/2013 | Gaylord et al. | |
| 8,362,193 B2 | 1/2013 | Gaylord et al. | |
| 8,455,613 B2 | 6/2013 | Gaylord et al. | |
| 8,546,081 B2 | 10/2013 | Bazan et al. | |
| 8,575,303 B2 | 11/2013 | Gaylord et al. | |
| 8,669,055 B2 | 3/2014 | Bazan et al. | |
| 8,759,444 B2 | 6/2014 | Bazan et al. | |
| 8,802,450 B2 | 8/2014 | Gaylord et al. | |
| 8,835,113 B2 | 9/2014 | Bazan et al. | |
| 8,841,072 B2 | 9/2014 | Bazan et al. | |
| 8,969,509 B2 | 3/2015 | Liu et al. | |
| 9,085,799 B2 | 7/2015 | Bazan et al. | |
| 9,139,869 B2 | 9/2015 | Gaylord et al. | |
| 9,159,465 B2 | 10/2015 | Bazan et al. | |
| 9,371,559 B2 | 6/2016 | Bazan et al. | |
| 9,383,353 B2 | 7/2016 | Gaylord et al. | |

(Continued)

FOREIGN PATENT DOCUMENTS

| | | |
|---|---|---|
| CN | 1637114 A | 7/2005 |
| CN | 1768090 A | 5/2006 |

(Continued)

OTHER PUBLICATIONS

Destri et al., Synthesis and Crystal Structure and Optical Properties of Fluorenic-Core Oligomers, Journal of Materials Chemistry, vol. 12, Jan. 1, 2002, pp. 924-933.

Eisleb, Neue Synthesen Mit Natriumamids, Chemische Berichte, vol. 74, No. 8, Jan. 1, 1941, pp. 1433-1450.

France et al., The Condensation of Fluorene with Acetone. Part III Formation of Fluoranthene Derivatives, Journal of the Chemical Society, Jan. 1, 1945, pp. 7-10.

(Continued)

*Primary Examiner* — Shafiqul Haq
(74) *Attorney, Agent, or Firm* — Kilpatrick Townsend & Stockton LLP

(57) ABSTRACT

The present invention provides fluorescent polyfluorene polymers or macromers with unique optical properties that are stable. The polymeric fluorophores are useful in various bioassays formats. The inventive polymers are useful in assays relying on fluorescence resonance energy transfer (FRET) mechanisms where two fluorophores are used.

12 Claims, 20 Drawing Sheets

(56) References Cited

U.S. PATENT DOCUMENTS

| | | | |
|---|---|---|---|
| 9,412,949 B2 | 8/2016 | Liu | |
| 9,547,008 B2 | 1/2017 | Gaylord et al. | |
| 9,623,123 B2 | 4/2017 | Liu | |
| 9,758,625 B2 | 9/2017 | Bartholomew et al. | |
| RE46,817 E | 5/2018 | Bazan et al. | |
| 10,001,473 B2 | 6/2018 | Bazan et al. | |
| 10,094,838 B2 | 10/2018 | Gaylord et al. | |
| 10,107,818 B2 | 10/2018 | Gaylord et al. | |
| 10,126,302 B2 | 11/2018 | Gaylord et al. | |
| 10,240,004 B2 | 3/2019 | Bartholomew et al. | |
| 10,288,620 B2 | 5/2019 | Gaylord et al. | |
| 10,302,648 B2 | 5/2019 | Gaylord et al. | |
| 10,365,271 B2 | 7/2019 | Bazan et al. | |
| 10,365,285 B2 | 7/2019 | Gaylord et al. | |
| 10,458,989 B2 | 10/2019 | Gaylord et al. | |
| 10,472,521 B2 | 11/2019 | Radford et al. | |
| 10,481,161 B2 | 11/2019 | Gaylord et al. | |
| 10,533,092 B2 | 1/2020 | Bartholomew et al. | |
| RE47,874 E | 2/2020 | Bazan et al. | |
| 10,604,657 B2 | 3/2020 | Bartholomew et al. | |
| 10,605,813 B2 | 3/2020 | Liang et al. | |
| 10,641,777 B2 | 5/2020 | Gaylord et al. | |
| 10,703,864 B2 | 7/2020 | Bartholomew et al. | |
| 11,155,714 B2 * | 10/2021 | Xu | C07D 211/18 |
| 11,584,883 B2 * | 2/2023 | Xu | G01N 33/582 |
| 2005/0123802 A1 | 6/2005 | Park et al. | |
| 2006/0149016 A1 | 7/2006 | O'Dell et al. | |
| 2007/0031698 A1 | 2/2007 | Towns et al. | |
| 2009/0247728 A1 | 10/2009 | Pan et al. | |
| 2012/0068121 A1 | 3/2012 | Sparrowe et al. | |
| 2012/0108731 A1 | 5/2012 | Heun et al. | |
| 2012/0232238 A1 | 9/2012 | Katz et al. | |
| 2013/0109029 A1 | 5/2013 | Liu et al. | |
| 2014/0091300 A1 | 4/2014 | Pan et al. | |
| 2018/0009989 A1 | 1/2018 | Liang et al. | |
| 2018/0364245 A1 | 12/2018 | Martin et al. | |
| 2019/0025295 A1 | 1/2019 | Bazan et al. | |
| 2019/0033317 A1 | 1/2019 | Gaylord et al. | |
| 2019/0194467 A1 | 6/2019 | Liang et al. | |
| 2019/0204328 A1 | 7/2019 | Gaylord et al. | |
| 2019/0346450 A1 | 11/2019 | Gaylord et al. | |
| 2019/0376959 A1 | 12/2019 | Bazan et al. | |
| 2019/0376977 A1 | 12/2019 | Gaylord et al. | |
| 2020/0062966 A1 | 2/2020 | Bartholomew et al. | |
| 2020/0141943 A1 | 5/2020 | Gaylord et al. | |
| 2020/0181412 A1 | 6/2020 | Bartholomew et al. | |
| 2020/0200761 A1 | 6/2020 | Liang et al. | |
| 2020/0239766 A1 | 7/2020 | Xu et al. | |
| 2020/0270400 A1 | 8/2020 | Bartholomew et al. | |
| 2020/0284785 A1 | 9/2020 | Bazan et al. | |
| 2022/0002552 A1 | 1/2022 | Xu et al. | |

FOREIGN PATENT DOCUMENTS

| | | |
|---|---|---|
| CN | 101 495535 A | 7/2009 |
| CN | 101553579 A | 10/2009 |
| CN | 102449022 A | 5/2012 |
| CN | 103563113 A | 2/2014 |
| CN | 106084186 | 11/2016 |
| DE | 102009030847 | 12/2010 |
| EP | 1533289 | 5/2005 |
| EP | 3658648 B1 | 10/2021 |
| GB | 2355457 | 4/2001 |
| TW | 201127867 A | 8/2011 |
| WO | 2008/009343 A1 | 1/2008 |
| WO | 2008100344 | 8/2008 |
| WO | 2010/136112 A1 | 12/2010 |
| WO | 2012/002911 A1 | 1/2012 |
| WO | 2012/163464 A1 | 12/2012 |

OTHER PUBLICATIONS

Jiang et al., Multifunctional Fluorene-Based Oligomers with Novel Spiro-Annulated Triarylamine: Efficient. Stable Deep-Blue Electroluminescence. Good Hole Injection. and Transporting Materials with Very High Tg, Advanced Functional Materials, vol. 19, No. 24, Dec. 23, 2009, pp. 3987-3995.

Marsitzky et al., Poly-2,8-(Indenofluorene-Co-Anthracene)—A Colorfast Blue-Light-Emitting Random Copolymer, Advanced Materials, vol. 13, No. 14, Jul. 2001, pp. 1096-1099.

International Application No. PCT/US2017/041187, International Search Report and Written Opinion mailed on Nov. 20, 2017, 20 pages.

International Application No. PCT/US2018/043911, International Search Report and Written Opinion mailed on Oct. 23, 2018, 17 pages.

Pu et al., Mannose-Substituted Conjugated Polyelectrolyte and Oligomer as an Intelligent Energy Transfer Pair for Label-Free Visual Detection of Concanavalin A, Macromolecules, vol. 43, No. 23, Dec. 14, 2010, pp. 9690-9697.

Wang et al., Broadband Spectra with Fluorescence and Phosphorescence Dual Emission from Bichromophoric Platinum Metallomesogens Containing a 6, 12-Dihydro-Indeno[1,2-b]Fluorene Linkage, RSC Advances, vol. 6, No. 51, 2016, pp. 45864-45872.

Wong, Synthesis, Structures, and Photoinduced Electron Transfer Reaction in the 9,9'-Spirobifluorene-Bridged Bipolar Systems, The Journal of Organic Chemistry, vol. 71, No. 2, 2006, pp. 456-465.

Amara et al., Conjugated Polymers with Geminal Trifluoromethyl Substituents Derived from Hexafluoroacetone, Macromolecules. vol. 39, No. 17, Jul. 28, 2006, pp. 5753-5759.

Ma et al., Indenofluorene Based Water Soluble Conjugated Oligomers for Hg2+ Detection, Sensors and Actuators B: Chemical, vol. 176, Jan. 2013, pp. 132-140.

International Application No. PCT/US2018/043911, International Preliminary Report on Patentability mailed on Feb. 6, 2020, 11 pages.

Setayesh et al., Bridging the Gap between Polyfluorene and Ladder-Poly-p-phenylene: Synthesis and Characterization of Poly-2,8-indenofluorene, Macromolecules. vol. 33, No. 6, Mar. 3, 2000, pp. 2016-2020.

* cited by examiner

FIG. 4A  FIG. 4B

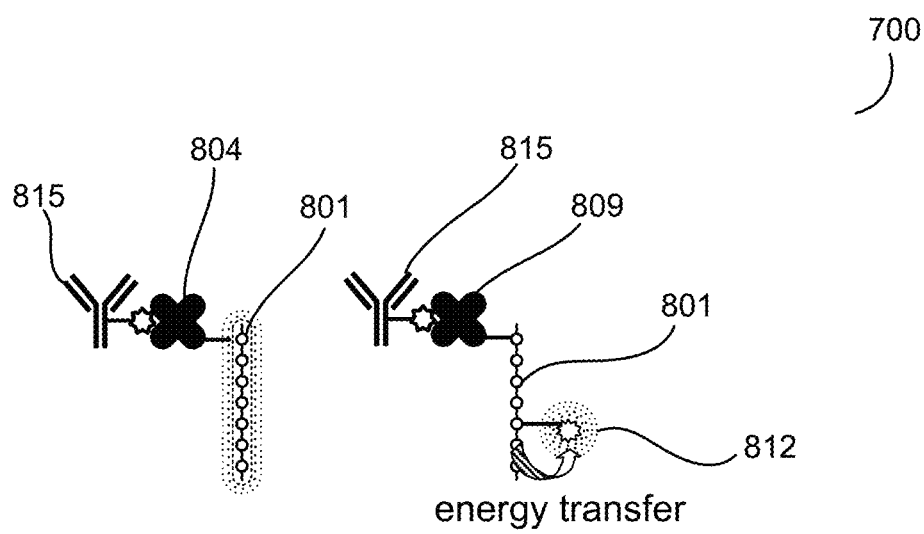
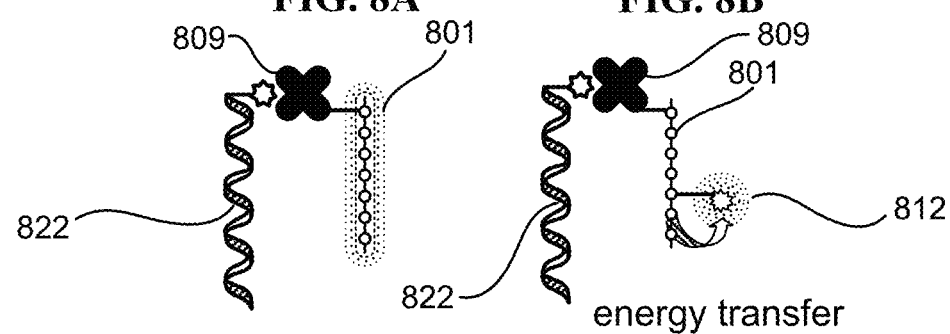
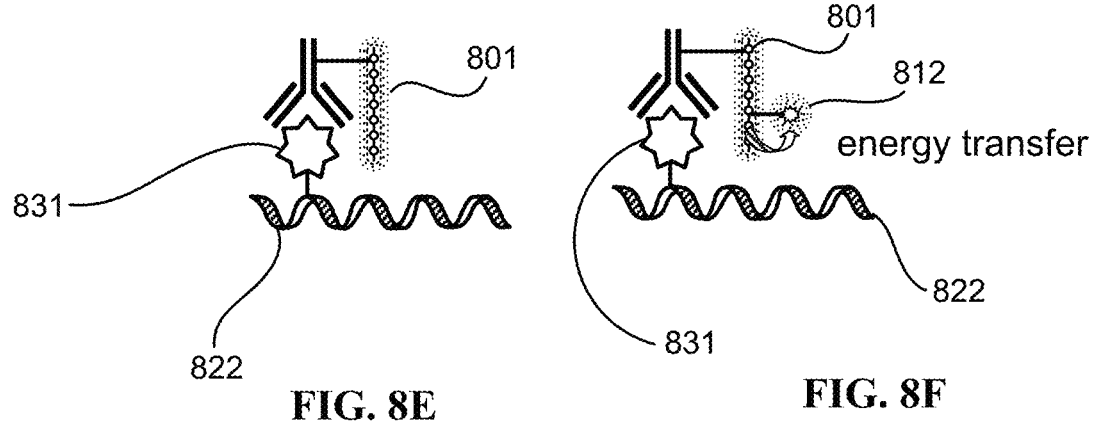
FIG. 8A  FIG. 8B
FIG. 8C  FIG. 8D
FIG. 8E  FIG. 8F 405 nm excitation;
400 – 500 nm emission 355 nm excitation;
400 – 500 nm emission 405 nm excitation;
400– 500 nm emission 355 nm excitation;
400– 500 nm emission

SUBSTITUTED POLYFLUORENE COMPOUNDS

CROSS-REFERENCE TO RELATED APPLICATIONS

The present application is a continuation of U.S. application Ser. No. 16/240,024, filed Jan. 4, 2019, allowed, which application is a continuation of PCT Application No. PCT/US2017/041187, filed on Jul. 7, 2017, which claims priority to U.S. Provisional Patent Application No. 62/360,155, filed Jul. 8, 2016, the disclosures of which are hereby incorporated by reference in their entirety for all purposes.

BACKGROUND OF THE INVENTION

Common dyes like Pacific Blue™, Alexa Fluor® 488 and Cy5 have high quantum yields, but limited extinction coefficients. Alternative reporters like phycobiliproteins offer much greater absorbance cross-sections, producing brighter signals, but are limited by rapid photobleaching and sensitivity to fixation.

Fluorophores are important in various bioassays formats. In fact, fluorescence is a common method for bioanalysis and biodetection and fluorescent labels are important in these applications. Some assays rely on fluorescence resonance energy transfer (FRET) mechanisms where two fluorophores are used. In these assays, energy is transferred between a donor fluorophore and an acceptor fluorophore if the two fluorophore are in close proximity to one another. Excitation of the "donor" by an energy source (e.g. UV light) produces an energy transfer to the "acceptor" if the two fluorophores are within a given proximity. In turn, the acceptor emits light at its characteristic wavelength. In order for FRET to occur, the fluorescence emission spectrum of the donor molecule must overlap with the absorption or excitation spectrum of the acceptor chromophore.

Polyfluorene polymers or macromers have well-defined structure, unique optical properties and are stable. Because the extinction coefficient of a macromer is directly proportional to the degree of polymerization (or number of repeat units), macromers are designed to improve brightness. Further, as these materials are derived from common synthetic organic and polymer chemistry techniques, it is possible to manufacture reagents which are more defined and reproducible, in terms of size, conjugation sites, physical properties, and optical properties.

Unlike say quantum dots, conjugated macromers have discrete excitation spectra, similar to that of organic dyes, which minimizes potential issues with cross-beam compensation.

In view of the foregoing, there is a need in the art for new polyfluorene macromers that are water-soluble and brighter than currently available technologies. The present invention satisfies these and other needs.

BRIEF SUMMARY OF THE INVENTION

The present invention provides polyfluorene macromers, methods for preparing the macromers as well as methods of using the macromers. In certain aspects, the macromers of formula I include one or more water-solubilizing groups. Water-soluble, conjugated polyfluorene macromers including one or more water-solubilizing groups render the macromers soluble in aqueous medium (e.g., water or buffers).

As such, in one embodiment, the present invention provide a polyfluorene macromer of formula I:

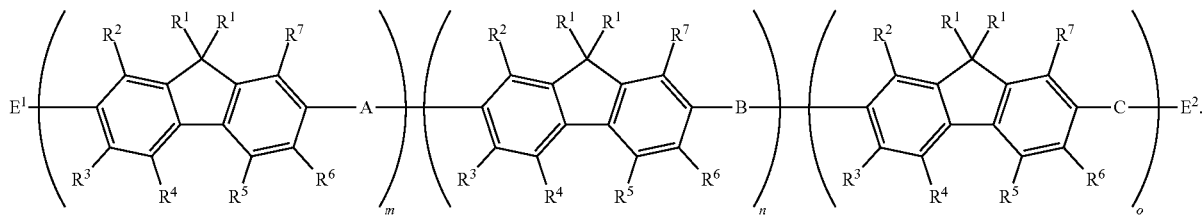

I

In formula I, adjacent $R^1$ groups on the same carbon atom form an optionally substituted 4-, 5-, or 6-membered ring, or in an alternative embodiment, when at least one of $R^2$, $R^3$, $R^4$, $R^5$, $R^6$, or $R^7$ is other than hydrogen on a given monomer, each $R^1$ of the same monomer may be the same or different and is selected from the group consisting of hydrogen, an optionally substituted $C_1$-$C_{18}$ alkyl, an optionally substituted $C_1$-$C_{18}$ alkoxy, an optionally substituted $C_6$-$C_{18}$ aryl, an optionally substituted $C_4$-$C_{18}$ acyl, an optionally substituted $C_4$-$C_{18}$ acyloxy, a functional group for conjugation to a molecule or biomolecule, a water solubilizing group, ethylene oxide oligomers or an ethylene oxide polymer. As described herein, "a monomer" refers to a portion of the polyfluorene macromer within a parenthesis such as m, n or o. In certain aspects, a monomer can have an aromatic or heteroaromatic (e.g., A, B, and/or C) group linked to the fluorene portion.

In formula I, each of $R^2$, $R^3$, $R^4$, $R^5$, $R^6$, and $R^7$ is independently selected from the group consisting of hydrogen, nitro, cyano, an optionally substituted amino, an optionally substituted $C_1$-$C_{18}$ alkyl, an optionally substituted $C_1$-$C_{18}$ alkoxy, optionally substituted $C_6$-$C_{18}$ aryl, optionally substituted $C_4$-$C_{18}$ acyl, optionally substituted $C_4$-$C_{18}$ acyloxy, a water solubilizing group, ethylene oxide oligomers or ethylene oxide polymer, and wherein each of $R^2$, $R^3$, $R^4$, $R^5$, $R^6$, and $R^7$ may be the same or different within o, n and m.

In certain aspects, $R^1$, $R^2$, $R^3$, $R^4$, $R^5$, $R^6$, and $R^7$ may be independently a functional group for conjugation to a molecule or biomolecule. For example, a functional group selected from amine, carbamate, carboxylic acid, carboxylate, maleimide, activated acyl, activated esters, N-hydroxysuccinimidyl, hydrazines, hydrazids, hydrazones, azide, alkyne, aldehydes, thiols, and protected groups thereof for conjugation to a molecule or biomolecule. In certain aspects, at least two, three, four or five of $R^1$, $R^2$, $R^3$, $R^4$, $R^5$, $R^6$, and $R^7$ within a given monomer may be a functional group for conjugation.

In formula I, m is a value selected from the group consisting of 1-10,000;

In formula I, n and o are each independently a value selected from the group consisting of 0-10,000, wherein the monomers within m, n, and o may be the same or different;

In formula I, each of A, B, and C can be present or absent and can each be the same or different, and each is selected from the group consisting of an aromatic group or heteroaromatic group, which group completes or comprises π-conjugated backbone.

In formula I, $E^1$ and $E^2$ are each independently a member selected from the group consisting of hydrogen, halogen, alkynyl, optionally substituted aryl, optionally substituted heteroaryl, halo, substituted aryl, boronic acid substituted aryl, boronic ester substituted aryl, boronic ester, boronic acid, optionally substituted fluorene and aryl or heteroaryl substituted with one or more pendant chains terminated with: i) a functional group selected from amine, carbamate, carboxylic acid, carboxylate, maleimide, activated esters, N-hydroxysuccinimidyl, hydrazines, hydrazids, hydrazones, azide, alkyne, aldehydes, thiols, and protected groups thereof for conjugation to a molecule or biomolecule; or ii) a conjugated organic dye or biomolecule.

In another embodiment, the present invention provides a method for detecting an analyte in a sample, the method comprising:
(a) combining the sample and a macromer of the invention;
(b) exciting the macromer with light; and
(c) detecting fluorescence from the macromer, thereby detecting the analyte.

The macromer conjugated to a biomolecule (e.g., an antibody) can be used as a direct reporter, for example, in a bioassay (e.g., an immunoassay). Excitation of the macromer with light can result in macromer emission, indicating the presence of the antibody in the assay or assay solution.

In yet another embodiment, the present invention provides a method for detecting a target biomolecule in a sample, the method comprising:
providing a sample that is suspected of containing a target analyte;
providing a macromer as described herein conjugated to a capture molecule, wherein the capture molecule is capable of interacting with the target analyte;
contacting the sample with the capture molecule and the conjugated macromer under conditions in which the capture molecule can bind to the target analyte if present;
applying a light source to the sample that excites the conjugated macromer; and
detecting whether light is emitted from the conjugated macromer.

In certain aspects, the method is performed in vivo or alternatively, in vitro. In certain aspects, the sample contains a living cell. In certain aspects, the analyte is a nucleic acid which comprises a genetic point mutation, deletion or insertion relative to a control nucleic acid. The control nucleic acid may contain a genetic mutation. In certain aspects, the detection of the nucleic acid indicates the presence of a cancer in the sample.

These and other aspects, objects and advantages will become more apparent when read with the detailed description and figures which follow.

BRIEF DESCRIPTION OF THE DRAWINGS

FIGS. 4A-D illustrate embodiments of the present invention; FIG. 4A illustrates an antibody labeled with a dye and a macromer according to the invention; FIG. 4B illustrates streptavidin labeled with a dye and labeled with a macromer according to the invention; FIG. 4C illustrates a nucleic acid probe sequence labeled with a quencher molecule conjugated to a macromer of the invention; and FIG. 4D illustrates a nucleic acid probe sequence labeled with a quencher molecule and macromer according to the invention.

FIG. 5A shows a macromer linked to a first antibody bound to a second antibody with a dye; FIG. 5B illustrates a macromer and dye labeled antibodies recognize a common target; FIG. 5C illustrates an antibody with a linked dye and biotin and a second bioconjugate of streptavidin with a macromer appended thereto; and FIG. 5D illustrates a nucleic acid with a dye and biotin bound thereto and streptavidin with a macromer conjugated thereto.

FIG. 7A depicts a macromer with a linked dye and a biomolecule resulting energy transfer; FIG. 7B illustrates a macromer with a conjugated streptavidin and a linked dye; and FIG. 7C illustrates a macromer conjugated to a nucleic acid and a dye.

FIGS. 8A-F illustrate schematics that depict indirect associations with macromers linked to a biomolecule; FIG. 8A shows a biotinylated antibody interacting with a covalent conjugate of a macromer; FIG. 8B shows a biotinylated antibody bound to moiety linked to a macromer having a linked dye; FIG. 8C shows a biotinylated nucleic acid interacting with a covalent moiety of a macromer; FIG. 8D shows a biotinylated nucleic acid bound to a linked moiety of a macromer having a linked dye; FIG. 8E shows a nucleic acid with digoxygenin moiety interacting with a covalently linked antibody of the macromer 801; and FIG. 8F shows a nucleic acid with digoxygenin moiety and a covalent antibody to a macromer dye tandem complex.

FIG. 9A shows a primary antibody 905 bound to an analyte wherein a secondary antibody having a macromer appended thereto is added; FIG. 9B shows a target analyte binding to a primary antibody with a linked macromer.

FIG. 10A shows a primary antibody that binds an analyte, and a secondary antibody with a biotin is then added, thereafter a macromer with a streptavidin is added to generate a sandwich complex; FIG. 10B shows a biotin labeled primary antibody with an analyte bound, thereafter, a streptavidin linked to a macromer is added.

DETAILED DESCRIPTION OF THE INVENTION

I. Definitions

Figure 1:
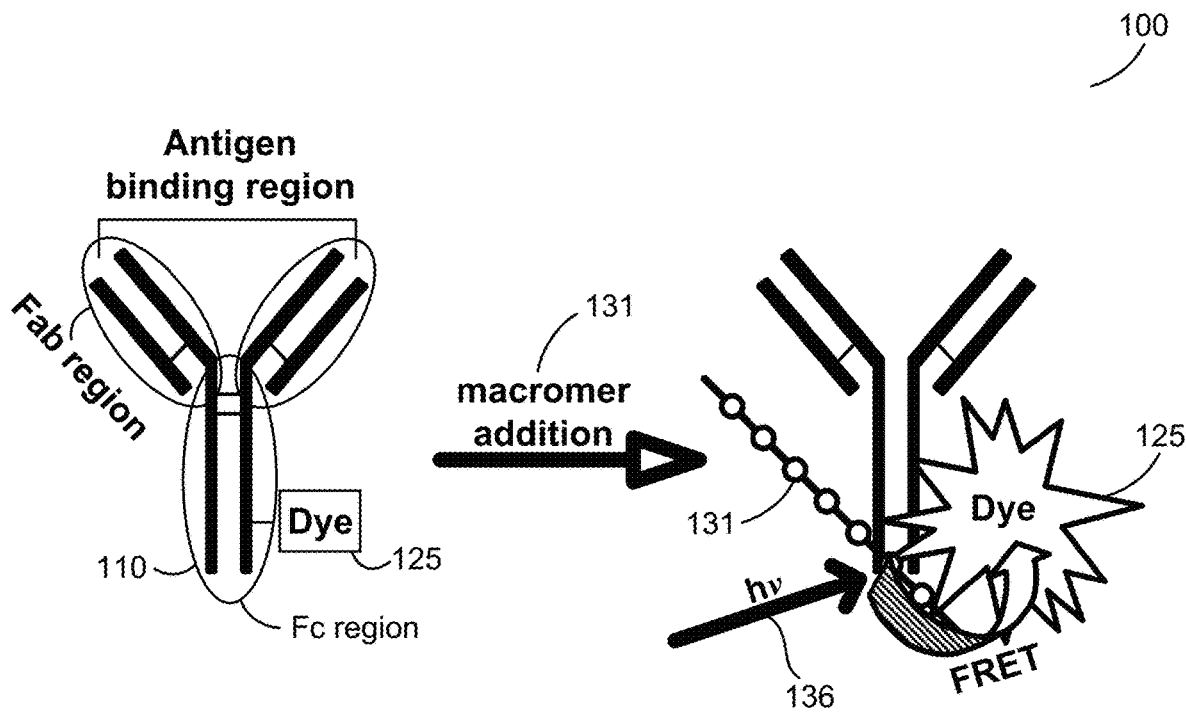
FIG. 1 illustrates an embodiment of the invention where an antibody labeled with a dye is reacted with a macromer.

The terms "a," "an," or "the" as used herein not only includes aspects with one member, but also includes aspects with more than one member.

The term "about" as used herein to modify a numerical value indicates a defined range around that value. If "X" were the value, "about X" would indicate a value from 0.9X to 1.1X, and more preferably, a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

When the modifier "about" is applied to describe the beginning of a numerical range, it applies to both ends of the range. Thus, "from about 500 to 850 nm" is equivalent to "from about 500 nm to about 850 nm." When "about" is applied to describe the first value of a set of values, it applies to all values in that set. Thus, "about 580, 700, or 850 nm" is equivalent to "about 580 nm, about 700 nm, or about 850 nm." However, when the modifier "about" is applied to describe only the end of the range or only a later value in the set of values, it applies only to that value or that end of the range. Thus, the range "about 2 to about 10" is the same as "about 2 to about 10," but the range "2 to about 10" is not.

"Activated acyl" as used herein includes a —C(O)-LG group. "Leaving group" or "LG" is a group that is susceptible to displacement by a nucleophilic acyl substitution (i.e., a nucleophilic addition to the carbonyl of —C(O)-LG, followed by elimination of the leaving group). Representative leaving groups include halo, cyano, azido, carboxylic acid derivatives such as t-butylcarboxy, and carbonate derivatives such as i-BuOC(O)O—. An activated acyl group may also be an activated ester as defined herein or a carboxylic acid activated by a carbodiimide to form an anhydride (preferentially cyclic) or mixed anhydride —OC(O)R$^a$ or —OC(NR$^a$)NHR$^b$ (preferably cyclic), wherein R$^a$ and R$^b$ are members independently selected from the group consisting of $C_1$-$C_6$ alkyl, $C_1$-$C_6$ perfluoroalkyl, $C_1$-$C_6$ alkoxy, cyclohexyl, 3-dimethylaminopropyl, or N-morpholinoethyl. Preferred activated acyl groups include activated esters.

"Activated ester" as used herein includes a derivative of a carboxyl group that is more susceptible to displacement by nucleophilic addition and elimination than an ethyl ester group (e.g., an NHS ester, a sulfo-NHS ester, a PAM ester, or a halophenyl ester). Representative carbonyl substituents of activated esters include succinimidyloxy (—$OC_4H_4NO_2$), sulfosuccinimidyloxy (—$OC_4H_3NO_2SO_3H$), -1-oxybenzotriazolyl (—$OC_6H_4N_3$); 4-sulfo-2,3,5,6-tetrafluorophenyl; or an aryloxy group that is optionally substituted one or more times by electron-withdrawing substituents such as nitro, fluoro, chloro, cyano, trifluoromethyl, or combinations thereof (e.g., pentafluorophenyloxy, 2,3,5,6-tetrafluorophenyloxy). Preferred activated esters include succinimidyloxy, sulfosuccinimidyloxy, and 2,3,5,6-tetrafluorophenyloxy esters.

"Acyl" as used herein includes an alkanoyl, aroyl, heterocycloyl, or heteroaroyl group as defined herein. Representative acyl groups include acetyl, benzoyl, nicotinoyl, and the like.

"Alkanoyl" as used herein includes an alkyl-C(O)— group wherein the alkyl group is as defined herein. Representative alkanoyl groups include acetyl, ethanoyl, and the like.

"Alkenyl" as used herein includes a straight or branched aliphatic hydrocarbon group of 2 to about 15 carbon atoms that contains at least one carbon-carbon double or triple bond. Preferred alkenyl groups have 2 to about 12 carbon atoms. More preferred alkenyl groups contain 2 to about 6 carbon atoms. In one aspect, hydrocarbon groups that contain a carbon-carbon double bond are preferred. In a second aspect, hydrocarbon groups that contain a carbon-carbon triple bond are preferred (i.e., alkynyl). "Lower alkenyl" as used herein includes alkenyl of 2 to about 6 carbon atoms. Representative alkenyl groups include vinyl, allyl, n-butenyl, 2-butenyl, 3-methylbutenyl, n-pentenyl, heptenyl, octenyl, decenyl, propynyl, 2-butynyl, 3-methylbutynyl, n-pentynyl, heptynyl, and the like.

An alkenyl group can be unsubstituted or optionally substituted. When optionally substituted, one or more hydrogen atoms of the alkenyl group (e.g., from 1 to 4, from 1 to 2, or 1) may be replaced with a moiety independently selected from the group of fluoro, hydroxy, alkoxy, amino, alkylamino, acylamino, thio, and alkylthio.

"Alkenylene" as used herein includes a straight or branched bivalent hydrocarbon chain containing at least one carbon-carbon double or triple bond. Preferred alkenylene groups include from 2 to about 12 carbons in the chain, and more preferred alkenylene groups include from 2 to 6 carbons in the chain. In one aspect, hydrocarbon groups that contain a carbon-carbon double bond are preferred. In a second aspect, hydrocarbon groups that contain a carbon-carbon triple bond are preferred. Representative alkenylene groups include —CH=CH—, —CH$_2$—CH=CH—, —C(CH$_3$)=CH—, —CH$_2$CH=CHCH$_2$—, ethynylene, propynylene, n-butynylene, and the like.

"Alkoxy" as used herein includes an alkyl-O— group wherein the alkyl group is as defined herein. Representative alkoxy groups include methoxy, ethoxy, n-propoxy, i-propoxy, n-butoxy, heptoxy, and the like.

An alkoxy group can be unsubstituted or optionally substituted. When optionally substituted, one or more hydrogen atoms of the alkoxy group (e.g., from 1 to 4, from 1 to 2, or 1) may be replaced with a moiety independently selected from the group of fluoro, hydroxy, alkoxy, amino, alkylamino, acylamino, thio, and alkylthio.

"Alkoxyalkyl" as used herein includes an alkyl-O-alkylene-group wherein alkyl and alkylene are as defined herein. Representative alkoxyalkyl groups include methoxyethyl, ethoxymethyl, n-butoxymethyl and cyclopentylmethyloxyethyl.

"Alkoxycarbonyl" as used herein includes an ester group; i.e., an alkyl-O—CO— group wherein alkyl is as defined herein. Representative alkoxycarbonyl groups include methoxycarbonyl, ethoxycarbonyl, t-butyloxycarbonyl, and the like.

"Alkoxycarbonylalkyl" as used herein includes an alkyl-O—CO-alkylene-group wherein alkyl and alkylene are as defined herein. Representative alkoxycarbonylalkyl include methoxycarbonylmethyl, ethoxycarbonylmethyl, methoxycarbonylethyl, and the like.

"Alkyl" as used herein includes an aliphatic hydrocarbon group, which may be straight or branched-chain, having about 1 to about 20 carbon atoms in the chain. Preferred alkyl groups have 1 to about 12 carbon atoms in the chain. More preferred alkyl groups have 1 to 6 carbon atoms in the chain. "Branched-chain" as used herein includes that one or more lower alkyl groups such as methyl, ethyl or propyl are attached to a linear alkyl chain. "Lower alkyl" as used herein includes 1 to about 6 carbon atoms, preferably 5 or 6 carbon atoms in the chain, which may be straight or branched. Representative alkyl groups include methyl, ethyl, n-propyl, isopropyl, n-butyl, t-butyl, n-pentyl, and 3-pentyl.

An alkyl group can be unsubstituted or optionally substituted. When optionally substituted, one or more hydrogen atoms of the alkyl group (e.g., from 1 to 4, from 1 to 2, or 1) may be replaced with a moiety independently selected from the group of fluoro, hydroxy, alkoxy, amino, alkylamino, acylamino, thio, and alkylthio.

"Alkylene" as used herein includes a straight or branched bivalent hydrocarbon chain of 1 to about 6 carbon atoms. Preferred alkylene groups are the lower alkylene groups having 1 to about 4 carbon atoms. Representative alkylene groups include methylene, ethylene, and the like.

"Alkylthio" as used herein includes an alkyl-S— group wherein the alkyl group is as defined herein. Preferred alkylthio groups are those wherein the alkyl group is lower alkyl. Representative alkylthio groups include methylthio, ethylthio, isopropylthio, heptylthio, and the like.

"Alkylthioalkyl" as used herein includes an alkylthio-alkylene-group wherein alkylthio and alkylene are defined herein. Representative alkylthioalkyl groups include methylthiomethyl, ethylthiopropyl, isopropylthioethyl, and the like.

"Amido" as used herein includes a group of formula Y$_1$Y$_2$N—C(O)— wherein Y$_1$ and Y$_2$ are independently hydrogen, alkyl, or alkenyl; or Y$_1$ and Y$_2$, together with the nitrogen through which Y$_1$ and Y$_2$ are linked, join to form a 4- to 7-membered azaheterocyclyl group (e.g., piperidinyl). Representative amido groups include primary amido (H$_2$N—C(O)—), methylamido, dimethylamido, diethylamido, and the like. Preferably, "amido" is an —C(O)NRR' group where R and R' are members independently selected from the group of H and alkyl. More preferably, at least one of R and R' is H.

"Amidoalkyl" as used herein includes an amido-alkylene-group wherein amido and alkylene are defined herein. Representative amidoalkyl groups include amidomethyl, amidoethylene, dimethylamidomethyl, and the like.

"Amino" as used herein includes a group of formula Y$_1$Y$_2$N— wherein Y$_1$ and Y$_2$ are independently hydrogen, acyl, or alkyl; or Y$_1$ and Y$_2$, together with the nitrogen through which Y$_1$ and Y$_2$ are linked, join to form a 4- to 7-membered azaheterocyclyl group (e.g., piperidinyl). Optionally, when Y$_1$ and Y$_2$ are independently hydrogen or alkyl, an additional substituent can be added to the nitrogen, making a quaternary ammonium ion. Representative amino groups include primary amino (H$_2$N—), methylamino, dimethylamino, diethylamino, and the like. Preferably, "amino" is an —NRR' group where R and R' are members independently selected from the group of H and alkyl. Preferably, at least one of R and R' is H.

"Aminoalkyl" as used herein includes an amino-alkylene-group wherein amino and alkylene are defined herein. Representative aminoalkyl groups include aminomethyl, aminoethyl, dimethylaminomethyl, and the like.

"Aroyl" as used herein includes an aryl-CO— group wherein aryl is defined herein. Representative aroyl include benzoyl, naphth-1-oyl and naphth-2-oyl.

"Aryl" as used herein includes an aromatic monocyclic or multicyclic ring system of 6 to about 14 carbon atoms, preferably of 6 to about 10 carbon atoms. Representative aryl groups include phenyl and naphthyl.

"Aromatic ring" as used herein includes 5-12 membered aromatic monocyclic or fused polycyclic moieties that may include from zero to four heteroatoms selected from the group of oxygen, sulfur, selenium, and nitrogen. Exemplary aromatic rings include benzene, pyrrole, furan, thiophene, imidazole, oxazole, thiazole, triazole, pyrazole, pyridine, pyrazine, pyridazine, pyrimidine, naphthalene, benzathiazoline, benzothiophene, benzofurans, indole, benzindole, quinoline, and the like. The aromatic ring group can be substituted at one or more positions with halo, alkyl, alkoxy, alkoxy carbonyl, haloalkyl, cyano, sulfonato, amino sulfonyl, aryl, sulfonyl, aminocarbonyl, carboxy, acylamino, alkyl sulfonyl, amino and substituted or unsubstituted substituents.

"Biomolecule" as used herein includes a natural or synthetic molecule for use in biological systems. Preferred biomolecules include an antibody, an antigen, a protein, a peptide, an enzyme substrate, a hormone, a hapten, an avidin, a streptavidin, a carbohydrate, a carbohydrate derivative, an oligosaccharide, a polysaccharide, and a nucleic acid. More preferred biomolecules include an antibody, a protein, a peptide, an avidin, a streptavidin, or biotin. In certain aspects, biomolecules include, but are not limited to, proteins, peptides, affinity ligands, antibodies, antibody fragments, sugars, lipids, enzymes and nucleic acids (as hybridization probes and/or aptamers).

"Carboxy" and "carboxyl" as used herein include a HOC(O)— group (i.e., a carboxylic acid) or a salt thereof.

"Carboxyalkyl" as used herein includes a HOC(O)-alkylene-group wherein alkylene is defined herein. Representative carboxyalkyls include carboxymethyl (i.e., HOC(O)CH$_2$—) and carboxyethyl (i.e., HOC(O)CH$_2$CH$_2$—).

A "conjugated macromer" as used herein includes a macromer that contains an extended series of unsaturated bonds. The backbone of the conjugated macromer or polymer can contain alternating double and single bonds. A conjugated polymer can be conjugated along the full length of its backbone or can contain conjugated segments together with non-conjugated segments.

"Conjugated" as used herein includes an unsaturated organic system having adjacent atoms with pi electrons where there is overlap of a p-orbital with another across an intervening sigma bond. In larger atoms d-orbitals can be involved. The atoms can be $sp^2$ or sp hybridized carbon atoms or other atoms with unshared electron pairs which can be hybridized into p orbitals.

"Cycloalkyl" as used herein includes a non-aromatic mono- or multicyclic ring system of about 3 to about 10 carbon atoms, preferably of about 5 to about 10 carbon atoms. More preferred cycloalkyl rings contain 5 or 6 ring atoms. A cycloalkyl group optionally comprises at least one $sp^2$-hybridized carbon (e.g., a ring incorporating an endocyclic or exocyclic olefin). Representative monocyclic cycloalkyl groups include cyclopentyl, cyclohexyl, cyclohexenyl, cycloheptyl, and the like. Representative multicyclic cycloalkyl include 1-decalin, norbornyl, adamantyl, and the like.

"Cycloalkylene" as used herein includes a bivalent cycloalkyl having about 4 to about 8 carbon atoms. Preferred cycloalkylenyl groups include 1,2-, 1,3-, or 1,4-cis- or trans-cyclohexylene.

"Halo" or "halogen" as used herein includes fluoro, chloro, bromo, or iodo.

"Heteroatom" as used herein includes an atom other than carbon or hydrogen.

Representative heteroatoms include O, S, and N. The nitrogen or sulphur atom of the heteroatom is optionally oxidized to the corresponding N-oxide, S-oxide (sulfoxide), or S,S-dioxide (sulfone). In a preferred aspect, a heteroatom has at least two bonds to alkylene carbon atoms (e.g., —$C_1$-$C_9$ alkylene-O—$C_1$-$C_9$ alkylene-). In some embodiments, a heteroatom is further substituted with an acyl, alkyl, aryl, cycloalkyl, heterocyclyl, or heteroaryl group (e.g., —N(Me)-; —N(Ac)—).

"Heteroaryl" as used herein refers to an aryl group in which at least one carbon atom in at least one aromatic ring is replaced by a heteroatom (e.g., nitrogen, oxygen, sulfur, and phosphorus), such that the aromaticity of the compound is retained, and can be optionally substituted at one or more substitutable positions. Exemplary heteroaryl groups include furanyl, thienyl, pyridyl, pyridazinyl, pyrrolyl, N-lower alkyl-pyrrolo, pyrimidyl, pyrazinyl, triazinyl, tetrazinyl, triazolyl, tetrazolyl, imidazolyl, bipyridyl, tripyridyl, tetrapyridyl, phenazinyl, phenanthrolinyl, purinyl, perylene, perylene diimide, kidetopyrrolopyrrole, benzothiodiazol, benzoxadiazol, thienopyrazine and the like. Additional examples of heteroaryl groups include fused ring systems, such as, for example, benzofuryl, benzothienyl, benzopyrrolyl, dibenzofuryl, dibenzothienyl, phenanthrolinyl, carbazolyl and azacarbazolyl groups.

"Heteroaroyl" as used herein includes a heteroaryl-C (O)— group wherein heteroaryl is as defined herein. Representative heteroaroyl groups include thiophenoyl, nicotinoyl, pyrrol-2-ylcarbonyl, pyridinoyl, and the like.

"Heterocycloyl" as used herein includes a heterocyclyl-C(O)— group wherein heterocyclyl is as defined herein. Representative heterocycloyl groups include N-methyl prolinoyl, tetrahydrofuranoyl, and the like.

"Hydroxyalkyl" as used herein includes an alkyl group as defined herein substituted with one or more hydroxy groups. Preferred hydroxyalkyls contain lower alkyl. Representative hydroxyalkyl groups include hydroxymethyl and 2-hydroxyethyl.

The term "optionally substituted" means that the substituent may be substituted or unsubstituted. For example, a hydrogen atom of an alkyl group (e.g., from 1 to 4, from 1 to 2, or 1) may be replaced with a moiety independently selected from the group of fluoro, hydroxy, alkoxy, amino, alkylamino, acylamino, thio, and alkylthio. An aromatic ring group can be substituted at one or more positions with halo, alkyl, alkoxy, alkoxy carbonyl, haloalkyl, cyano, sulfonato, amino sulfonyl, aryl, sulfonyl, aminocarbonyl, carboxy, acylamino, alkyl sulfonyl, amino and substituted or unsubstituted substituents. In an analogous fashion, each of the substituent groups referred to herein can be analogously substituted, with amino, halo, hydroxy, alkoxy, cyano, nitro, alkylamino, acylamino, thio, alkylthio, alkyl, alkoxy carbonyl, haloalkyl, sulfonato, aminosulfonyl, aryl, sulfonyl, aminocarbonyl, carboxy, acylamino, and alkylsulfonyl.

"The number average molecular weight" includes the arithmetic mean or average of the molecular masses of the individual macromolecules. It is determined by measuring the molecular mass of n polymer molecules, summing the masses, and dividing by n. On the other hand, weight average molecular weight ($M_w$) takes into account the molecular weight of a chain in determining contributions to the molecular weight average. The more massive the chain, the more the chain contributes to $M_w$. $M_w$ is determined by methods that are sensitive to the molecular size rather than just their number, such as light scattering techniques.

"Water-soluble" as used herein includes a material that is soluble in an aqueous-based solution, such as in water, water-based solutions or buffer solutions, including those used in biological or molecular detection systems. A "water-soluble" solution refers to a homogeneous solution containing fully dissolved material. A "water-soluble" macromer of this invention is soluble in an aqueous-based solution at a concentration of >0.10 mg/mL. Incorporation of at least one "water-solubilizing group" into the material can increase the hydrophilicity of the material and can improve the solubility or dispersibility of the material in an aqueous environment.

II. Embodiments

A. Compounds

The present invention provides polyfluorene macromers, methods for preparing the polyfluorene macromers as well as methods of using the polyfluorene macromers. In certain aspects, the polyfluorene macromers of formula I include one or more water-solubilizing groups. Water-soluble, conjugated polyfluorene macromers including one or more water-solubilizing groups render the polyfluorene macromers soluble in aqueous medium (e.g., water or buffers). The polyfluorene macromers are suitable for use in various types of biological applications. The polyfluorene macromers emit bright, visible light upon UV excitation (e.g., resulting from irradiation with a violet laser) and can exhibit high extinction coefficients and quantum efficiency (e.g., quantum yield >50%, such as >60%, >65%, >70%, >75%, or greater).

As such, in one embodiment, the present invention provide a polyfluorene macromer of formula I:

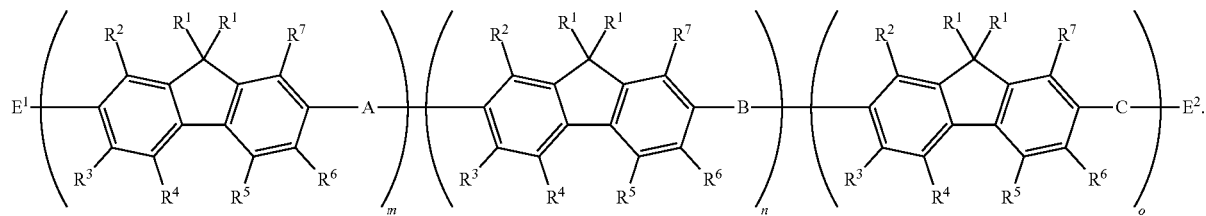

In formula I, m is a value selected from 1-10,000. In certain aspects, the value of m is 1-10,000 such as 1 to 10, 1 to 20, 1 to 30, 1 to 40, 1 to 50, 1 to 60, 1 to 70, 1 to 80, 1 to 90, 1 to 100, 1 to 200, 1 to 300, 1 to 400, 1 to 500, 1 to 600, 1 to 700, 1 to 800, 1 to 900, 1 to 1000, 1 to 1 to 2000, 1 to 3000, 1 to 4000, 1 to 5000, 1 to 6000, 1 to 7000, 1 to 8000, 1 to 9000 or 1 to 10000. In certain instances, m is a value selected from 1-50 such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50.

In formula I, adjacent $R^1$ groups on the same carbon atom form an optionally substituted 4-, 5-, or 6-membered ring, or in an alternative embodiment, when at least one of $R^2$, $R^3$, $R^4$, $R^5$, $R^6$, or $R^7$ is other than hydrogen on a given monomer, each $R^1$ of the same monomer may be the same or different and is selected from the group consisting of hydrogen, an optionally substituted $C_1$-$C_{18}$ alkyl, an optionally substituted $C_1$-$C_{18}$ alkoxy, an optionally substituted $C_6$-$C_{18}$ aryl, an optionally substituted $C_4$-$C_{18}$ acyl, an optionally substituted $C_4$-$C_{18}$ acyloxy, a functional group for conjugation to a molecule or biomolecule, a water solubilizing group, ethylene oxide oligomers or ethylene oxide polymer. As described herein, "a monomer" refers to a portion of the polyfluorene macromer within a parenthesis such as m, n or o. In certain aspects, a monomer can have an aromatic or heteroaromatic (e.g., A, B, and/or C) group linked to the fluorene portion.

In formula I, each of $R^2$, $R^3$, $R^4$, $R^5$, $R^6$, and $R^7$ is independently selected from the group consisting of hydrogen, nitro, cyano, an optionally substituted amino, an optionally substituted $C_1$-$C_{18}$ alkyl, an optionally substituted $C_1$-$C_{18}$ alkoxy, optionally substituted $C_6$-$C_{18}$ aryl, optionally substituted $C_4$-$C_{18}$ acyl, optionally substituted $C_4$-$C_{18}$ acyloxy, a water solubilizing group, ethylene oxide oligomers or ethylene oxide polymer, and wherein each of $R^2$, $R^3$, $R^4$, $R^5$, $R^6$, and $R^7$ may be the same or different within o, n and m.

In certain aspects, $R^1$, $R^2$, $R^3$, $R^4$, $R^5$, $R^6$, and $R^7$ can independently be a functional group for conjugation to a molecule or biomolecule. For example, a functional group selected from amine, carbamate, carboxylic acid, carboxylate, maleimide, activated acyl, activated esters, N-hydroxysuccinimidyl, hydrazines, hydrazids, hydrazones, azide, alkyne, aldehydes, thiols, and protected groups thereof for conjugation to a molecule or biomolecule. In certain aspects, at least two, three, four or five of $R^1$, $R^2$, $R^3$, $R^4$, $R^5$, $R^6$, and $R^7$ are functional groups for conjugation.

In formula I, a water solubilizing group is a group that imparts more hydrophilicity to the macromer. A water solubilizing group can be an ethylene oxide oligomer or an ethylene oxide polymer. In certain aspects, water-solubilizing groups include one or more alkylene oxide repeat units. For example, a water-solubilizing group can contain one or more ethylene glycol units, —(OCH$_2$CH$_2$)—. Ethylene glycol oligomers or polymers are referred to herein as a "polyethylene glycol" (PEG) group. The PEG group can be any length, however, typically includes between 1 to 20 ethylene glycol repeat units. In certain embodiments, PEG groups having more than 20 ethylene glycol repeat units are used.

In formula I, other water solubilizing groups include w-ammonium alkoxy salts, and w-sulfonate alkoxy salts.

Within formula I, n and o are each independently a value selected from the group consisting of 0-10,000, wherein the monomers within m, n, and o may be the same or different. In certain aspects, the values of n and o are each independently a value selected from the group consisting of 0-10, 000, such as 0, 1, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000 or 10000.

In formula I, each of A, B, and C can be present or can be absent and can each be the same or different, and each is selected from the group consisting of an aromatic group or heteroaromatic group, which group completes or comprises π-conjugated backbone. The aromatic group or heteroaromatic group can be optionally substituted.

In formula I, $E^1$ and $E^2$ are each independently a member selected from the group consisting of hydrogen, halogen, alkynyl, optionally substituted aryl, optionally substituted heteroaryl, halo, substituted aryl, boronic acid substituted aryl, boronic ester substituted aryl, boronic ester, boronic acid, optionally substituted fluorene and aryl or heteroaryl substituted with one or more pendant chains terminated with: i) a functional group selected from amine, carbamate, carboxylic acid, carboxylate, maleimide, activated esters, N-hydroxysuccinimidyl, hydrazines, hydrazids, hydrazones, azide, alkyne, aldehydes, thiols, and protected groups thereof for conjugation to a molecule or biomolecule; or ii) a conjugated organic dye or biomolecule.

The macromers of formula I are prepared using monomers of the following general formula:

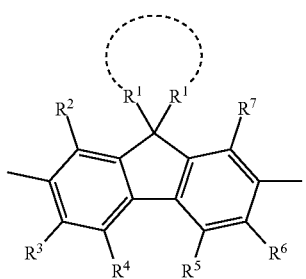

wherein $R^1$, $R^2$, $R^3$, $R^4$, $R^5$, $R^6$, and $R^7$ each has the meaning in formula I. The dashed circle between the adjacent $R^1$ groups on the same carbon represents an optionally substituted 4-, 5-, or 6-membered ring. The monomers of the present invention can be made according to the literature by using starting materials such as 2,7 dibromofluorene, 2,7 dibromofluorenone, or their substituted derivatives at positions 9 and 1, 3, 4, 5, 6, and/or 8. Typical monomers of the invention are discussed herein.

In certain instances, the polyfluorene macromers of formula I comprise at least one monomer residue substituted with one or more water-solubilizing groups. In certain instances, the backbone of the polyfluorene macromers of formula I include a plurality of monomer residues. The macromer backbone can include a conjugated segment. The polymer backbone can further include at least one monomer residues that comprise an optionally substituted aromatic or heteroaromatic group appended to the fluorene monomer, which is A, B and/or C.

In certain aspects, each of A, B, and C in formula I may be present or absent. If present, A, B, and C may be the same or different. A, B and C represent a divalent substituent, which is a divalent group selected from the group consisting of benzene, naphthalene, anthracene, benzodiathiazolyl, fluorene, indenofluorene, thiophene, thienothiophene, dithienothiophene, 3,4-ethylenedioxythiophene, furan, pyridine, pyrrole, fused pyrrole, tetrahydropyrene and oxadiazole. Each of the foregoing groups may be optionally substituted.

In certain aspects, two adjacent $R^1$ groups on the same carbon within m, n and/or o, form an optionally substituted 4-, 5-, or 6-membered ring selected from the group consisting of optionally substituted $C_4$-$C_6$ cycloalkyl group and an optionally substituted $C_4$-$C_6$ heterocyclyl group. For example, two adjacent $R^1$ groups on the same carbon form an optionally substituted $C_4$-cycloalkyl, a $C_5$-cycloalkyl or a $C_6$-cycloalkyl group. In one aspect, when two adjacent $R^1$ groups form an optionally substituted 4-, 5-, or 6-membered ring, it generates a bicyclic ring system (within the larger ring system), where the two rings are connected through a single common atom. This common atom joining the bicyclic rings is generally referred to as a "spiro" atom.

In certain instances, the $C_4$-$C_6$ cycloalkyl group is substituted with at least one ethylene oxide oligomer such as a —$(CH_2)_y$—$(OCH_2CH_2)_xOCH_3$ group, wherein y is a value from 1-20 and x is a value from 1-50. For example, the value of y can be 1, 2, 3, 4, 5, 6, 7, 8, 9, 10, 11, 12, 13, 14, 15, 16, 17, 18, 19, or 20. The value of x can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. The ethylene oxide oligomers enhance the water solubility of the macromer.

In certain aspects, the $C_4$-$C_6$ heterocyclyl group is a member selected from the group consisting of an azetidinyl, oxetanyl, thietanyl, a pyrrolidinyl, an oxolanyl, a thiolanyl, a piperidinyl, an oxanyl and a thianyl or an optionally substituted tetrahydropyranyl such as a xanthenyl. In certain preferred aspects, the $C_4$-$C_6$ heterocyclyl group is an optionally substituted pyrrolidinyl group or a piperidinyl group.

In certain aspects, the $C_4$-$C_6$ heterocyclyl group is substituted with at least one ethylene oxide oligomer such as a —$(CH_2)_y$—$(OCH_2CH_2)_xOCH_3$ group, wherein y is value from 1-20 and x is a value from 1-50.

In certain aspects, $R^1$ is $C_3$-$C_{18}$ perfluoroalkyl. The $C_3$-$C_{18}$ perfluoroalkyl can be a $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$ or $C_{18}$ perfluoroalkyl.

In certain aspects, at least one of $R^2$, $R^3$, $R^4$, $R^5$, $R^6$, and $R^7$ is $C_3$-$C_{18}$ perfluoroalkyl such as $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$ or $C_{18}$ perfluoroalkyl.

In certain aspects, and where applicable, the definition for each substituent of formula I above is incorporated herein by reference for each of the following sub genera:

In certain aspects, the polyfluorene macromer of formula I has the following formula:

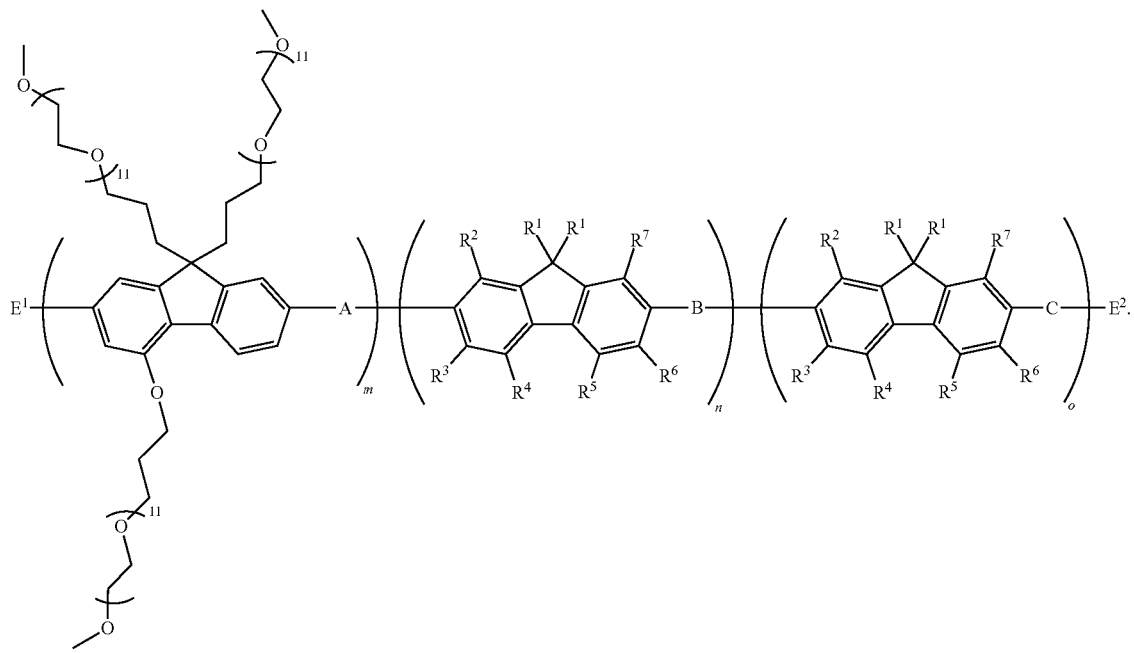

wherein m is 1-200; n is 0 to 1000; and o is 0 to 1000. When n has a value of 0, the monomer within n is absent. Similarly, when o has a value of 0, the monomer within o is absent. The value of m can be 1-200, such as 1-10, 1-20, 1-30, 1-40, 1-50, 1-60, 1-70, 1-80, 1-90, 1-100, 1-125, 1-150, or 1-200. In certain aspects, m can be 1, 2, 3, 4, 5, 6, 7, 8, 9, 10, 11, 12, 13, 14, or 15.

In certain aspects, each A, B, and C, if present, is a divalent substituent member selected from the group consisting of benzene, naphthalene and anthracene. In certain aspects, A, B and C are the same or alternatively, they can be different. A, B and C can optionally be substituted.

In certain aspects, each the monomers within m, n and o are the same. Alternatively, they can be different.

In certain aspects, m is 1-15; n is 0 and o is 0. For example, the value of m can be 1, 2, 3, 4, 5, 6, 7, 8, 9, 10, 11, 12, 13, 14, or 15.

In one aspect, $E^1$ and $E^2$ are each independently a member selected from the group consisting of hydrogen and a functional moiety which is a member selected from the group of an amine, a carbamate, a carboxylic acid, a carboxylate, a maleimide, an activated ester, N-hydroxysuccinimidyl, a hydrazine, a hydrazid, a hydrazone, an azide, an alkyne, an aldehyde, a thiol, an alkyl halide and protected groups thereof for conjugation to a molecule or biomolecule.

Biomolecules include, but are not limited to, an antibody, an antigen, a protein, a peptide, an enzyme substrate, a hormone, a hapten, an avidin, a streptavidin, a carbohydrate, a carbohydrate derivative, an oligosaccharide, a polysaccharide, and a nucleic acid. More preferred biomolecules include an antibody, a protein, a peptide, an avidin, a streptavidin, or biotin. In certain aspects, biomolecules include, but are not limited to, proteins, peptides, affinity ligands, antibodies, antibody fragments, sugars, lipids, enzymes and nucleic acids (as hybridization probes and/or aptamers).

The macromers of formula I can react with a biomolecule using conjugation chemistry well known in the art. For example, an activated ester (an NHS ester) can react with a primary amine to make a stable amide bond. A maleimide and a thiol can react together and make a thioether. Alkyl halides react with amines and thiols to make alkylamines and thioethers, respectively. Any derivative providing a reactive moiety that can be conjugated to a protein or biomolecule can be utilized herein.

In certain aspects, the macromer of formula I has the following formula:

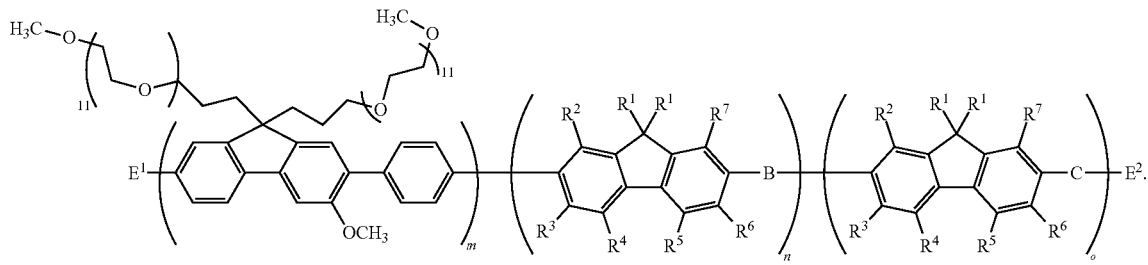

In certain aspects, B and C are the same. For example, B and C are both divalent phenyl groups. In other aspects, B and C are different.

In certain aspects, m is 1-15; n is 0 and o is 0. For example, the value of m can be 1, 2, 3, 4, 5, 6, 7, 8, 9, 10, 11, 12, 13, 14, or 15.

In certain aspects, the macromer of formula I has the following formula:

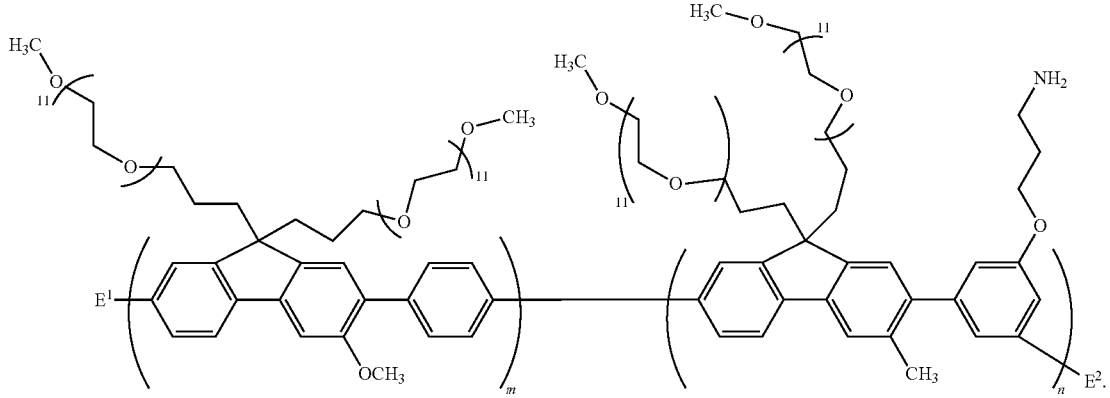

In certain aspects, m is 1-15; and n is 1-15. For example, the value of m and n are independently 1, 2, 3, 4, 5, 6, 7, 8, 9, 10, 11, 12, 13, 14, or 15 such as m is 1-15; and n is 1.

In certain aspects, the macromer of formula. T has the formula:

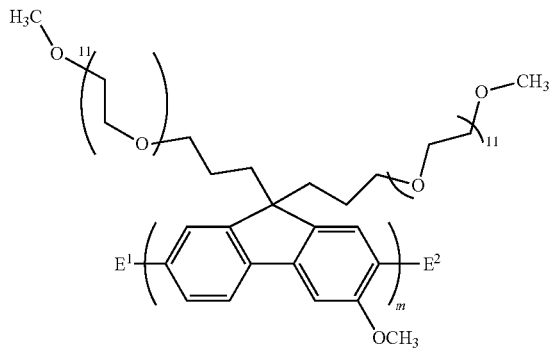

In certain aspects, m is 1-15 such as 1, 2, 3, 4, 5, 6, 7, 8, 9, 10, 11, 12, 13, 14, or 15. In one aspect, $E^1$ is hydrogen and $E^2$ is a N-hydroxysuccinimidyl group.

In certain aspects, the macromer of formula I has the formula selected from:

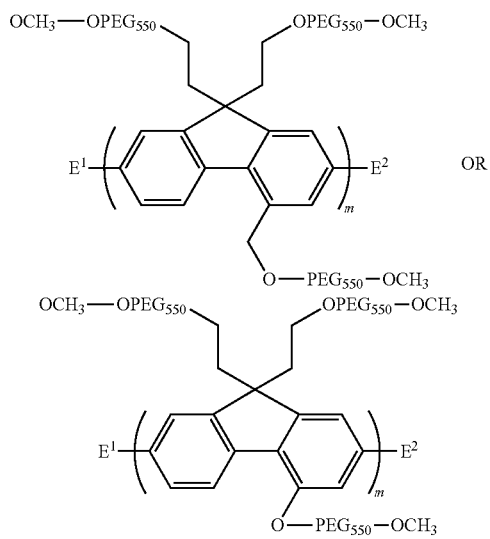

In certain aspects, m is 1-50 or 1-15 such as 1, 2, 3, 4, 5, 6, 7, 8, 9, 10, 11, 12, 13, 14, or 15. $E^1$ and $E^2$ are each independently a member selected from the group consisting of hydrogen, halogen, alkynyl, optionally substituted aryl, optionally substituted heteroaryl, halo, substituted aryl, boronic acid substituted aryl, boronic ester substituted aryl, boronic ester, boronic acid, optionally substituted fluorene and aryl or heteroaryl substituted with one or more pendant chains terminated with: i) a functional group selected from amine, carbamate, carboxylic acid, carboxylate, maleimide, activated esters, N-hydroxysuccinimidyl, hydrazines, hydrazids, hydrazones, azide, alkyne, aldehydes, thiols, and protected groups thereof for conjugation to a molecule or biomolecule; or ii) a conjugated organic dye or biomolecule. In one aspect, $E^1$ is hydrogen and $E^2$ is a N-hydroxysuccinimidyl group.

In certain aspects, $PEG_{550}$-$OCH_3$ has the formula of $CH_3$—$(O$—$CH_2$—$CH_2)_x$— with a number average molecular weight of 550 and a terminal methoxy group. In certain aspects, x is 11 or 12. In certain aspects, m is 1-15 such as 1, 2, 3, 4, 5, 6, 7, 8, 9, 10, 11, 12, 13, 14, or 15. In other aspects, m is 1-30, or 1-40, or 1-50.

In certain aspects, the macromer of formula I has the following formula:

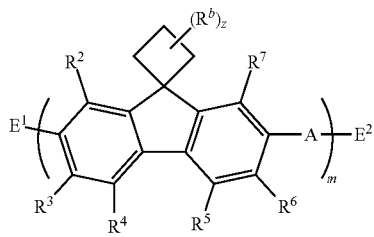

In certain aspects, $R^b$ is a member selected from the group consisting of hydrogen, an optionally substituted $C_1$-$C_{18}$ alkyl, an optionally substituted $C_1$-$C_{18}$ alkoxy, optionally substituted $C_6$-$C_{18}$ aryl, optionally substituted $C_4$-$C_{18}$ acyl, optionally substituted $C_4$-$C_{18}$ acyloxy, a water solubilizing group, ethylene oxide oligomers and ethylene oxide polymer. In one aspect, $R^b$ is a functional group for conjugation to a molecule or biomolecule.

In certain aspects, A is either present or absent and is a member selected from the group consisting of a divalent phenyl group and a divalent benzodiathiazolyl group.

In certain aspects, z is a value of 0 to 4, such as 0, 1, 2, 3, or 4.

In certain aspects, the macromer of formula I has the following formula:

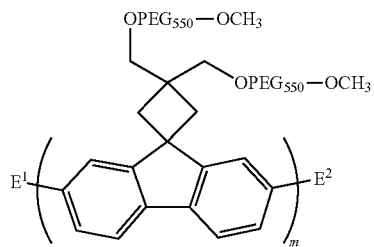

In certain aspects, $PEG_{550}$-$OCH_3$ has the formula of $CH_3$—$(O$—$CH_2$—$CH_2)_x$— with a number average molecular weight of 550 and a terminal methoxy group. In certain aspects, m is 1-15 such as 1, 2, 3, 4, 5, 6, 7, 8, 9, 10, 11, 12, 13, 14, or 15. In other aspects, m is 1-30, or 1-40, or 1-50, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

In certain aspects, the macromer of formula I has the following formula:

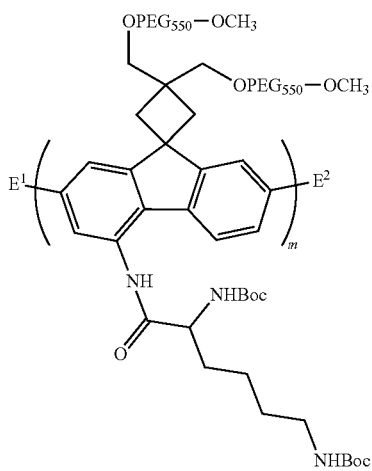

In certain aspects, m is 1-15 such as 1, 2, 3, 4, 5, 6, 7, 8, 9, 10, 11, 12, 13, 14, or 15. In other aspects, m is 1-30, or 1-40, or 1-50. The Boc groups can be removed and a water soluble group installed or alternatively, a site for conjugation. An example of a water soluble group is ethylene oxide oligomer such as a —(CH$_2$)$_y$—(OCH$_2$CH$_2$)$_x$OCH$_3$ group, wherein y is a value from 1-20 and x is a value from 1-50. For example, the value of y can be 1, 2, 3, 4, 5, 6, 7, 8, 9, 10, 11, 12, 13, 14, 15, 16, 17, 18, 19, or 20. The value of x can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. A site for conjugation can be i) a functional group selected from amine, carbamate, carboxylic acid, carboxylate, maleimide, activated esters, N-hydroxysuccinimidyl, hydrazines, hydrazids, hydrazones, azide, alkyne, aldehydes, thiols, and protected groups thereof for conjugation to a molecule or biomolecule; or ii) a conjugated organic dye or biomolecule. In the above, R$^4$ is an substituted amido group of NHC(O) CH(NH$_2$)CH$_2$CH$_2$CH$_2$CH$_2$NH$_2$, wherein the amine are protected by Boc.

In certain aspects, the macromer of formula I has the following formula:

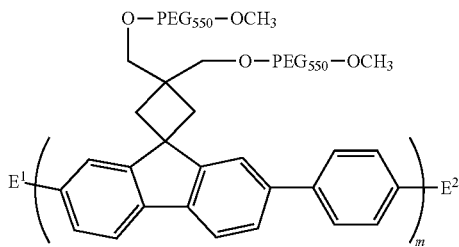

In certain aspects, PEG$_{550}$-OCH$_3$ has the formula of CH$_3$—(O—CH$_2$—CH$_2$), with a number average molecular weight of 550 and a terminal methoxy group. Polyethylene glycol monomethyl ether, "mPEG" has the linear formula CH$_3$(OCH$_2$CH$_2$)$_n$OH with an average M$_n$ of 550. Other M$_n$ include, but are not limited to 350, 750, 2000 and 5000. In certain aspects, m is 1-15 such as 1, 2, 3, 4, 5, 6, 7, 8, 9, 10, 11, 12, 13, 14, or 15. In other aspects, m is 1-30, or 1-40, or 1-50.

In certain aspects, the macromer of formula I has the following formula:

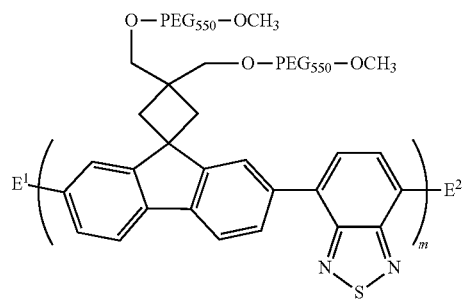

wherein m is 1-50.

In certain aspects, the macromer of formula I has the following formula:

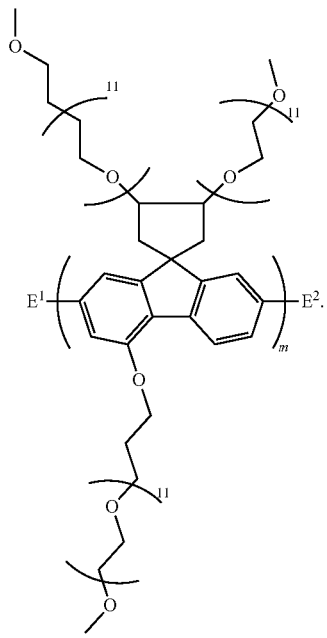

In certain aspects, m is 1-15 such as 1, 2, 3, 4, 5, 6, 7, 8, 9, 10, 11, 12, 13, 14, or 15. In one aspect, E$^1$ is hydrogen and E$^2$ is a N-hydroxysuccinimidyl group.

In certain aspects, the macromer of formula I has the following formula:

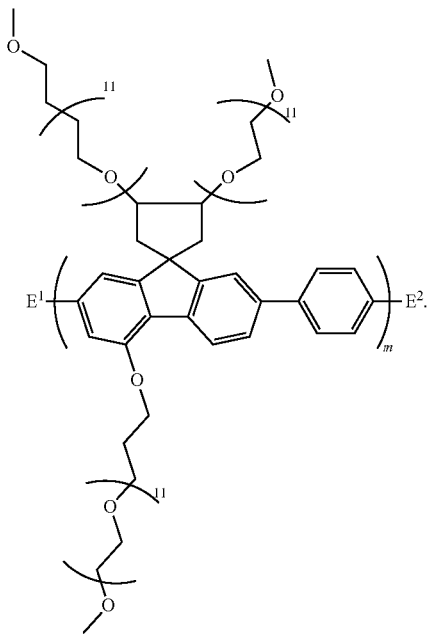

In certain aspects, m is 1-15 such as 1, 2, 3, 4, 5, 6, 7, 8, 9, 10, 11, 12, 13, 14, or 15. In one aspect, $E^1$ is hydrogen and $E^2$ is a N-hydroxysuccinimidyl group.

In certain aspects, the macromer of formula I has the following formula:

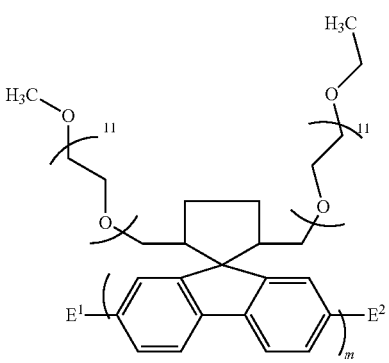

In certain aspects, m is 1-15 such as 1, 2, 3, 4, 5, 6, 7, 8, 9, 10, 11, 12, 13, 14, or 15. In one aspect, $E^1$ is hydrogen and $E^2$ is a N-hydroxysuccinimidyl group.

In one aspect, $E^2$ is a biomolecule selected from group consisting of an antibody, an antigen, a protein, a peptide, an enzyme substrate, a hormone, a hapten, an avidin, a streptavidin, a carbohydrate, a carbohydrate derivative, an oligosaccharide, a polysaccharide, and a nucleic acid.

In certain aspects, the macromer of formula I has the following formula selected from the group:

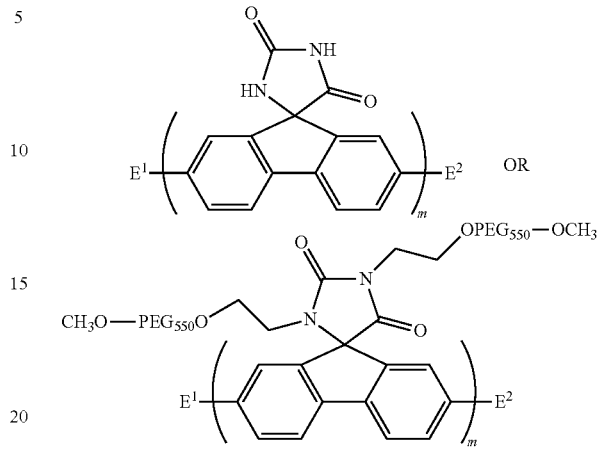

In certain aspects, m is 1-50 or 1-15 such as 1, 2, 3, 4, 5, 6, 7, 8, 9, 10, 11, 12, 13, 14, or 15. $E^1$ and $E^2$ are each independently a member selected from the group consisting of hydrogen, halogen, alkynyl, optionally substituted aryl, optionally substituted heteroaryl, halo, substituted aryl, boronic acid substituted aryl, boronic ester substituted aryl, boronic ester, boronic acid, optionally substituted fluorene and aryl or heteroaryl substituted with one or more pendant chains terminated with: i) a functional group selected from amine, carbamate, carboxylic acid, carboxylate, maleimide, activated esters, N-hydroxysuccinimidyl, hydrazines, hydrazids, hydrazones, azide, alkyne, aldehydes, thiols, and protected groups thereof for conjugation to a molecule or biomolecule; or ii) a conjugated organic dye or biomolecule. In one aspect, $E^1$ is hydrogen and $E^2$ is a N-hydroxysuccinimidyl group.

In certain aspects, the macromer of formula I has the following formula:

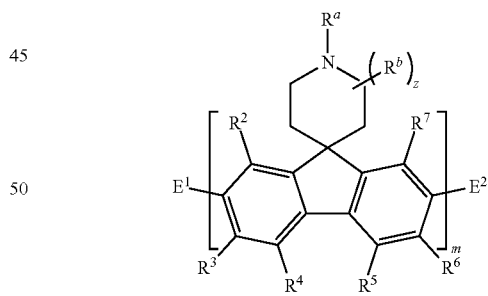

wherein $R^a$ is a member selected from the group consisting of hydrogen, an optionally substituted $C_1$-$C_{18}$ alkyl, an optionally substituted $C_1$-$C_{18}$ alkoxy, optionally substituted $C_6$-$C_{18}$ aryl, optionally substituted $C_4$-$C_{18}$ acyl, optionally substituted $C_4$-$C_{18}$ acyloxy, a water solubilizing group, ethylene oxide oligomers, ethylene oxide polymer, and a functional group for conjugation to a molecule or biomolecule;

wherein $R^b$ is a member selected from the group consisting of hydrogen, an optionally substituted $C_1$-$C_{18}$ alkyl, an optionally substituted $C_1$-$C_{18}$ alkoxy, an optionally substituted $C_6$-$C_{18}$ aryl, an optionally substituted C4-C18 acyl, an optionally substituted C4-C18 acyloxy, a water solubilizing group, ethylene oxide oligomers, ethylene oxide polymer or a site for conjugation; and z is a value of 0 to 4, such as 0, 1, 2, 3, or 4.

In certain aspects, the macromer of formula I has the following formula:

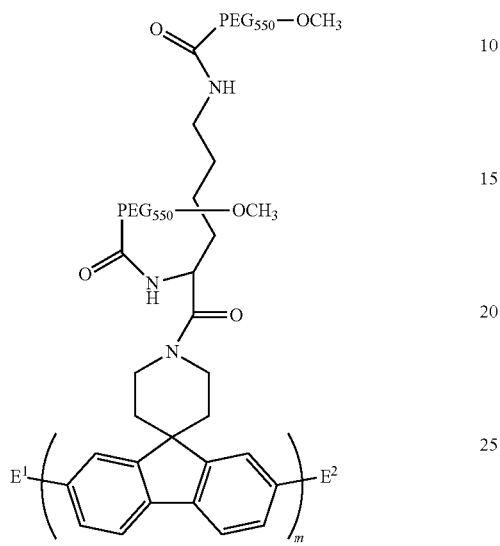

wherein $PEG_{550}$ has the formula of $CH_3(-O-CH_2-CH_2)_x$ with a number average molecular weight of 550 and m is 1-50.

In certain aspects, the macromer of formula I has the following formula:

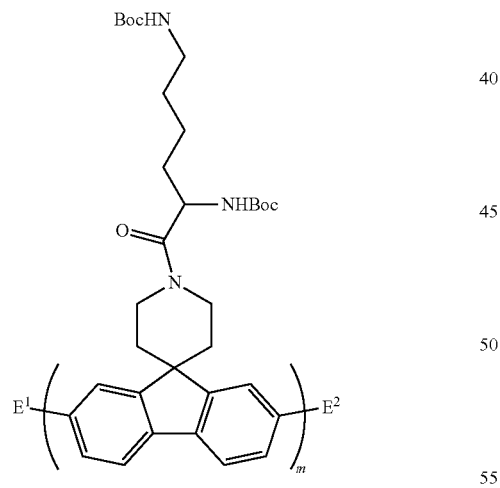

the value of m is 1-15 such as 1, 2, 3, 4, 5, 6, 7, 8, 9, 10, 11, 12, 13, 14 or 15 or 1-30, 1-40, or 1-50. In one aspect, $E^1$ is hydrogen and $E^2$ is a N-hydroxysuccinimidyl group. The Boc groups can be removed and a water solubilizing group, ethylene oxide oligomers and ethylene oxide polymer, or it can be a site for conjugation. An example of a water soluble group is ethylene oxide oligomer such as a $-(CH_2)_y-(OCH_2CH_2)_xOCH_3$ group, wherein y is a value from 1-20 and x is a value from 1-50. For example, the value of y can be 1, 2, 3, 4, 5, 6, 7, 8, 9, 10, 11, 12, 13, 14, 15, 16, 17, 18, 19, or 20. The value of x can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. A site for conjugation can be i) a functional group selected from amine, carbamate, carboxylic acid, carboxylate, maleimide, activated esters, N-hydroxysuccinimidyl, hydrazines, hydrazids, hydrazones, azide, alkyne, aldehydes, thiols, and protected groups thereof for conjugation to a molecule or biomolecule; or ii) a conjugated organic dye or biomolecule. In the above, $R^a$ is a substituted acyl group $-C(O)-CH(NH_2)-CH_2CH_2CH_2CH_2NH_2$, wherein the amines are Boc protected.

In certain aspects, the macromer of formula I has the following formula:

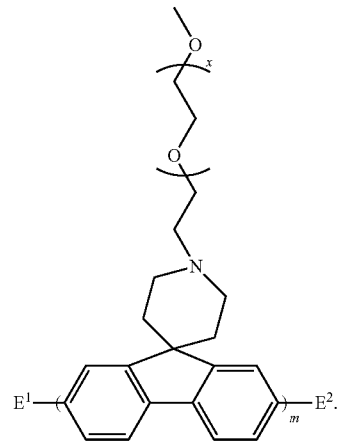

In certain aspects, the value of m is 1-50 or m is 1-15 such as 1, 2, 3, 4, 5, 6, 7, 8, 9, 10, 11, 12, 13, 14 or 15 and the value of x is 11. In one aspect, $E^1$ is hydrogen and $E^2$ is a N-hydroxysuccinimidyl group.

In certain aspects, the macromer of formula I has the following formula:

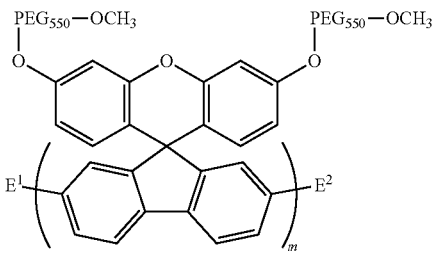

wherein the value of m is 1-50 such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 49, or 50. In one aspect, $E^1$ is hydrogen and $E^2$ is a N-hydroxysuccinimidyl group. In the above, the $C_6$ heterocyclyl group is an optionally substituted tetrahydropyranyl such as a xanthenyl.

In certain aspects, the macromer of formula I has the following formula:

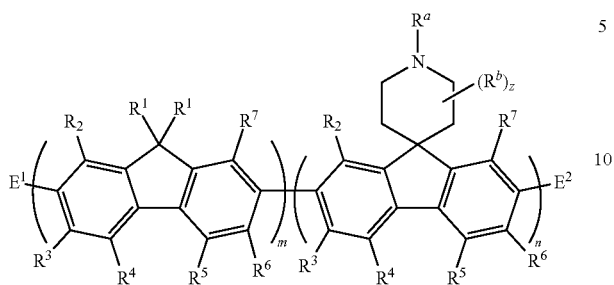

wherein the value of m and n is independently 1-50.

In certain aspects, the macromer of formula I has the following formula:

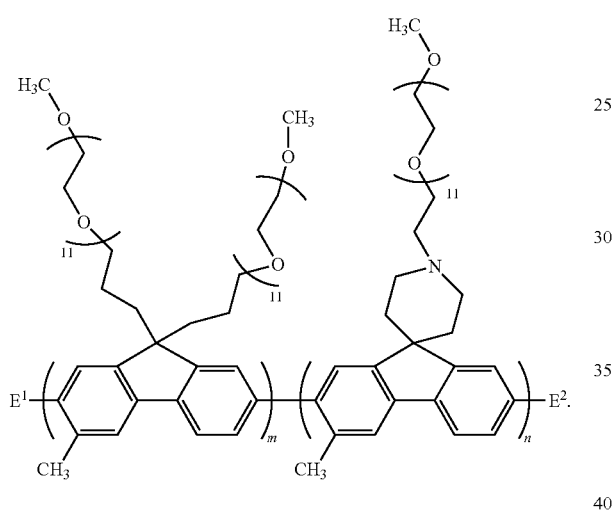

In certain aspects, m is 1-15 and n is 1-15. In one aspect, $E^1$ is hydrogen and $E^2$ is a N-hydroxysuccinimidyl group.

In certain aspects, the macromer of formula I has the following formula:

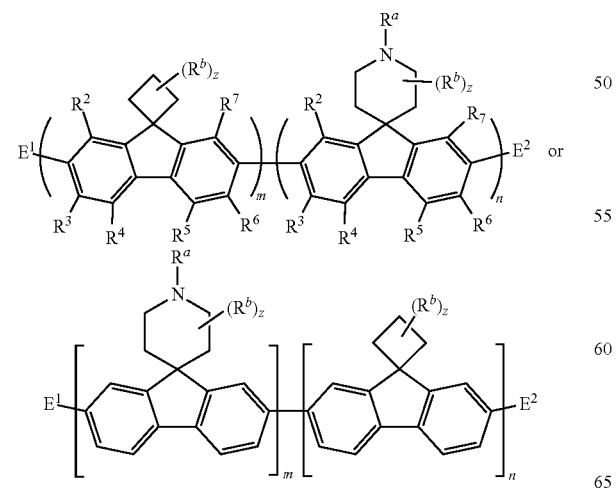

wherein m is 1 to 50 and n is 1 to 50;

$R^a$ is a member selected from the group consisting of hydrogen, an optionally substituted $C_1$-$C_{18}$ alkyl, an optionally substituted $C_1$-$C_{18}$ alkoxy, optionally substituted $C_6$-$C_{18}$ aryl, optionally substituted $C_4$-$C_{18}$ acyl, optionally substituted $C_4$-$C_{18}$ acyloxy, a water solubilizing group, ethylene oxide oligomers, ethylene oxide polymer, and a functional group for conjugation to a molecule or biomolecule;

wherein $R^b$ is a member selected from the group consisting of hydrogen, an optionally substituted $C_1$-$C_{18}$ alkyl, an optionally substituted $C_1$-$C_{18}$ alkoxy, an optionally substituted $C_6$-$C_{18}$ aryl, an optionally substituted $C_4$-$C_{18}$ acyl, an optionally substituted $C_4$-$C_{18}$ acyloxy, a water solubilizing group, ethylene oxide oligomers, ethylene oxide polymer or a site for conjugation; and z is a value of 0 to 4, such as 0, 1, 2, 3, or 4.

In certain aspects, the macromer of formula I has the following formula:

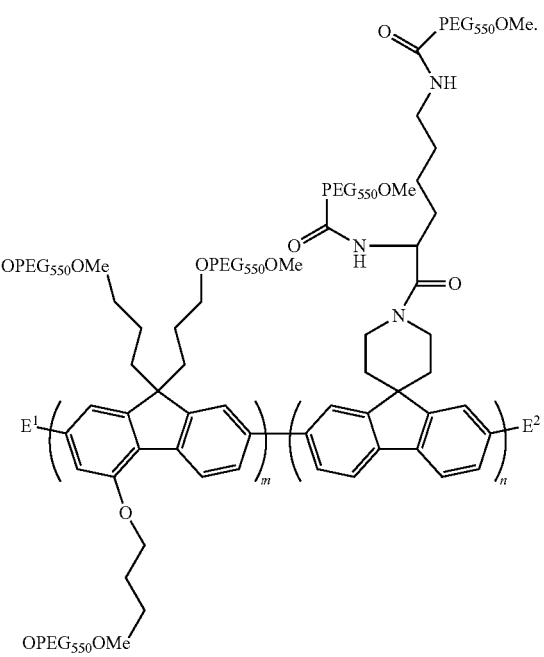

wherein m is 1 to 50 and n is 1 to 50. For example, m is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. The value n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In one aspect, m is 30 and n is 3 and $E^1$ and $E^2$ are each optionally substituted aryl such as an optionally substituted phenyl.

In certain aspects, the macromer of formula I has the following formula:

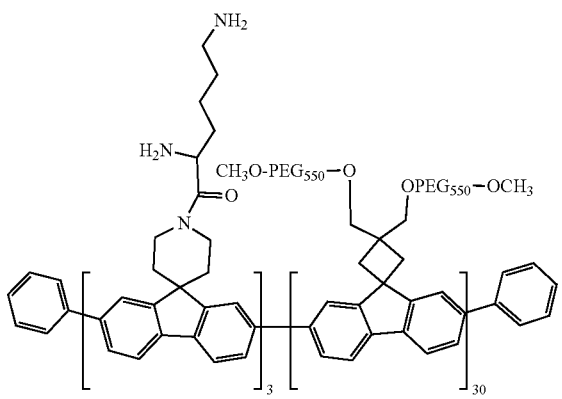

wherein the value of m is 3 and n is 30 and $E^1$ and $E^2$ are each aryl such as phenyl. In an alternative embodiment, m is 1 to 50 and n is independently 1 to 50. For example, m is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. The value n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. A skilled artisan will appreciate either or both of the free amine groups can be used for conjugation to for example, a dye, a biomolecule or alternatively, a water soluble group. In the above, $R^a$ in monomer m is a diamino substituted acyl group i.e., —C(O)—CH (NH$_2$)—CH$_2$CH$_2$CH$_2$CH$_2$NH$_2$. For monomer n, z is 2 and $R^b$ is an ethylene oxide oligomer.

In certain aspects, the ratio of m to n (m:n) is 1:50; 1:45; 1:40; 1:35; 1:30; 1:25; 1:20; 1:15; 1:10; 1:5; or 1:1. In certain other aspects, the ratio of m to n (m:n) is 50:1; 45:1; 40:1; 35:1; 30:1; 25:1; 20:1; 15:1; 10:1; 5:1; or 1:1.

In certain aspects, the molecular weight ($M_n$) is about 5000 to about 60,000. For example, the molecular weight is about 5 kDa, 6 kDa, 7 kDa, 8 kDa, 9 kDa, 10 kDa, 11 kDa, 12 kDa, 13 kDa, 14 kDa, 15 kDa, 16 kDa, 17 kDa, 18 kDa, 19 kDa, 20 kDa, 21 kDa, 22 kDa, 23 kDa, 24 kDa, 25 kDa, 26 kDa, 27 kDa, 28 kDa, 29 kDa, 30 kDa, 31 kDa, 32 kDa, 33 kDa, 34 kDa, 35 kDa, 36 kDa, 37 kDa, 38 kDa, 39 kDa, 40 kDa, 41 kDa, 42 kDa, 43 kDa, 44 kDa, 45 kDa, 46 kDa, 47 kDa, 48 kDa, 49 kDa, 50 kDa, 51 kDa, 52 kDa, 53 kDa, 54 kDa, 55 kDa, 56 kDa, 57 kDa, 58 kDa, 59 kDa or 60 kDa.

In certain aspects, the macromer of formula I has the following formula:

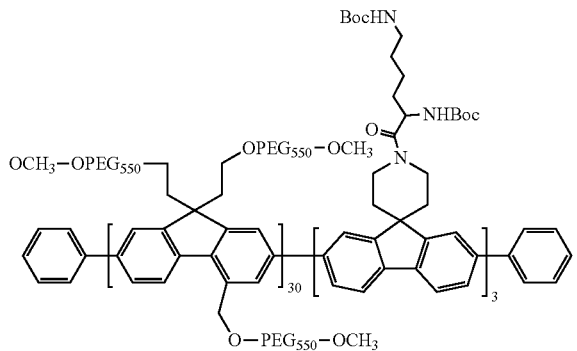

wherein m is 30 and n is 3 and $E^1$ and $E^2$ are each aryl such as phenyl. In an alternative embodiment, m is 1 to 50 and n is 1 to 50. For example, m is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. The value n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. The Boc protecting group can be removed prior and a site for conjugation to a biomolecule can be installed, or alternatively, for a water soluble group.

In certain aspects, the macromer of formula I has the following formula:

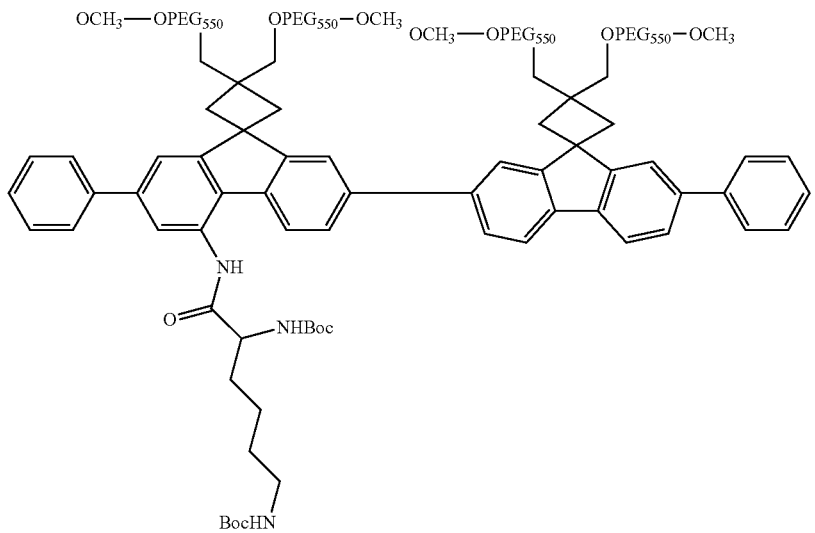

wherein m is 30 and n is 3 and $E^1$ and $E^2$ are each aryl such as phenyl. In an alternative embodiment, m is 1 to 50 and n is 1 to 50. For example, m is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. The value n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. The Boc protecting groups can be removed prior to conjugation to a biomolecule or a water solubilizing group installed.

When linking a biomolecule having a carboxylic acid group for attachment to an amine containing macromer, the carboxylic acid can first be converted to a more reactive form using an activating reagent, to form for example, a N-hydroxy succinimide (NHS) ester or a mixed anhydride. The amine-containing macromer is treated with the resulting activated acid to form an amide linkage. One of skill in the art will recognize that alternatively, the NHS ester can be on the macromer and the amine can be on the biomolecule.

As is known in the art, moieties comprising a free amino group, a free carboxylic acid group, or a free sulfhydryl group provide useful reactive groups for biomolecule conjugation. For example, a free amino group can be conjugated to proteins via glutaraldehyde cross-linking, or via carbodiimide cross-linking to available carboxy moieties on the protein. Also, a linker with a free sulfhydryl group can be conjugated to proteins via maleimide activation of the protein, e.g., using sulfosuccinimidyl-4-(N-maleimidomethyl)cyclohexane-1-carboxylate (Sulfo-SMCC), then linkage to the sulfhydryl group. Alkyl halides react with amines and thiols to make alkylamines and thioethers, respectively.

In certain aspects, the macromer of formula I has the following formula:

used for conjugation to for example, a biomolecule or a water soluble group installed.

In certain aspects, the macromers (i.e., polymers) of formula I can range in size, depending on the polymerization conditions, catalysts, and types and amounts of monomers utilized in the polymerization reaction. For example, the macromers (i.e., polymers) can have a number average molecular weight ($M_n$) of about 5,000 to about 100,000. Macromers with $M_n$ of about 30,000 to about 70,000 are water-soluble and are not prone to aggregation in aqueous medium. Typically macromers of the invention have a narrow range of molecular weights. For example, the polydispersity of the macromers of formula I can be expressed in terms of a polydispersity index (PDI). The PDI can be calculated using the equation $PDI=M_w/M_n$, wherein $M_w$ is the weight-average molar mass and $M_n$ is the number-average molar mass.

In certain aspects, macromers described herein can have a PDI ranging from about 1.2 to 2.2 such as 1.2, 1.3, 1.4, 1.5, 1.6, 1.7, 1.8, 1.9, 2.0, 2.1, or 2.2, wherein a polymer having a PDI from about 1.0 to about 1.5 can be considered monodisperse. In certain embodiments, the macromers of formula I have a molecular weight (Mn) of about 42,000-70,000 Daltons, with narrow distribution of PDI<2.0.

In certain aspects, the macromers of formula I are soluble in common organic solvents such as for example, THF, dichloromethane, methanol, toluene, and the like. Certain macromers described herein also are soluble in aqueous media, such as, for example, water, saline, buffered aqueous solutions such as borate, carbonate, or phosphate buffers and the like. Typically, the macromers of formula I exhibit aqueous solubility up to 1.0 mg/mL in water or buffers such as PBS.

In certain aspects, the macromers of formula I include a conjugated segment. Extended conjugation within the poly-

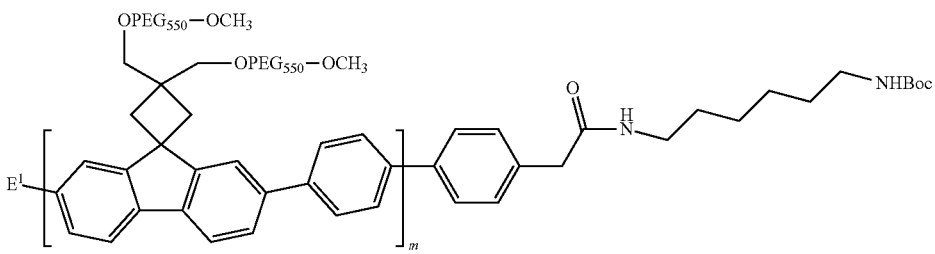

wherein m is 1 to 50. For example, m is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In certain aspects, $E^1$ is a member selected from the group consisting of hydrogen, halogen, alkynyl, optionally substituted aryl, optionally substituted heteroaryl, halo, substituted aryl, boronic acid substituted aryl, boronic ester substituted aryl, boronic ester, boronic acid, optionally substituted fluorene and aryl or heteroaryl substituted with one or more pendant chains terminated with: i) a functional group selected from amine, carbamate, carboxylic acid, carboxylate, maleimide, activated esters, N-hydroxysuccinimidyl, hydrazines, hydrazids, hydrazones, azide, alkyne, aldehydes, thiols, and protected groups thereof for conjugation to a molecule or biomolecule; or ii) a conjugated organic dye or biomolecule. A skilled artisan will appreciate that the free amine groups (the Boc is removed) can be mer backbone allows the macromers to exhibit fluorescence emission upon excitation at an appropriate wavelength of light. In certain instances, an aromatic group or heteroaromatic group such as A, B and/or C when present complete or comprise π-conjugated backbone. Fluorescent macromers that include a conjugated segment can have a tunable photophysical property in the near ultraviolet (UV) to far infrared (IR) range. Because the disclosed macromers exhibit a host of favorable optical properties, this class of macromers are useful for biological assays requiring a high level of sensitivity.

In certain aspects, the macromers of formula I emit bright, visible light upon UV excitation and typically absorb light having a wavelength of about 500 nm or less (e.g., about 300 nm to about 500 nm). In certain embodiments, the disclosed polymers absorb light having a wavelength of about 350 nm to about 450 nm; or about 380 nm to about 410 nm. Macromers that can absorb light having a wavelength of about 405 nm can be effectively irradiated using a violet laser. Upon irradiation at an appropriate wavelength, the macromers can emit light having a wavelength of greater than about 400 nm; e.g., about 400 to about 800 nm; or about 400-780 nm. Incorporation of additional aromatic monomer residues (A, B, and/or C e.g., benzodithiazole, phenyl or thiophenyl) in the macromer backbone can alter the electronic properties of the macromer and shift the excitation and emission wavelength of the copolymer.

In certain aspects, the macromers of formula I can exhibit one or more of the following properties or characteristics: fluorescence emission upon excitation at an appropriate wavelength of light (e.g., below about 500 nm); emission of light having a wavelength of greater than about 400 nm; an extinction coefficient of greater than about $2\times10^6$ cm$^{-1}$ M$^{-1}$ in water; and a number average molecular weight (Mn) of about 5,000 to about 70,000, such as 5,000, to about 10,000, or to 15,000, or to 20,000, or to 25000, or to 30,000, or to 35,000, or to 40,000, or to 45,000, or to 50,000, or to 55,000, or to 60,000, or to 65,000, or to 70,000.

In certain aspects the macromers of formula I only absorb light and exhibit no emission, and typically absorb light having a wavelength of about 500 nm or less, and have a number average molecular weight (Mn) of about 5,000 to about 70,000, such as 5,000 to about 10,000, or to 15,000, or to 20,000, or to 25,000, or to 30,000, or to 35,000, or to 40,000, or to 45,000, or to 50,000, or to 55,000, or to 60,000, or to 65,000, or to 70,000.

B. Methods Utilizing the Compounds

In one aspect, the macromers of the present invention are used in FRET assay 100 such as the one shown in FIG. 1. For example, a biomolecule such as an antibody 110 labeled with a dye 125 is reacted with a macromer 131 of the present invention. The macromer of the present invention reacts with the antibody 110 in a covalent manner to produce an antibody with the attached dye and macromer. In this assay method, energy is transferred between a donor fluorophore and an acceptor fluorophore if the two fluorophore are in close proximity to the each other. Excitation of the "donor" i.e., macromer 131 by an energy source (e.g. UV light) produces an energy transfer to the "acceptor" i.e., dye 125 if the two fluorophores are within a given proximity. In turn, the acceptor emits light characterized by the star like depiction of 125 at its characteristic wavelength.

Advantageously, interaction or binding between a macromer of the invention and dye-labeled antibodies increases detection sensitivies, for example, of a biomolecule target or analyte. In another aspect, covalently attaching a macromer of the invention to a dye, biomolecule (e.g., an antibody complex), offers several advantages, including reduced background and/or improved energy transfer. In the case of direct linkage to a biomolecule, biorecognition events, rather than nonspecific macromer interaction or binding events, govern macromer presence. In this manner, nonspecific binding of macromers to biomolecules can be eliminated, reducing background emission resulting from unbound or uncomplexed conjugated macromer molecules in the reaction mixture.

Figure 2:
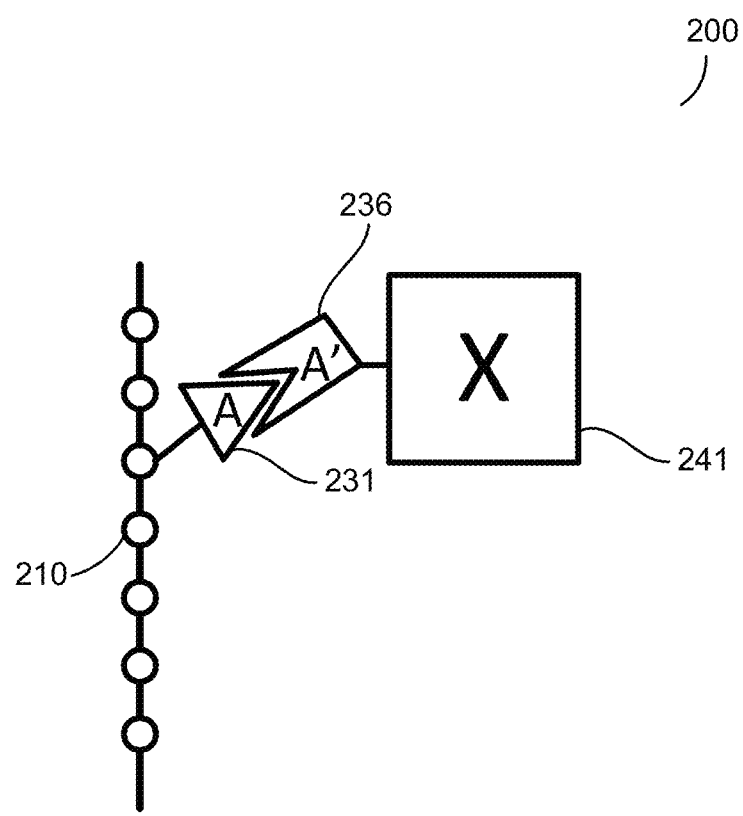
FIG. 2 illustrates a schematic of a bioconjugated macromer of one embodiment of the invention.

Turning now to FIG. 2, this schematic 200 illustrates a conjugated macromer 210 of one embodiment of the invention. In certain aspects, the macromer 210 of the invention is conjugated to an affinity ligand, i.e., a biomolecule that has an affinity for another biomolecule. FIG. 2 illustrates a class of materials according to the invention in which a macromer 210 is linked to for example, a dye, biomolecule, or biomolecule/dye complex i.e., "X" 241. Linking to the macromer can be via a first functionality 231 (A) on the macromer that serves as a bioconjugation site capable of covalently linking with a second functionality linker 236 (A') linked to a biomolecule and/or dye "X" 241. This arrangement can fix the distance between the macromer 210 and X 241, thereby ensuring only specific interactions between the macromer 210 of the invention and the moiety X 241. It is envisioned that a biomolecule component 241 in these embodiments can be any of the various biomolecules described herein, including, but not limited to, an antibody, protein, an affinity ligand, an enzyme, nucleic acid, or the like.

Advantageously, linker "A" 231 can be attached anywhere on the macromer, including at terminal positions of the macromer, internally on a repeating subunit, in between repeating subunits, or any combination thereof. Likewise, linker "A'" 236 can be linked to any suitable group on a biomolecule and/or dye X. The linking chemistry for A and A' (231, 236) to their respective macromer or biomolecule (or dye or dye-labeled biomolecule) can include, but is not limited to, complementary reactive groups such as maleimide/thiol; thiol/thiol; pyridyldithiol/thiol; succinimidyl iodoacetate/thiol; N-succinimidylester (NHS ester), sulfodicholorphenol ester (SDP ester), or pentafluorophenyl-ester (PFP ester)/amine; bissuccinimidylester/amine; imidoesters/amines; hydrazine or amine/aldehyde, dialdehyde or benzaldehyde; isocyanate/hydroxyl or amine; carbohydrate-periodate/hydrazine or amine; diazirine/aryl azide chemistry; pyridyldithiol/aryl azide chemistry; alkyne/azide; carboxy-carbodiimide/amine; amine/Sulfo-SMCC (Sulfosuccinimidyl 4-[N-maleimidomethyl]cyclohexane-1-carboxylate)/thiol; and amine/BMPH (N-[β-Maleimidopropionic acid] hydrazide•TFA)/thiol. Those of skill in the art will know of other complementary coupling chemistries useful for the present invention.

In certain aspects, the "X" moiety 241 in FIG. 2 in this context can be, but is not limited to, a dye, fluorescence protein, nanomaterial (e.g., Quantum Dot), chemluminescence-generating molecule, a conjugate between dye and chemluminescence-generating molecule, a conjugate between fluorescence protein and chemluminescence-generating molecule, a conjugate between nanomaterial (e.g., Quantum Dot) and chemluminescence-generating molecule, streptavidin, avidin, enzyme, substrate for an enzyme, substrate analog for an enzyme, receptor, ligand for a receptor, ligand analog for a receptor, DNA, RNA, modified nucleic acid, DNA aptamer, RNA aptamer, modified nucleic aptamer, peptide aptamer, antibody, antigen, phage, bacterium, or conjugate of any two of the items described above.

In certain aspects, the present invention provides a method for detecting an analyte in a sample, the method comprising:

(a) combining the sample and a macromer of the invention;

(b) exciting the macromer with light; and (c) detecting fluorescence from the macromer, thereby detecting the analyte.

Figures 3A, 3B, 3C, 3D:
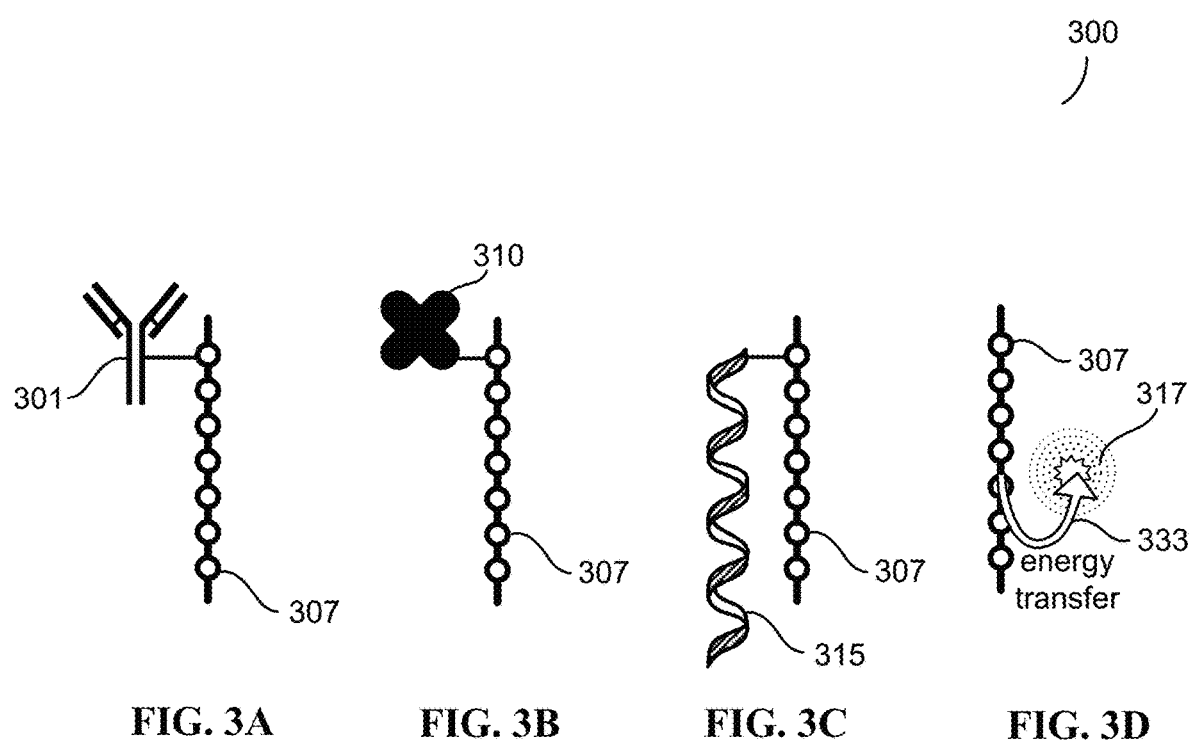
FIGS. 3A-D illustrates an exemplary macromer which is conjugated to an antibody (FIG. 3A); avidin (FIG. 3B); a nucleic acid (FIG. 3C); and a dye (FIG. 3D).

FIG. 3 is a schematic 300 that depicts an exemplary macromer that is conjugated to, for example, an antibody (A); avidin (B); a nucleic acid (C); and a dye (D). In certain aspects, the invention includes the use of these conjugated macromers as direct labels. In certain aspects, as is shown in FIG. 3A, a macromer 307 is conjugated to an antibody 301, which can be, for example, a primary or secondary antibody. The macromer conjugated to the antibody can be used as a direct reporter, for example, in a bioassay (e.g., an immunoassay). Excitation of the macromer with light can result in macromer emission, indicating the presence of the antibody in the assay or assay solution.

FIGS. 3B and 3C further exemplify the use of conjugated macromers of the invention as biomolecule labels capable of detecting specific targets, analytes and target-associated biomolecules. FIG. 3B depicts a macromer 307 conjugated to avidin (e.g., streptavidin, neutraAvidin, etc.; 310), capable of binding to biotin-modified molecules, biomolecules, or substrates. FIG. 3C depicts a nucleic acid (DNA, RNA, PNA, and the like) 315 conjugate that includes a macromer 307 of the invention covalently linked to a nucleic acid 315, which conjugate is capable of hybridizing to target nucleic acids that contain complementary nucleic acid sequences. Linkage or conjugation of fluorescent macromers to a molecule capable of recognizing a target biomolecule, analyte or target-associated molecule provides a direct means of detection. In other aspects, the signals generated from excitation of the macromer are not modulated by other assay components except those that are directly conjugated to the macromer. In such embodiments, the macromer acts directly as a fluorescent label.

In another aspect, as is shown in FIG. 3D, a macromer 307 of the invention is labeled with a dye 317, for example, a chromophore. In this embodiment, the conjugated macromer 307 can act as a donor and the dye 317 can act as an acceptor in an energy transfer process. Here, the conjugated macromer can act as a light harvester, and excitation of the conjugated macromer is followed by the channeling of the excitations to the dye via an energy transfer process such as fluorescence resonance energy transfer (FRET) 333. This results in amplified dye emission (as compared to direct excitation of the dye). The fluorescence of the donor conjugated macromer, in one embodiment, can be quenched (e.g., >90% quenching).

A wide variety of dyes can be used in the present invention. In some aspects, a functional group is used to label the dye to form a fluorescence resonance energy transfer (FRET) pair. Excitation wavelengths are preferably between about 200-900 nm, and the emission wavelength is preferably around about 200-900 nm. Exemplary fluorescent dyes include, but are not limited to, fluorescein, 6-FAM, rhodamine, Texas Red, tetramethylrhodamine, a carboxyrhodamine, carboxyrhodamine 6G, carboxyrhodol, carboxyrhodamine 110, Cascade Blue, Cascade Yellow, coumarin, Cy2®, Cy3®, Cy3.5®, Cy5®, Cy5.5®, Cy-Chrome, phycoerythrin, PerCP (peridinin chlorophyll-a Protein), PerCP-Cy5.5, JOE (6-carboxy-4,5-dichloro-2,7-dimelhoxyfluorescein), NED, ROX (5-(and-6)-carboxy-X-rhodamine), HEX, Lucifer Yellow, Marina Blue, Oregon Green 488, Oregon Green 500, Oregon Green 514, Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-$Br_2$, BODIPY® 530/550, BODIPY® 558/568, BODIPY® 564/570, BODIPY® 576/589, BODIPY® 581/591, BODIPY® 630/650, BODIPY® 650/665, BODIPY® R6G, BODIPY® TMR, BODIPY® TR, conjugates thereof, and combinations thereof. Exemplary lanthanide chelates include europium chelates, terbium chelates and samarium chelates. Those of skill in the art will know of other dyes useful top practice the present invention.

In certain instances, the dye can be a quencher dye. Quencher dyes include, but are not limited to (absorbstion max), Dabcyl (453), QSY35 (475), BHQ-0 (495), Eclipse (530), BHQ-1 (534), QSY 7 (560), QSY 9 (562), BHQ-2 (579), ElleQuencher (630), Iowa Black (651), QSY 21 (661), and BHQ-3 (672). In certain instances, when $R^2$, $R^3$, $R^4$, $R^5$, $R^6$, and $R^7$ is independently selected from nitro, cyano, or an optionally substituted amino, the macromer will be a quencher dye.

Figure 4C:
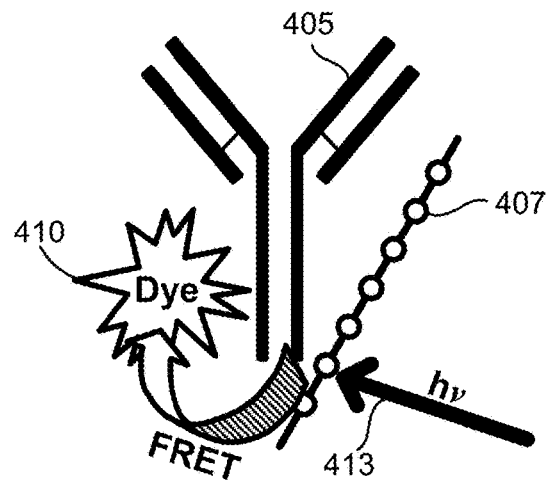
Figure 4C:
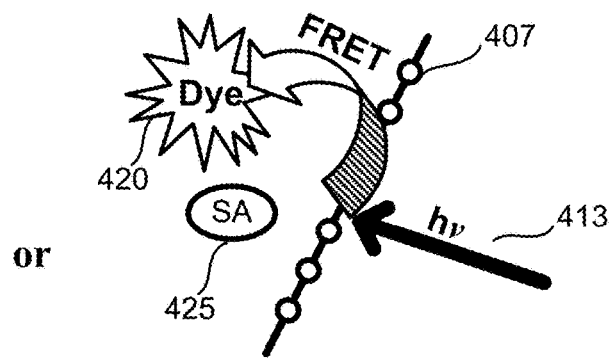
Figure 4C:
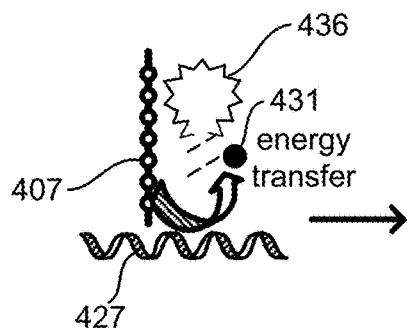
Figure 4C:
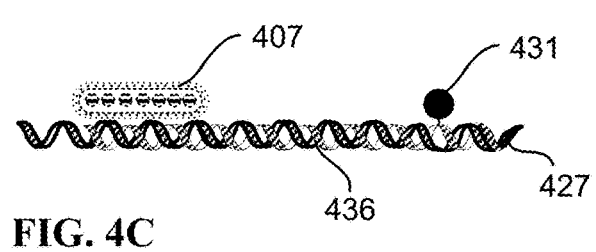
Figure 4D:
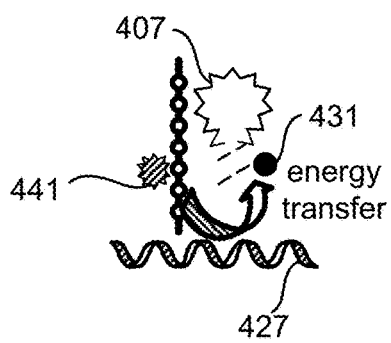
Figure 4D:
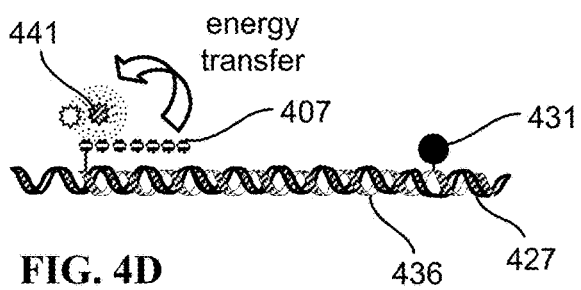
Figure 5A:
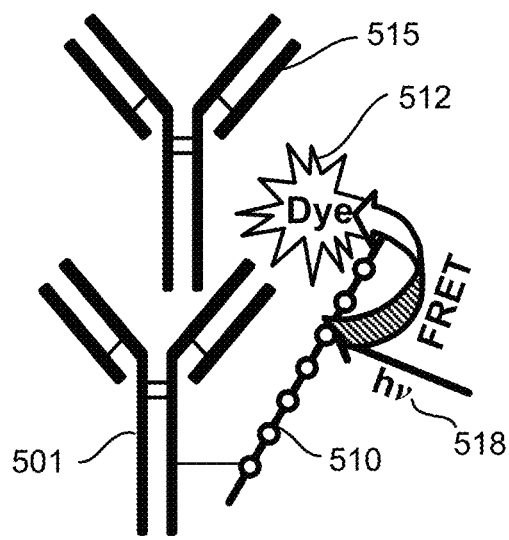
FIGS. 5A-D illustrate a schematic that depicts various methods of assaying for a target biomolecule or analyte.
Figure 5B:
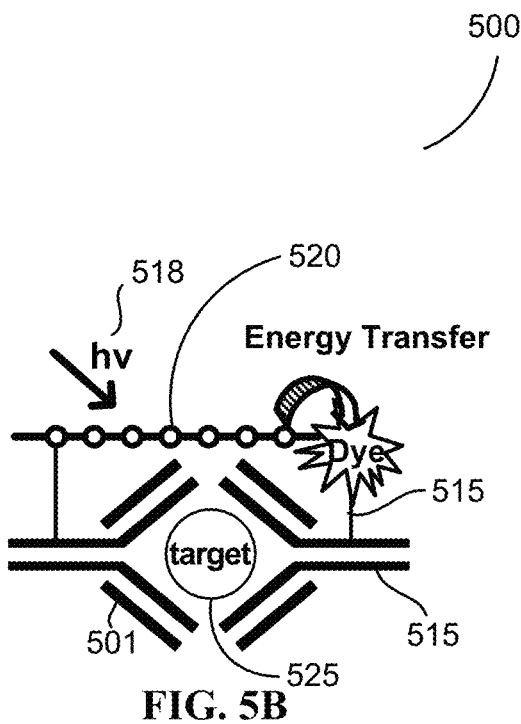
Figure 5C:
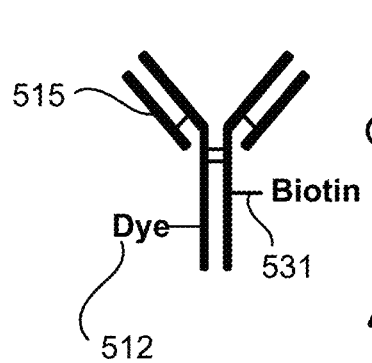
Figure 5D:
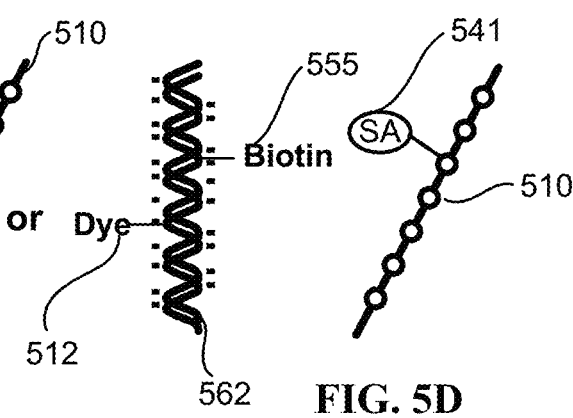

FIG. 4(A) illustrates an antibody 405 labeled with a dye 410 and a macromer 407 according to the invention for use in a FRET assay with UV light 413; FIG. 4(B) illustrates streptavidin (SA) 425 labeled with a dye 420 and labeled with a macromer 407 according to the invention for use in a FRET assay with UV light 413; FIG. 4(C) illustrates a nucleic acid probe sequence 427 labeled with a quencher molecule 431 conjugated to a macromer 407 of the invention, nucleic acid probe sequence 436 hybridizes with sequence 427; FIG. 4(D) illustrates a nucleic acid probe sequence 427 labeled with a quencher molecule 431 and macromer 407, with an appended dye 441 tandem complex. The nucleic acid probe sequence 427 hybridizes to sequence 436.

In the case of direct linkage of a macromer of the invention to a dye (FIG. 3D) or biomolecule/dye complex (as exemplified in FIG. 4), donor-acceptor distances can be fixed, rather than dependent on the strength of interaction or binding, and energy transfer efficiency can be significantly increased. This has significant consequences in the context of improving dye signaling (or quenching) and reducing background fluorescence associated with donor-acceptor cross-talk. Cross-talk in this case refers to the overlap between the macromer (donor's) and dye's (acceptor's) emission peaks. As will be appreciated, macromers that bind non-specifically at distances too great for energy transfer can contribute to the background fluorescence (or cross-talk). Shorter (fixed) distances between the donor and acceptor can thus not only facilitate direct dye amplification, but also can greatly quench the donor emission.

FIG. 5 illustrates a schematic that depicts various methods of assaying for a target biomolecule, analyte or target associated biomolecule. For example, FIG. 5(A) shows a macromer 510 linked to a first antibody 501 bound to a second antibody 515 with a dye 512; FIG. 5(B) illustrates a macromer 520 and dye 512 labeled antibodies recognize a common target 525; FIG. 5(C) illustrates an antibody 515 with a linked dye 512 and biotin 531 and a second bioconjugate of streptavidin 541 with a macromer 510 appended thereto; and FIG. 5(D) illustrates a nucleic acid 562 with a dye 512 and biotin bound 555 thereto and streptavidin 541 with a macromer 510 conjugated thereto.

Figure 6:
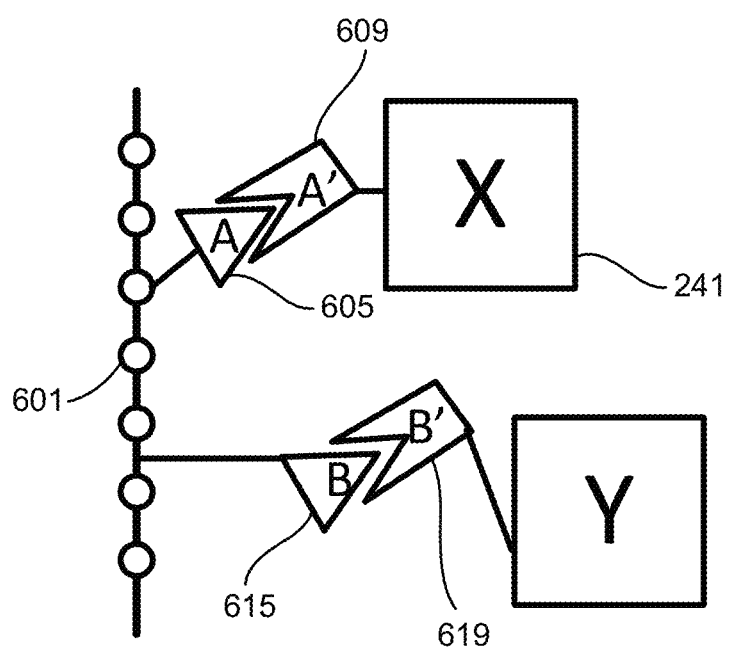
FIG. 6 illustrates a schematic according to the present invention.

Turning to FIG. 6, illustrated therein is a schematic that depicts a first linking site 605 (A) and a second linking site 615(B) within a macromer 601 to append a "X" moiety such as a dye and a "Y" moiety such as an antibody by complementary linker 609 (A') and linker 619 (B'), respectively.

Figure 7A:
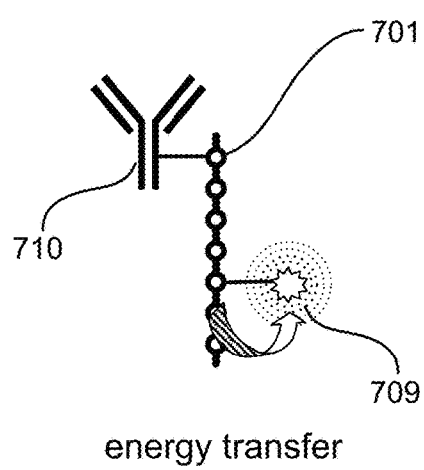
FIGS. 7A-C illustrate various schematic of the invention.
Figure 7B:
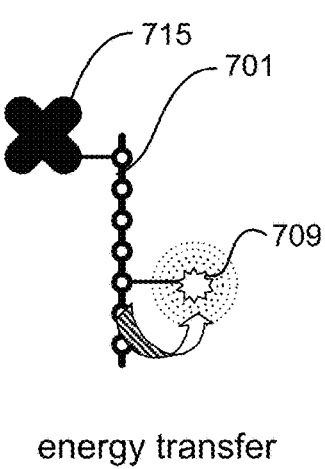
Figure 7C:
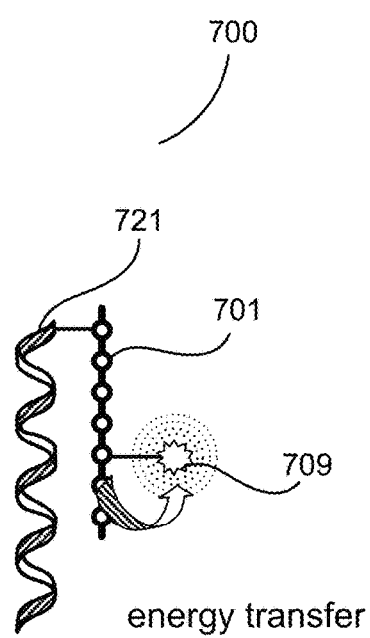

FIG. 7A illustrates a schematic that depicts a macromer 701 with a linked dye 709 and a biomolecule 710 and resulting energy transfer; FIG. 7B illustrates a macromer 701 with a conjugated streptavidin 715 and a linked dye 709; and FIG. 7C illustrates a macromer 701 conjugated to a nucleic acid 721 and a dye 709.

FIG. 8 illustrates a schematic that depicts indirect associations with macromers linked to a biomolecule. For example, FIG. 8A shows a biotinylated antibody 815 interacting with a covalent conjugate 804 of a macromer 801; FIG. 8B shows a biotinylated antibody 815 interacting with a moiety 809 linked to a macromer 801 having a linked dye 812; FIG. 8C shows a biotinylated nucleic acid 822 interacting with a covalent moiety 809 of a macromer; FIG. 8D shows a biotinylated nucleic acid 822 bound to a linked moiety 809 of a macromer 801 having a linked dye 812; FIG. 8E shows a nucleic acid 822 with digoxygenin moiety 831 interacting with a covalently linked antibody of the macromer 801; and FIG. 8F shows a nucleic acid 822 with digoxygenin moiety 831 and a covalent antibody to a macromer dye 812 tandem complex.

Figure 9A:
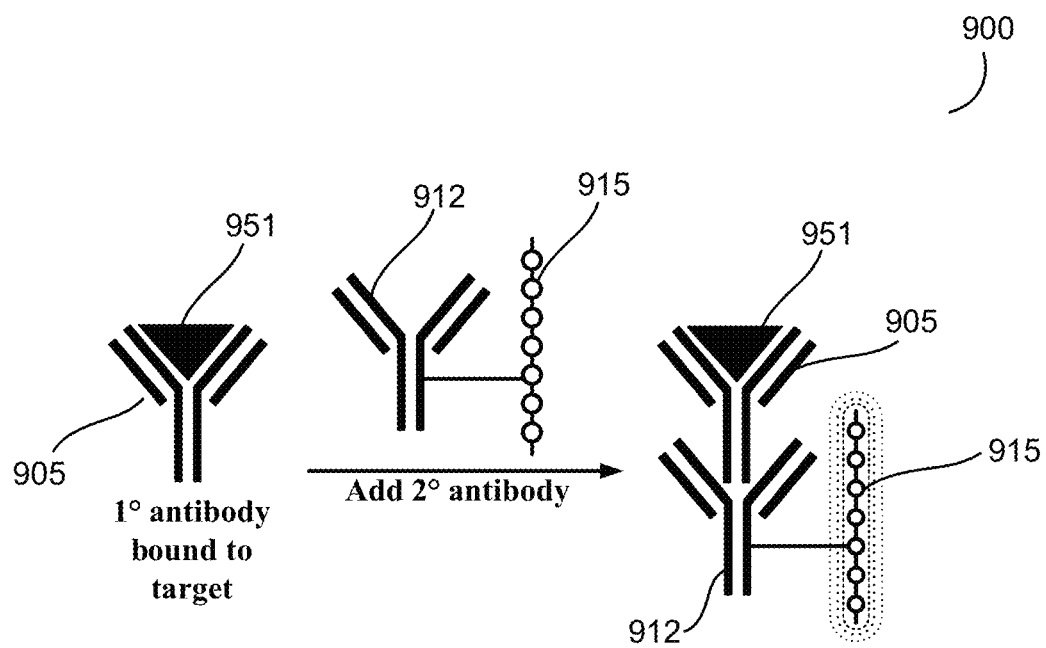
FIGS. 9A-B show assay embodiments of the invention.
Figure 9B:
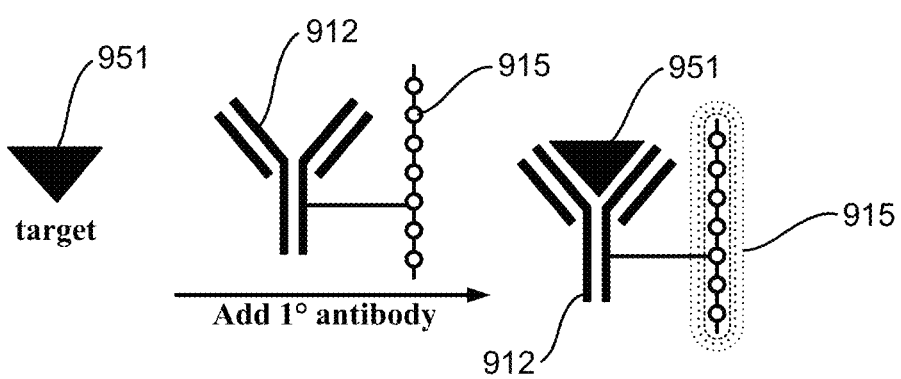

FIG. 9A shows a primary antibody 905 bound to an analyte 951 wherein a secondary antibody 912 having a macromer appended thereto 915 is added. In FIG. 9B, a target analyte 951 binds to a primary antibody 912 with a linked macromer 915.

Figure 10A:
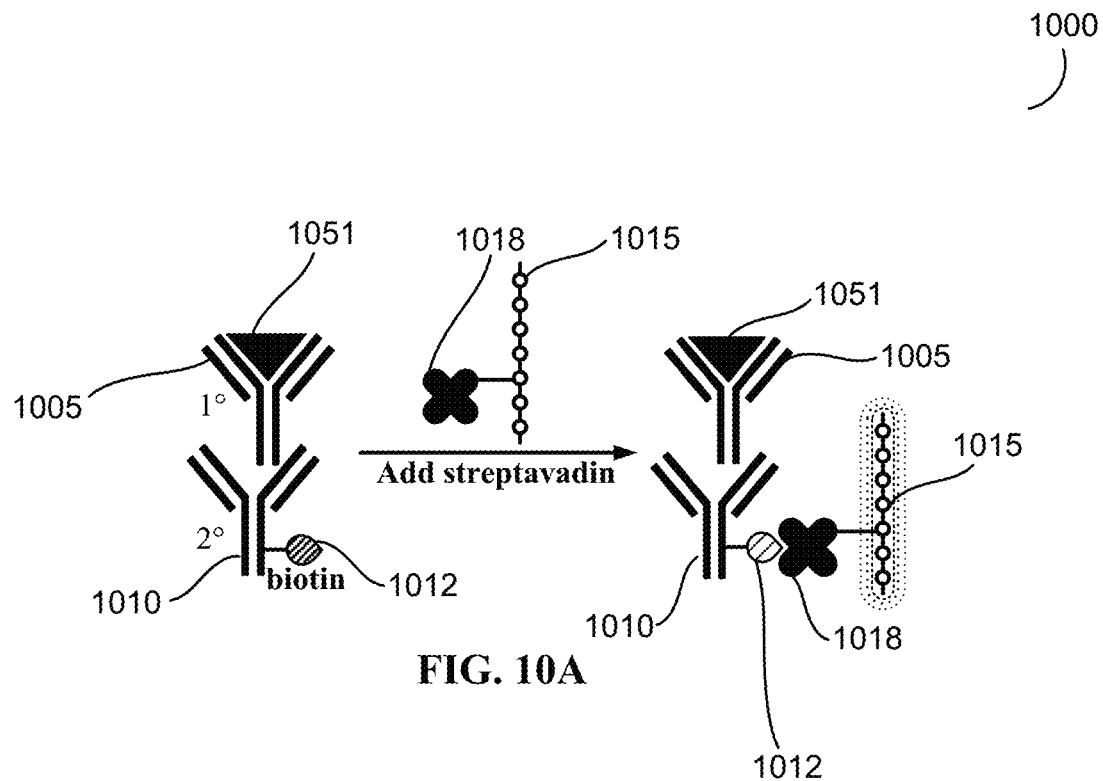
FIGS. 10A-B show sandwich-type complex embodiments.

FIG. 10A shows a sandwich-type complex, wherein a primary antibody 1005 binds an analyte 1051. A secondary antibody with a biotin 1012 is then added. Next, a macromer 1015 with a streptavidin 1018 is added to generate a sandwich complex.

Figure 10B:
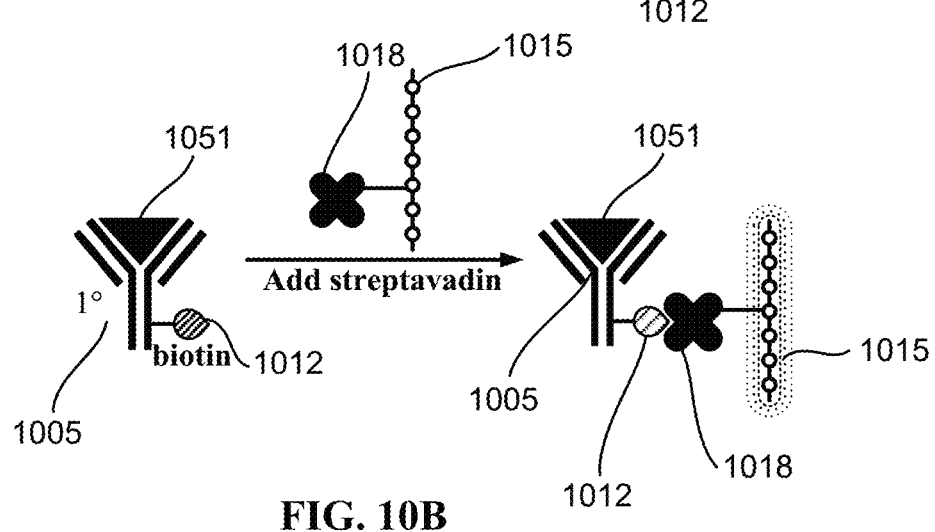

FIG. 10B shows a biotin 1012 labeled primary antibody 1005 with an analyte 1051 bound. A streptavidin 1118 linked to a macromer 1015 is added.

In certain aspects, the present invention provides a method for detecting a target biomolecule in a sample, the method comprising:

providing a sample that is suspected of containing a target analyte;

providing a macromer described herein conjugated to a capture molecule, wherein the capture molecule is capable of interacting with the target analyte;

contacting the sample with the capture molecule and the conjugated macromer under conditions in which the capture molecule can bind to the target analyte if present;

applying a light source to the sample that excites the conjugated macromer; and detecting whether light is emitted from the conjugated macromer.

In certain aspects, the method is performed in vivo. In certain aspects, the sample contains a living cell. In certain aspects, the analyte is a nucleic acid which comprises a genetic point mutation, deletion or insertion relative to a control nucleic acid. In certain aspects, the detection of the nucleic acid indicates the presence of a cancer in the sample.

C. Methods Making the Compounds

In one embodiment, the invention provides a method for synthesizing a compounds as described herein. In certain instances, monomeric units can be derivatized to diboronic esters, which monomers can subsequently be used for polymerization such as, for example, via Suzuki coupling. See *J. Am. Chem. Soc.*, 2014, 136, 14027-14030. Polymeric fluorenes may also be obtained through the use of other reaction schemes involving organometallic catalysis. For example, the Yamamoto reaction uses a nickel (0)-based catalyst for the homo-coupling of aryl halide monomers. Additionally, conjugated polymers can also be synthesized using Stille, Heck, and Sonogashira coupling reactions. See, e.g., Yamamoto et al., *Macromolecules* 25: 1214-1223, 1992; Kreyenschmidt et al., *Macromolecules* 28: 4577-4582, 1995; and Pei et al., *J. Am. Chem. Soc.* 118: 7416-7417, 1996 regarding Yamamoto reaction schemes. See, also, Leclerc, Polym. Sci. Part A: *Polym. Chem.* 39: 2867-2873, 2001 for Stille reaction schemes; Mikroyannidis et al., *J. Polym. Sci. Part A: Polym. Chem.* 45: 4661-4670, 2007 for Heck reaction schemes; and Sonogashira et al., *Tetrahedron Lett.* 16: 4467-4470, 1975 and Lee et al., Org. Lett. 3: 2005-2007, 2001 for Sonogashira reaction schemes.

In certain aspects, the methods of making the macromers of formula I comprise combining a plurality of reactive monomers to form a reaction mixture, wherein a first portion of the reactive monomers bears first reactive groups and a second portion of the monomers bears second reactive groups, wherein the first and second reactive groups are different and capable of reacting with each other to form a polymer. In certain aspects, at least one reactive monomer includes a monomer that is optionally substituted with one or more water-solubilizing groups. The reaction mixture is then subjected to conditions wherein the first and second reactive groups on the monomers react to form a polymer. In some methods, a plurality of monomers bearing suitable polymerizable groups are condensed to produce a macromer that includes a polymer backbone formed of the linked monomer residues.

In certain aspects, various types of polymerization strategies can be employed to couple the polymerizable monomers described herein. As mentioned, one representative method for preparing conjugated macromers described herein involves Yamamoto polymerization of monomers bearing halide functional groups in the presence of a metal catalyst (e.g., nickel).

In certain aspects, the polymerization strategy involves Suzuki polycondensation. The Suzuki reaction is a Pd-catalyzed coupling reaction between an aromatic boronic acid derivative and an aromatic halide that yields the corresponding biphenyl. In general, Suzuki polymerization involves coupling aromatic monomers that are each provided with two reactive functional groups. Appropriate functional groups for Suzuki polymerization include halides (e.g., Br or I) and boron-containing functional groups, such as boronic acid, a boronic ester (e.g., $C_1$-$C_6$ boronic acid ester), a borane group (e.g., $C_1$-$C_6$ borane) and $BF_3$ groups. In one exemplary method, a first reactive dihalide monomer is polymerized with a second monomer having two boron derivative functional groups. In this arrangement the first and the second monomers can be the same to produce a homopolymer or different to produce a copolymer. In a second exemplary method, a monomer having a boron derivative functional group and a reactive halide functional group is polymerized to form a homopolymer. Copolymers can be prepared using such an arrangement by polymerizing together two or more different types of monomers each containing both functionalities.

In certain aspects, a representative Suzuki polymerization reaction involves forming a reaction mixture that includes (a) an aromatic monomer having at least two reactive boron-containing groups and an aromatic monomer having at least two reactive halide functional groups; or (b) an aromatic monomer having one reactive halide functional group and one reactive boron-containing group. The reaction is conducted in a solvent in which the conjugated macromer is soluble. Suitable solvents include water-miscible, polar solvents such as THF, acetone and chloroform. Included in the reaction mixture is a catalytic amount of a catalyst to catalyze the polymerization of the aromatic monomers. The reaction can be catalyzed using a soluble Pd source. Pd (II) salts (e.g., Pd acetate) or Pd (0) complexes such as $Pd(Ph_3P)_4$ are examples of suitable Pd sources that can be used in the methods disclosed herein. The reaction also includes a base in an amount sufficient to convert the reactive boron-containing functional groups into anionic —$BX_3^-$ groups, wherein X is independently F or OH. Suitable bases include inorganic base, such as, for example, alkali metal carbonates or bicarbonates, such as potassium or sodium bicarbonate.

In certain aspects, monomers described herein are polymerized via Suzuki polycondensation to produce a 2,7-linked macromer. For example, dibromo and bis(boronate) 2,7-disubstituted monomers can be polymerized as described herein to yield a poly (2,7-monomer). The polymerization reaction can utilize monomers as described herein, which can optionally bear one or more water-solubilizing groups. Addition of aromatic monomers (e.g., arenes or heteroarenes) bearing suitable polymerizable groups into the reaction mixture can provide copolymers having a backbone that includes linked monomers and aromatic monomer residues. In certain methods, the additional monomers can include optionally substituted arene (e.g., fluorene) or heteroarene groups, thereby forming a copolymer having a polymer backbone comprising residues of arene or heteroarene monomers. In any of the polymerization methods described herein, polymerizable monomers bearing one or more water-solubilizing groups can be used in the polymerization reaction to afford water-soluble polymers and copolymers.

Figure 11:
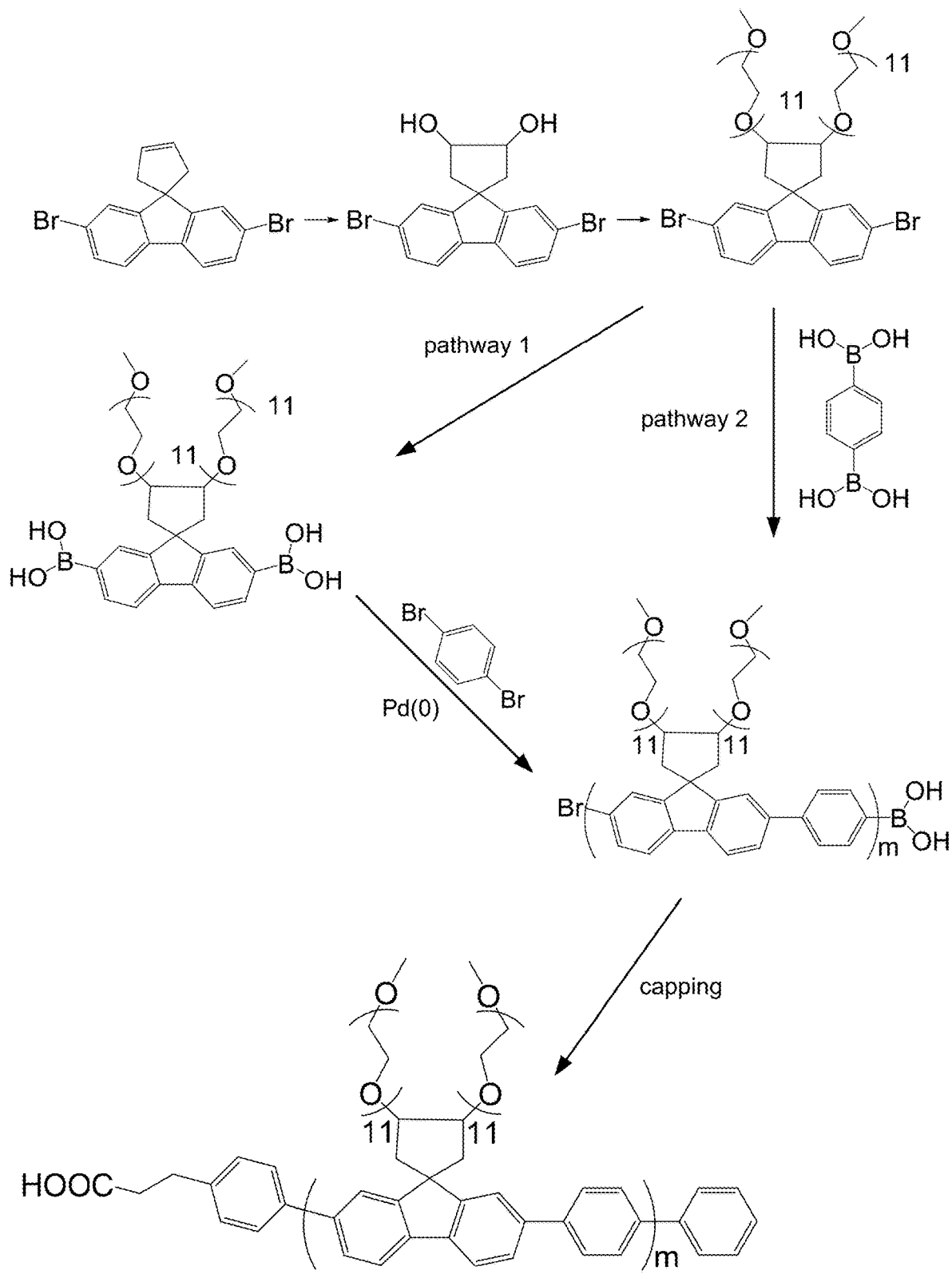
FIG. 11 illustrates a schematic showing Suzuki polycondensation of making macromers of the present invention.
Figure 12:
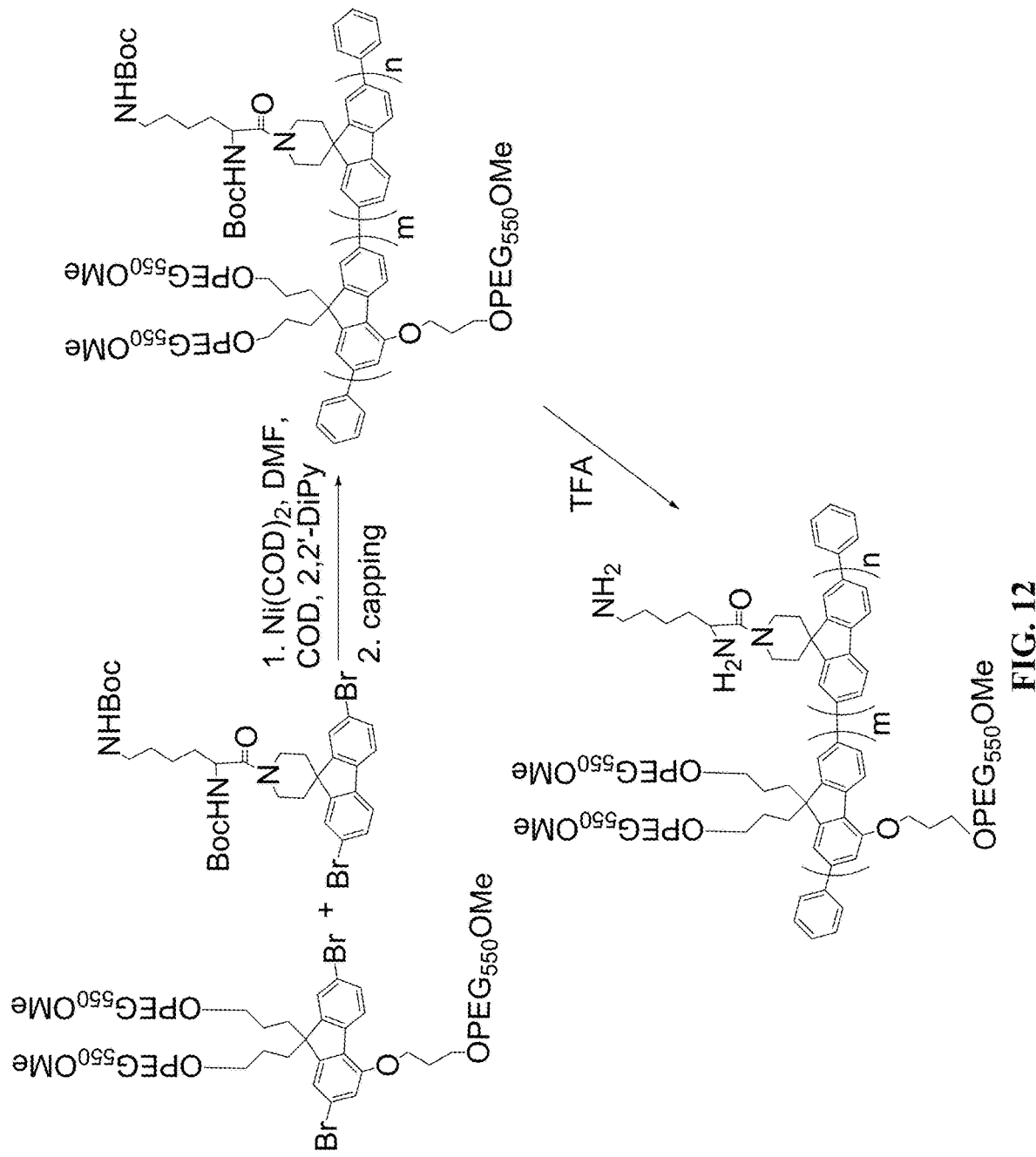
FIG. 12 illustrates a schematic showing Yamamoto polycondensation of making macromers of the present invention.

FIG. 11 illustrates a schematic showing Suzuki polycondensation of making macromers of the present invention. FIG. 12 illustrates a schematic showing Yamamoto polycondensation of making macromers of the present invention.

In certain aspects, the macromers of formula I are prepared using monomers which has the following general formula:

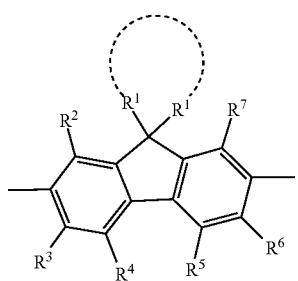

Some exemplary monomers for use in preparing macromers of the invention are as follows:

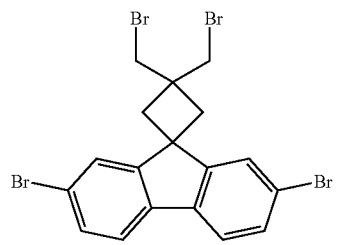 [SMILES: BrCC1(CBr)CC2(C1)c1cc(Br)ccc1-c1ccc(Br)cc12]

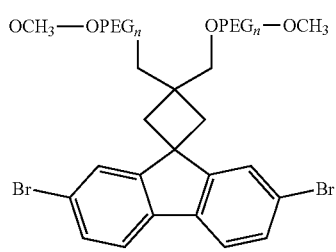

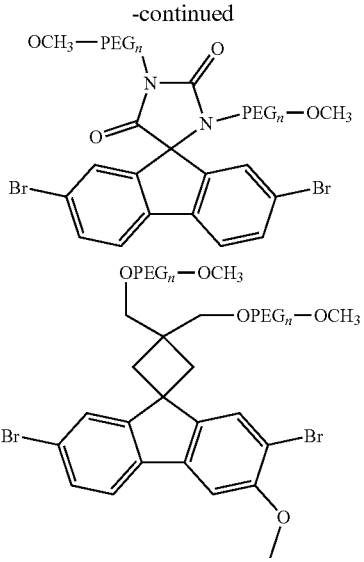

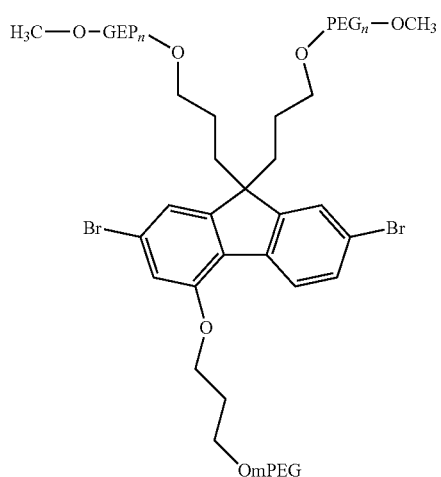

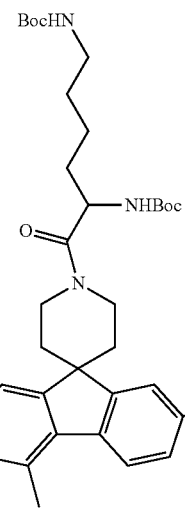

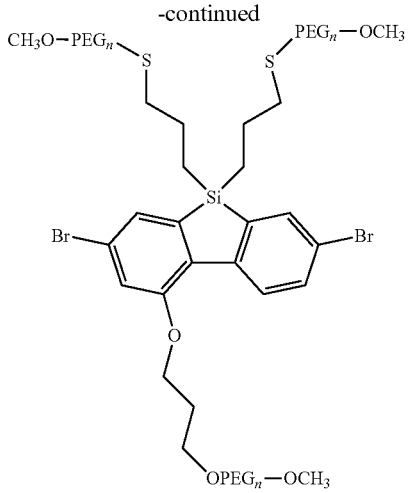

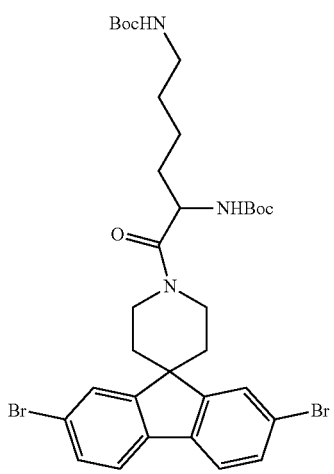

In general, the monomer can be made using chemistry as disclosed, for example, in US Patent Application Publication No. 2014/0243283; and *J. Am. Chem. Soc.* 2011, 133, 12600-12607, incorporated herein by reference.

The following are some of the exemplary starting materials which can be made by the literature method. for example, *Adv. Synth. Catal.* 2010,352,3267-3274; *Chem. Commun.*, 2006, 885-887; *Tetrahedron Letters* 20 (36): 3437-3440; *Organic Letters* 7 (19): 4297-4300; *J. Am. Chem. Soc.* 128 (27): 8754-8756; US20140243283, U.S. Pat. No. 7,713,452.

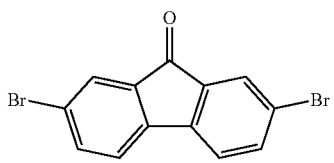 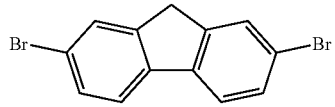 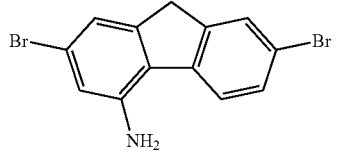

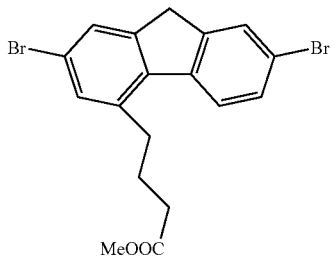 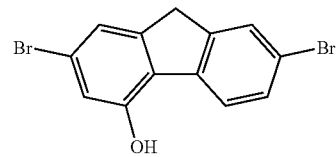 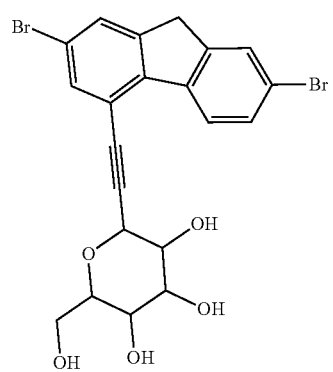

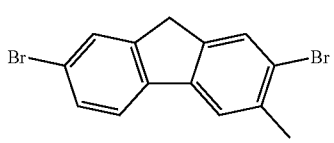 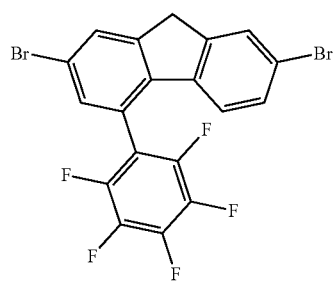 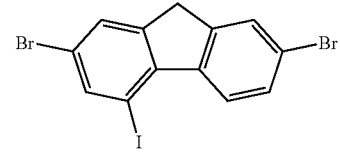

-continued
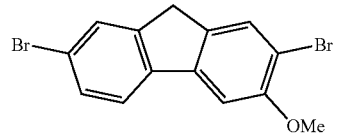
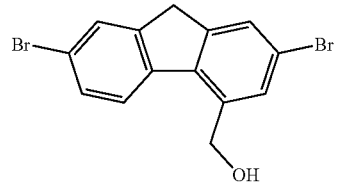
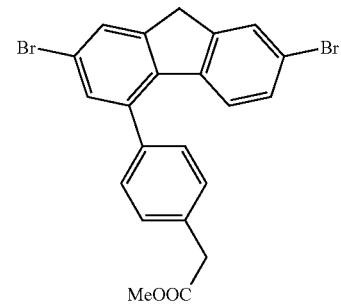
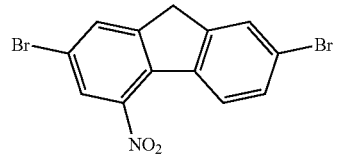
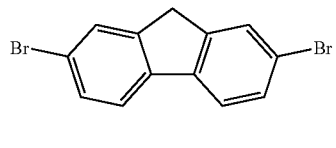 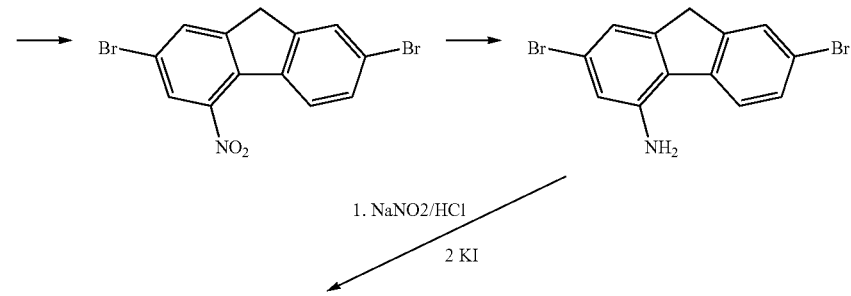
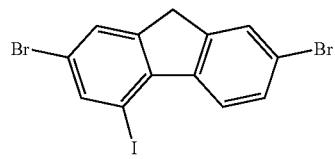
1. NaNO2/HCl
2. KI
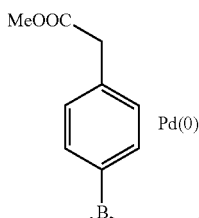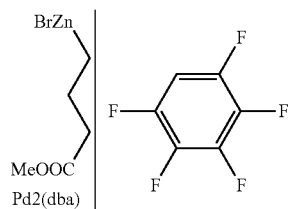
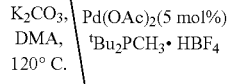 K₂CO₃, Pd(OAc)₂ (5 mol%)
ᵗBu₂PCH₃·HBF₄
DMA, 120° C.
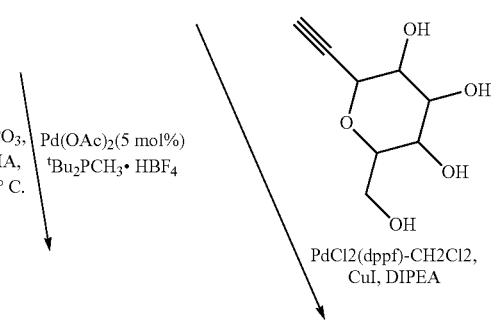
PdCl2(dppf)-CH2Cl2, CuI, DIPEA
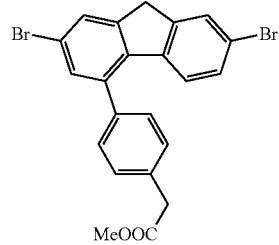 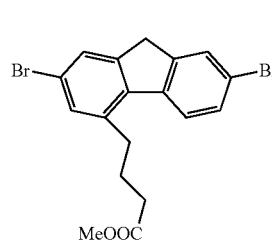 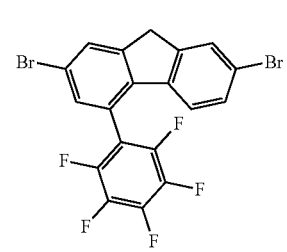 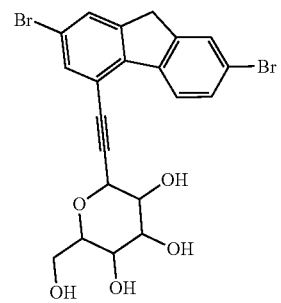

In certain aspects, the starting materials listed above, can have a water solubilizing group such as a linear and branched poly(ethylene glycol)s, $SO_3$, etc., introduced by current chemistry. The monomers can also copolymerize with other conjugated systems to introduce more bulkiness, thereby further extending the molecule's excitation and emission wavelength.

III. Examples

Example 1

Synthesis of 2',7'-dibromo-3,3-bis(bromomethyl) spiro[cyclobutane-1,9'-fluorene]

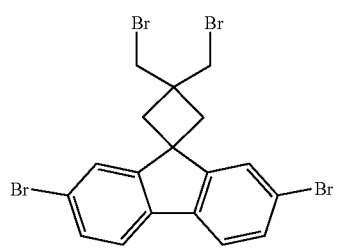

To a mixture of 2,7-dibromo fluorene (3.26 g, 10 mmol) in 50 ml anhydrous THF in a 250 ml three-necked flask under Ar protection, NaH (0.6 g, 25 mmol) NaH flask was added over 30 min. The mixture was stirred at room temperature 30 min, pentaerythrityl bromide (3.87 g, 10 mmol) of in 20 ml anhydrous THF were then dropped to the flask. The mixture was heated at 70° C. overnight. After the reaction was completed, the mixed solution was quenched by ice $H_2O$, then extracted three times with $CH_2Cl_2$, and the $CH_2Cl_2$ solution was dried over anhydrous magnesium sulfate, and filtered. The filtrate was rotary evaporated to give a brown solid, the solid was separated by column chromatograph to afford the yellow solid.

HNMR (600 MHz, CDCl3): δ 7.71 (d, 2H), 7.53 (d, 2H), 7.49 (dd, 2H), 3.80 (s, 4H, CM), 3.06 (s, 4H, $CH_2$).

Example 2

Synthesis of 2',7'-dibromo-3,3-bis(O-$PEG_{550}$ methyl ether)spiro[cyclobutane-1,9'-fluorene](SqPEG)

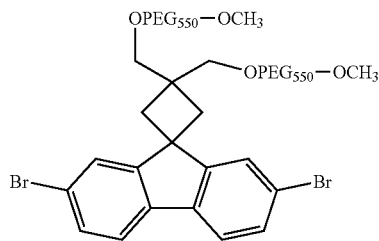

mPEG550 alcohol (HO-$PEG_{550}$-$OCH_3$) (3.331 g) was dissolved in anhydrous THF (20 mL) at 0° C., under nitrogen. To the mixture, was added potassium tert-butoxide (7.74 mmol, 7.74 mL, 1M in THF). After 10 min stirring, 2',7'-dibromo-3,3-bis(bromomethyl) spiro[cyclobutane-1,9'-fluorene](1.45 g, 2.579 mmol) in 20 mL of anhydrous THF was added via a syringe. The mixture was allowed to warm room temperature and stirred overnight. After evaporation of THF, brine (50 mL) was added and crude product was extracted with dichloromethane (3×40 mL). The combined organic layers were concentrated and purified by column chromatography (DCM-isopropanol) to give colorless oil product (2.164 g).

Example 3

Synthesis of 2,7-Dibromo-3-methyl-9-fluorenone

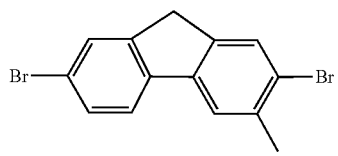 [SMILES: Cc1cc2c(cc1Br)Cc1cc(Br)ccc1-2]

The starting material 3-methyl-9-fluorenone was made according to *Adv. Synth. Catal.* 2010, 352, 3267-3274 and *J. Am. Chem. Soc.*, 2006, 128 (5), pp 1434-1435.

A stirred solution of 3-methylfluorene (65 g, 0.36 mol) and dichloromethane (650 mL) was treated drop-wise with a portion of the solution of bromine (37 ml, 115 g, 0.72 mol) and dichloromethane (34.3 mL) at room temperature to initiate a reaction. The reaction was then cooled to −2° C. and the reminder of the bromine-dichloromethane solution added over 2 hours. The resulting slurry was stirred for a further 30 min. then diluted with methanol (1300 mL) and stored under refrigeration for 3 days. The product was collected, washed with methanol (300 mL) and dried under vacuum to yield crude product as an off-white solid. Purification by recrystallization (1-butanol) afforded 2,7-dibromo-3-methylfluorene (107.5 g, yield 88%).

Example 4

Synthesis of mPEG550-I

An oven-dried two neck flask fitted with a reflux condenser, argon inlet, and septum was cooled under argon flow. Under argon counter flow, mPEG550-OTs (3.30 g) and NaI (8.16 g, 54.4 mmol) were added and the flask was cycled between vacuum and argon. The argon inlet was replaced by a $CaSO_4$ drying tube and acetone (110 mL, dried over $CaSO_4$) was transferred by cannula. The reaction was heated to reflux and stirred at this temperature for 15 hrs with visible precipitate formation soon after heat was applied. The reaction was then allowed to cool to room temperature and the solvent was evaporated under reduced pressure. The remaining residue was taken up in $CH_2Cl_2$/$H_2O$ (75 mL/110 mL) and transferred to a separatory funnel. The organic layer was separated and the aqueous layer was extracted with $CH_2Cl_2$ (2×65 mL). The combined organic layers were washed with aqueous NaCl solution (2×90 mL), dried over $Na_2SO_4$, filtered, and the solvent was evaporated under reduced pressure to give a yellow-brown oil (3.57 g). This material was used without further purification.

Example 5

Synthesis 2,2'-(2,7-dibromo-3-methyl-9H-fluorene-9,9-diyl)bis(ethan-1-O-PEG$_{550}$-O—CH$_3$)

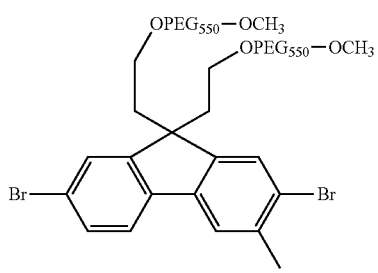

To the mixture of 2,7-Dibromo-3-methyl-9-fluorenone (2.0 g, 5.91 mmol) in 20 mL of anhydrous THF, potassium tert-butoxide (29.55 mmol, 20.9 mL, 1M in THF was added via a syringe. After 30 min stirring at room temperature under nitrogen, mPEG550 iodide (11.20 g) was added. The mixture was allowed to room temperature and stirred overnight. After evaporation of THF, brine (50 mL) was added and crude product was extracted with dichloromethane (3×40 mL). The combined organic layers were concentrated and purified by column chromatography (DCM-methanol) to give colorless oil product (7.138 g, 84%).

Example 6

Synthesis of 4-hydroxymethyl-2,7,dibromofluorene

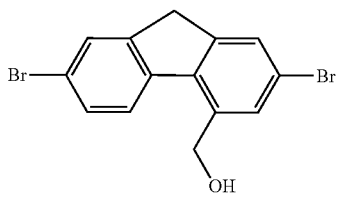 [SMILES: OCc1cc(Br)cc2c1-c1ccc(Br)cc1C2]

4-hydroxymethyl fluorene was made according to EP 0 524 624, incorporated herein by reference.

Bromine (0.7 ml, 13.8 mmol) was added slowly to a mixture of 4-hydroxymethyl fluorene (1.35 g, 6.9 mmol), iodine (140.0 mg, 0.1 mmol) and dichloromethane (70 ml) over 30 min. at 0° C. in the dark. The mixture was stirred at 0° C. for 1 h then at room temperature for 2 h. An aqueous Na$_2$S$_2$O$_3$ solution (10%, 5 ml) and then water (30 ml) were added to quench the reaction. The organic phase was separated and the aqueous phase was extracted with dichloromethane. The combined organic phases were dried over magnesium sulphate and evaporated under reduced pressure to give a crude solid. The crude material was purified by column chromatography and recrystallised from ethanol to give the title compound (1.90 g, 78%) as yellow crystals.

Example 7

The synthesis of 2,2'-(2,7-dibromo-4-(CH$_2$O-PEG$_{550}$-OCH$_3$)-9H-fluorene-9,9-diyl)bis(ethan-1-O-PEG$_{550}$-OCH$_3$).

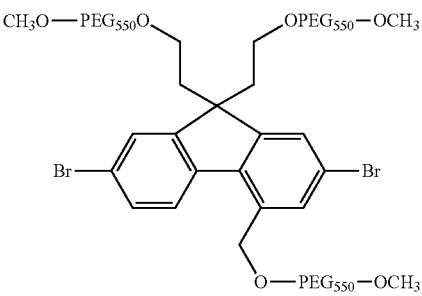

The compound was made as colorless oil similar to Example 2 while 4-hydroxymethyl-2,7,dibromofluorene and mPEG550-I were used as starting materials instead.

Example 8

Synthesis of 2,2'-(2,7-dibromo-4-O-PEG$_{550}$-OCH$_3$-9H-fluorene-9,9-diyl)bis(ethan-1-O-PEG$_{550}$-OCH$_3$)

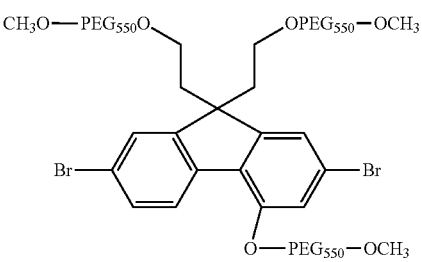

The starting material 4-hydroxyl-2,7,-dibromofluorene was made according literature *Chem. Commun.*, 2006, 885-887. The compound was made as a yellow oil similar to Example 2 while 4-hydroxyl-2,7-dibromofluorene and CH$_3$—O-PEG550-I were used as starting materials.

Example 9

Synthesis of Spiro-[2,7-dibromofluoren-9,4'-imidazolidine]-2',5'-dione

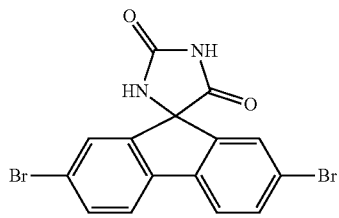 [SMILES: O=C1NC(=O)C2(N1)c1cc(Br)ccc1-c1ccc(Br)cc12]

The 2,7-dibromofluorenone (1.2 g, 3.6 mmol), KCN (0.468, 7 mmol) and ammonium carbonate (1.36 g) in ethanol (15 mL) were heated at 105° C. overnight in a stainless steel pressure reactor, cooled and diluted with ice cold 10% hydrochloric acid. The triturated solid was collected on the filter, washed with water and dried to yield 11.8 g (95%), the product having a m.p. 340° C., [M+]406.

Example 10

The synthesis of 2,7-dibromo-1',3'-bis(2-O-PEG$_{550}$-OCH$_3$ethyl)spiro[fluorene-9,4'-imidazolidine]-2',5'-dione.

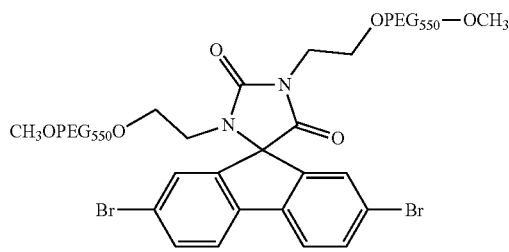

To the solution of Spiro-[2,7-dibromofluoren-9,4'-imidazolidine]-2',5'-dione (500 mg, 1.01 mmol) in 10 mL anhydrous THF, potassium t-butoxide (0.755 mL, 14.10 mmol) in THF was added and the solution was stirred at 60° C. for 30 min, CH$_3$—O-PEG$_{550}$-I (2.0 g) of was then added and the reaction was allowed to stir overnight. TLC was used to monitor the reaction. Then, 150 mL DCM was added to the reaction mixture. The organic phase was washed with 150 mL water and dried over sodium sulfate. The solvent was removed under reduced pressure. The desired product was purified by column chromatograph (DCM/Methanol) to obtain as a yellow oil. (Yield 70%).

Example 11

The synthesis of 2,6-diamino(Boc)-1-(2,7-dibromospiro[fluorene-9,4'-piperidin]-1'-yl)hexan-1-one. (MBoc):

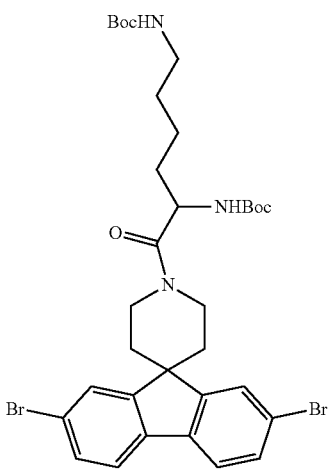 [SMILES: CC(C)(C)OC(=O)NCCCCC(NC(=O)OC(C)(C)C)C(=O)N1CCC2(CC1)c1cc(Br)ccc1-c1ccc(Br)cc12]

The starting material 2,7-dibromo-1'-methyl-spiro[fluorene-9,4'-piperidine] was made according to US 2014/0243283.
The mixture of (Boc-Lys(Boc)-OH (6.6 g, 18 mmol) and triethylamine (5.1 ml, 36 mmol) in 100 ml of CH$_2$Cl$_2$, of is cooled to 0° C., then EDC-HCl (3.43 g, 18 mmol) was added, the mixture was stirred for 20 min, 2,7-dibromo-1'-methyl-spiro[fluorene-9,4'-piperidine](5.0 g, 12 mmol) was added and the mixture was stirred for 16 h at room temperature. To the reaction mixture 100 ml of CH$_2$Cl$_2$ and 100 ml of water were added. The phases were separated and aqueous phase is again extracted with 100 ml of CH$_2$Cl$_2$. Collected organic phases were washed with water (200 ml×2). The organic phase was evaporated to dryness and separated by hexane/EtOAc to afford white cotton solid 8.21 gm (yield 95%).

Example 12

The synthesis of 2,6-diaminoBOC-N-(2,7-dibromo-9,9-bis(3-bromopropyl)-9H-fluoren-4-yl)hexanamide.

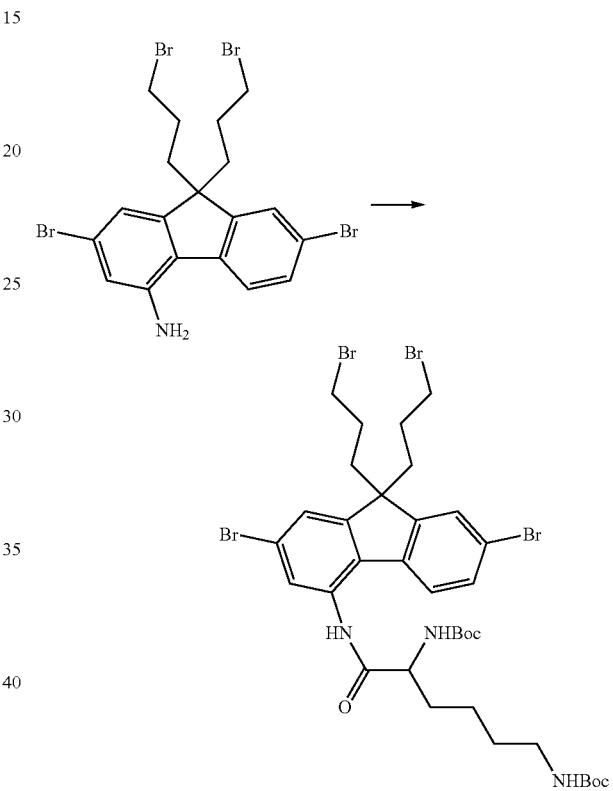

The starting material of 2,7-dibromo-5-amine-9,9-bis(3-bromo-propyl)-fluorene was made as yellow solid according to *Chem. Commun.*, 2006, 885-887. and *J. Mater. Chem.*, 2009, 19, 399-408.
The mixture of 100 ml of CH$_2$Cl$_2$, (Boc-Lys(Boc)-OH (8.04 g, 23.2 mmol), 40 ml of triethylamine (4.85 ml, 34.8 mmol) is cooled to 0° C., then HATU (8.82 g, 23.2 mmol) was added, after 20 min, 2,7-dibromo-5-amine-9,9-bis(3-bromo-propyl)-fluorene (9.0 g, 15.4 mmol) was added and the mixture was stirred for 16 h at room temperature. To the reaction mixture 200 ml of CH$_2$Cl$_2$ and 200 ml of water were added. The phases were separated and aqueous phase was again extracted with 100 ml of CH$_2$Cl$_2$. Collected organic phases were washed with water (200 ml×2). The organic phase was evaporated to dryness and separated by hexane/ EtOAc to afford white solid 6.71 g, yield 75%.

Example 13

The synthesis of 2,6-diamino(Boc)-N-(2',7'-dibromo-3,3-bis(O-PEG$_{550}$-OCH$_3$ methyl)spiro[cyclobutane-1,9'-fluoren]-4'-yl)hexanamide.

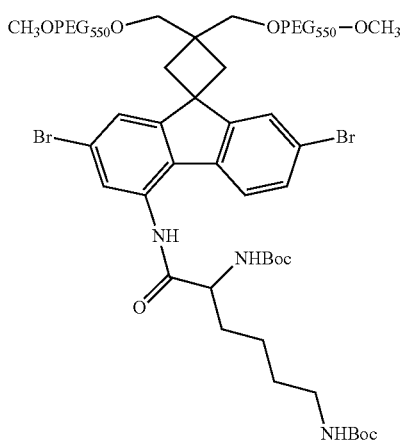

the compound was made as yellow oil similarly to example 2 while compound 2,6-diamino-BOC-N-(2,7-dibromo-9,9-bis(3-bromopropyl)-9H-fluoren-4-yl)hexanamide in example 12 was used as starting materials.

Example 14

The synthesis of 2,7-Dibromospiro[fluorene-9,9'-xanthene]-3',6'-diol.

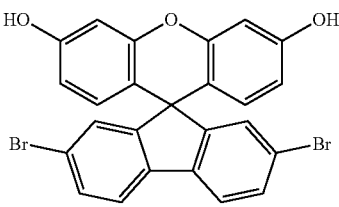 [SMILES: Oc1ccc2c(c1)Oc1cc(O)ccc1C21c2cc(Br)ccc2-c2ccc(Br)cc21]

To a three-necked flask were added 2,7-dibromo-9-fluorenone (1.01 g, 3.0 mmol), resorcinol (1.32 g, 12.0 mmol), p-TsOH (0.3 mmol) and toluene (20 mL). The mixture was refluxed for 6 h, and then cooled to room temperature. After water (10 mL) was added, the mixture was stirred for 0.5 h. The crude product was precipitated from the reaction mixture, and was isolated as a yellow solid by filtration. The crude product was dissolved into alcohol (10 mL) and filtrated to remove insoluble impurity. The organic solution was concentrated, purified by chromatography on silica gel using petroleum ether/EtOAc (3:1), and dried in vacuum at 100° C. for 5 h to afford product as a white solid at a yield 81%, 1.26 g.

1H NMR (400 MHz, DMSO-d6) H: 9.73 (2H, s, OH), 7.93 (2H, d, $^3J_{HH}$ 8.0 Hz, ArH), 7.75 (2H, d, $^3J_{HH}$ 8.0 Hz, ArH), 7.11 (2H, s, ArH), 6.59 (2H, s, ArH), 6.30 (2H, d, $^3J_{HH}$ 8.8 Hz, ArH), 6.05 (2H, d, $^3J_{HH}$ 8.8 Hz, ArH).

Example 15

The synthesis of 2,7-dibromospiro[fluorene-9,9'-xanthene]-3',6'-O-PEG$_{550}$-OCH$_3$

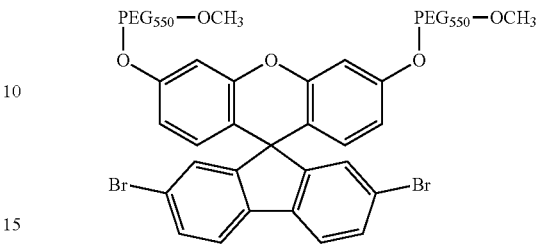

The compound was made similarly to example 10 while spiro[fluorene-9,9'-xanthene]-3',6'-diol and mPEG550-I was used as starting materials.

To a solution of K$_2$CO$_3$ (6.38 g, 46.3 mmol) and 2,7-dibromospiro[fluorene-9,9'-xanthene]-3',6'-diol (11.11 g, 21.3 mmol) in a 100-mL three neck flask, a solution of mPEG550-I (43.32 g) in 150 mL THF was added dropwise under nitrogen atmosphere. The reaction mixture was refluxed for 12 h at 80° C. After cooling to room temperature, the solution was extracted with DCM, the collected organic phase was dried over magnesium sulfate and filtered, rotary evaporated to remove solvent. The crude product was isolated, and further purified by column chromatography over silica gel by eluting with DCM/Methanol (19:1) to yield 30.81 g (88%) of yellow oil.

Example 16

The synthesis of N-(6-aminohexylBoc)-2-(4-bromophenyl)acetamide.

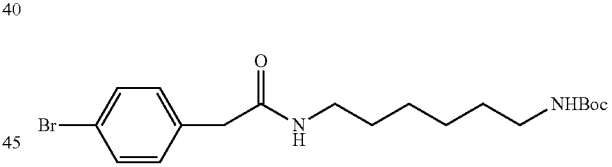

To a mixture of 4-bromophenylacetic acid (0.860 g, 4.0 mmol) and HOBt (0.540 g, 40 mmol) in 30 mL of dry DMF chilled in an ice-water bath, DCC (906 mg, 4.4 mmol) was added in one portion. The mixture was stirred for 30 min at the ice bath, N-Boc-1,6-hexanediamine (0.864 g, 4.0 mmol) and TEA (1.37 ml, 10 mmol) were added and the mixture was stirred overnight. The mixture was poured into 15 mL of hexanes with shaking. The solid was removed by filtration and washed with 10 mL of hexane. The solid was washed by 4% HCl (30 mL×2), saturated NaHCO$_3$ solution (25 mL×3) and brine (30 mL×3), and was separation by column chromatography to give 1.55 g of (94%) of the product.

Example 17

The synthesis of copolymer of 2,6-diamino-1-(2-(3,3-bis (O-PEG$_{550}$-OCH$_3$methyl)-2'-phenylspiro[cyclobutane-1,9'-fluoren]-7'-yl)-7-phenylspiro[fluorene-9,4'-piperidin]-1'-yl) hexan-1-one.

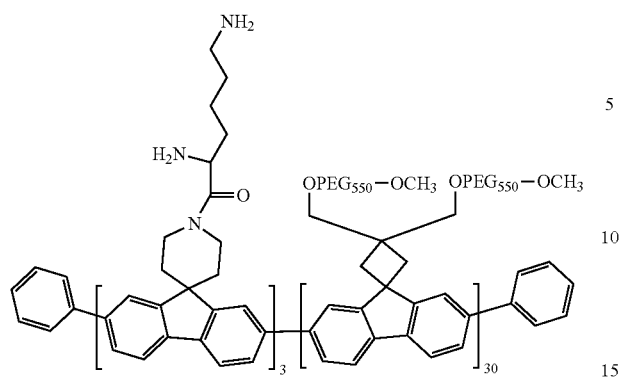

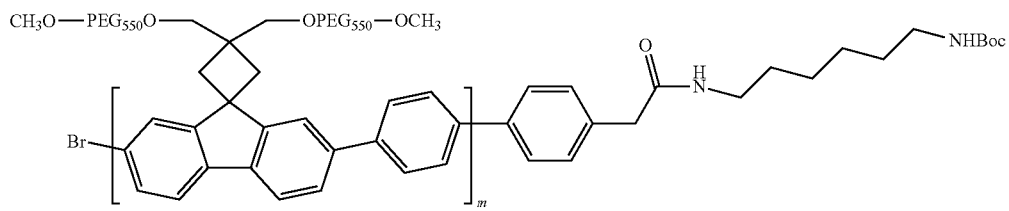

To a stirred solution of Ni(COD)$_2$ (276 mg, 1.0 mmol) and 2,2'-bipyridine (157 mg, 1.0 mmol) in dry DMF (3.5 ml) was added COD (123 µl, 1.0 mmol) and the resultant solution was stirred for 1 h at 75° C. under nitrogen. 2,6-diamino (Boc)-1-(2,7-dibromospiro[fluorene-9,4'-piperidin]-1'-yl) hexan-1-one (65 mg, 0.091 mmol)) and 2',7'-dibromo-3,3-bis(O-PEG$_{550}$ methyl ether)spiro[cyclobutane-1,9'-fluorene] (1.385 g, 0.91 mmol) was dissolved in DMF (6 ml) in a separation flask under nitrogen and then added to the mixture. The mixture was stirred overnight for 24 h at 75° C. under nitrogen. Bromobenzene (95 ul, 0.91 mmol) was added to the mixture and stirred for 12 h under the same conditions. The mixture was dropped slowly by pipette into a stirred solvent 6N HCl 150 ml and the resultant mixture was stirred for 2 h. The mixture was exacted by DCM and organic layer was washed with 50 ml 1N HCl. The solvent was evaporated off and further dried under high vacuum to give a light wax compound. (820 mg), GPC (M$_w$=M$_n$=63,000; PDI=2.2).

Gel permeation chromatography (GPC) was carried out in THF at 50° C. using a 5 µm WatersStyragel® HR3 and a HR4 GPC column system on a Agilent 1200 HPLC Separations Module with a Agilent UV Detector using a flow rate of 0.5 mL/min. The system was calibrated with Agilent's EasiCal PS-2 standards in range of 580 to 364,000 g/mol.

The above compound was then dissolved in 30 ml DCM and 30 ml TFA mixture, then stirred at room temperature overnight. The solvent was removed under reduced pressure and then dried down under high vacuum pump overnight. This polymer needs further purification before labelling. For purification, the dried polymer was resuspended in DI water and kept under stirring overnight. Most of polymer was dissolved, the undissolved precipitates were removed by centrifugation at 10,000 rpm for 5 min. the supernatant was filtered by 0.22 um PES filter and concentrated by Amicon® Ultra-4 Centrifugal Filter Units (MWCO, 30K) (available from EMD Millipore Corporation, Billerica, MA). Then this solution was loaded to G-25 column (Sephadex G-25 Fine, GE Healthcare Life Sciences) to remove catalyst impurities. The purified polymer was further fractionated by flowing through a Superose 6 column (GE Life Sciences) to narrow down size distribution.

Example 18

The synthesis of copolymer of N-(6-amino(Boc)hexyl)-2-(4'-(2'-bromo-3,3-bis(O-PEG$_{550}$-OCH$_3$methyl)spiro[cyclobutane-1,9'-fluoren]-7'-yl)-[1,1'-biphenyl]-4-yl)acetamide 2',7'-dibromo-3,3-bis(O-PEG$_{550}$ methyl ether)spiro[cyclobutane-1,9'-fluorene](1.522 g, 1.0 mmol), benzene-1,4-diboronic acid (165 mg, 1.0 mmol), capping reagents compound N-(6-aminohexylBoc)-2-(4-bromophenyl)acetamide (20 mg, 0.05 mmol) (example 16), tetrakis(triphenylphosphine)palladium(0) (36 mg, 0.03 mmol) were mixed and dissolved in 0.5 mL tetrahydrofuran in a 15 mL round-bottom flask equipped with a condenser and vacuum adaptor. 0.3 mL of 2M potassium carbonate solution was added and the flask was connected to a Schlenk line. The reagent mixture was carefully degassed through 4 cycles of freeze-pump-thaw and after the last cycle the flask was refilled with argon. The reaction mixture was refluxed under argon for 24 h. The reaction was stopped and cooled to room temperature. The organic layer was carefully collected, evaporated to dryness and redissolved in 4 mL chloroform. The solution was filtered through 0.45 µm glass fiber filter and then poured into 60 mL hexane to precipitate the polymers. Polymers were collected by centrifugation and redissolved in methylene chloride. The precipitation-centrifugation-redissolution cycle was repeated twice more. The crude polymer product was then dissolved in 10 mL DI water and filtered 3 times through Amicon® Ultra-4 Centrifugal Filter Units (MWCO, 30K) (available from EMD Millipore Corporation, Billerica, MA) to remove low molecular weight polymers. The polymer product (m=35) was dried in reduced pressure and collected as amber wax (890 mg).

Example 19

The Synthesis of Polymer P138N

Polymer P138 was made as a yellow solid compound similar to example 17 by using 10% 2,6-diamino(Boc)-1-(2,7-dibromospiro[fluorene-9,4'-piperidin]-1'-yl)hexan-1-one and 90% 2',7'-dibromo-3,3-bis(O-PEG$_{550}$ methyl ether) spiro[cyclobutane-1,9'-fluorene].

A 100 mL round-bottom flask equipped with a stir bar was charged with polymer P138 (200 mg). 20.8 mL of glacial acetic acid was added, followed by 20 mL of CH$_2$Cl$_2$. The mixture was stirred until homogeneous, and 4.2 mL of fuming nitric acid was added. The mixture was stirred at room temperature for 6 h, and 20 mL of 0.5 M sodium bicarbonate solution was slowly added. It was then extracted with $CH_2Cl_2$, dried over magnesium sulphate, and evaporated to dryness leaving 120 mg of Polymer P138N a yellow solid.

Example 20

Measurement of Optical Properties

The spectral properties were evaluated for Pacific Blue™ and Alexa Fluor® 405 (Life Technologies Corporation) and a macromer of the invention. The absorbance wavelength maximum, (λ), emission wavelength maximum (λ), quantum yield (QY) and extinction coefficient for each compound is measured. Fluorescence spectra is collected in aqueous solution using an excitation wavelength of 390 nm. Quantum yield is measured on a Hamamatsu absolute PL quantum yields measurement system with excitation at 390 nm. Fluorescence UV-Vis absorption and emission spectra are recorded on a Perkin-Elmer Lambda 45 UV/Vis spectrophotometer in aqueous solutions at room temperature.

The absorption maxima are centered on the 390-405 nm range, well suitable for 405 nm laser excitation typically found on flow cytometers. The quantitative brightness measurements also illustrates the extraordinary light-emitting capability of the macromers.

| Compound | Sq-Peg/MBoc | Absorption λ (nm) | Emission λ (nm) | Mn | Extinction coefficient ($\times 10^6$ $cm^{-1}M^{-1}$) |
|---|---|---|---|---|---|
| Pacific blue | | 403 | 455 | | 0.046 |
| P84 | 90/10 | 357 | 421 | 10K | 0.155 |
| P89 | 50/50 | 395 | 425 | 35K | 1.229 |
| P114 | 50/50 | 385 | 425 | 32.2K | 0.893 |
| P118-1 | 90/10 | 393 | 421 | 20K | 1.100 |
| P127 | 60/40 | 390 | 425 | 45K | 1.580 |
| P138 | 90/10 | 393 | 425 | 30K | |
| P138N (Example 19) | 90/10 | Broad peak at 260-400 nm | No fluorescence | | |

The table shows that the spectral characteristics substituted macromere/polymers were similar to those of poly(fluorene). The absorption maxima were centered on the 390-405 nm range. It is also found that ring substituted macromere/polymers resulted in a modest (e.g., 5-10 nm) blue-shift in absorption maxima. The fluorescent emission peaks were red-shifted also. For some substitution groups in the ring, the fluorescence was totally lost (example 19) because of their interference with the relatively larger conjugated π system.

Example 21

The Synthesis of 2,6-diamino(Boc)-1-(2-(9,9-bis(2-O-$PEG_{550}$-$OCH_3$ethyl)-4-(hydroxymethyl)-7-phenyl-9H-fluoren-2-yl)-7-phenyl spiro[fluorene-9,4'-piperidin]-1'-yl)hexan-1-one

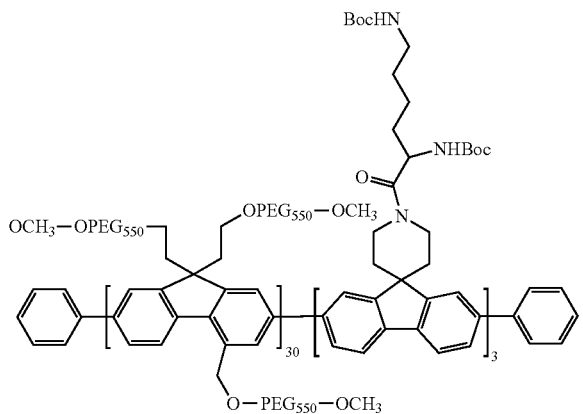

Polymer 2,6-diamino(Boc)-1-(2-(9,9-bis(2-O-PEG550-OCH3ethyl)-4-(hydroxymethyl)-7-phenyl-9H-fluoren-2-yl)-7-phenylspiro[fluorene-9,4'-piperidin]-1'-yl)hexan-1-one is synthesized similarly to example 17 while the monomer 2,2'-(2,7-dibromo-4-(CH2O-PEG550-OCH3)-9H-fluorene-9,9-diyl)bis(ethan-1-O-PEG550-OCH3) and monomer2,6-diamino(Boc)-1-(2,7-dibromospiro[fluorene-9,4'-piperidin]-1'-yl)hexan-1-one are used as starting materials.

Example 22

The Synthesis of 2,6-diamino(Boc)-N-(3,3,3'',3''-tetrakis(O-$PEG_{550}$-$OCH_3$methyl)-7',7'''-diphenyl-2',2'''-bispiro[cyclobutane-1,9'-fluoren]-5'-yl)hexanamide

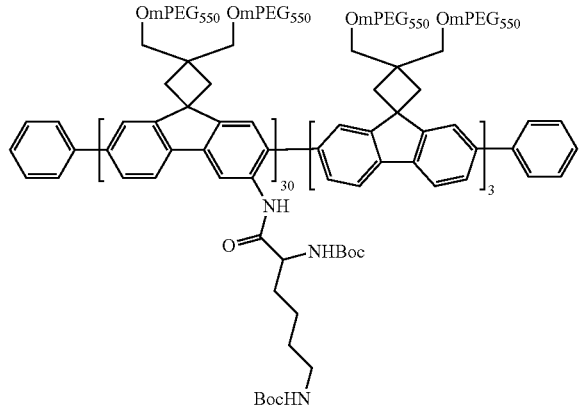

Polymer 2,6-diamino(Boc)-N-(3,3,3'',3''-tetrakis(O-$PEG_{550}$-$OCH_3$methyl)-7',7'''-diphenyl-2',2'''-bispiro[cyclobutane-1,9'-fluoren]-5'-yl)hexanamide is synthesized similarly to example 17 while the monomer 2,6-diamino(Boc)-N-(2',7'-dibromo-3,3-bis(O-PEG550-OCH3 methyl)

spiro[cyclobutane-1,9'-fluoren]-4'-yl)hexanamide. and monomer 2',7'-dibromo-3,3-bis(O-PEG550 methyl ether) spiro[cyclobutane-1,9'-fluorene] are used as starting materials.

Example 23

Conjugation of Polymer Dyes (P84 and P118) to Antibodies

A method for conjugation of antibodies to polymer dye is described. Mouse monoclonal antibody against human CD4 (UCHT1) or anti-human IFN-γ Antibody (4S.B3) were used for conjugation. The antibodies solution (5 mg/ml in PBS, pH7.2) were reduced by DTT activation (Dithiothreitol) at a molar ratio of 160:1 for 30 min. They were purified and buffer-exchanged to 50 mM Phosphate, 5 mM EDTA pH7.0 by G-25 column (Sephadex G-25 Fine, GE Healthcare Life Sciences). The polymer dyes in 50 mM Phosphate, 5 mM EDTA pH7.0 were activated by 25× molar excess of Sulfo-SMCC (sulfosuccinimidyl 4-(N-maleimidomethyl)cyclohexane-1-carboxylate, Cova Chem) for 2 hours. Then the free Sulfo-SMCC reagents were removed by G-25 column. For conjugation, the DTT-reduced antibody was mixed with SMCC-activated polymer dyes at 4:1 molar ratio for 18-20 hours. After purifying with Protein G resin, the conjugates are separated from free antibody by Superose 6 (GE Life Sciences) and concentrated by centrifugal filters (30K $M_w$ cut-off, Millipore). These antibody-polymer conjugates were evaluated by flow cytometry.

Example 24

P114-A700 Tandem Dye Preparation

Alexa Fluor™ 700 NHS Ester (Thermo Fisher) (5 ul of 10 mg/ml) (was added slowly to 0.21 ml of polymer P114 in 50 mM Phosphate, 5 mM EDTA pH7.0 buffer. The solution was light-protected and vortexed for 10 s, and then was rotatored for 2 h. The mixture was purified by G-25 (Sephadex G-25 Fine, GE Healthcare Life Sciences) to get P114-A700 tandem dye.

Then P114-A700 tandem dye was coupled to mouse monoclonal antibody against human CD4 (UCHT1) as example 23 above. The tandem conjugates has emission as FIG. 18 as below.

Example 25

Cellular Analysis by Flow Cytometry
Flow Cytometry Methods
Staining of Human Lysed Whole Blood (LWB) for Flow Cytometry.

100 µL of anti-coagulated whole blood was added to tubes containing pre-aliquoted fluorophore conjugated antibodies and gently mixed. The tubes were incubated at room temperature in the dark for 15 minutes, followed by addition of 2 mL of room temperature 1× RBC Lysis Buffer (BioLegend, Inc.) directly to the mixture. Tubes were incubated at room temperature in the dark for 15 minutes, followed by centrifugation at 1200-1500 rpm for 5 minutes to pellet the cells. Supernatants were removed, the tubes gently vortexed to loosen the cell pellets and 2 mL of FACS Wash Buffer (BioLegend, Inc) was added. Tubes were centrifuged at 1200-1500 rpm for 5 minutes, the supernatants were aspirated, and the tubes were again vortexed to loosen the pellets. Cells were resuspended from the pellet by adding 300-500 µL of 1% paraformaldehyde in 1×PBS with $NaN_3$, pH 7.2 to each FACS tube. Cells were then ready for analysis by flow cytometry. Simple signal to noise (S/N) calculations are derived from mean fluorescence intensity (MFI) of the positively stained population divided by the MFI of the unstained population.

Staining of Intracellular Cytokines.

Human peripheral blood mononuclear cells (PBMC) were prepared and activated in vitro with PMA (50 ng/ml)+ionomycin (1 ug/ml) in the presence of monensin (BioLegend, Inc.) for 4 hours. Cells were suspended in FACS Wash Buffer (BioLegend) and counted. Cells were centrifuged at 1200-1500 rpm for five minutes and the wash supernatant removed. The cell pellet was loosened by gentle mixing and cells were then resuspended in 3 mL of 4% Paraformaldehyde fixation buffer while vortexing. Cells were allowed to fix at room temperature in the dark for 20 minutes. Cells were washed twice with 1× Permeabilization Buffer (BioLegend) by pelleting the cells at 1200-1500 rpm for 5 minutes, removing the supernatant, and vortexing to loosen the pellet. Cell density was adjusted to 5 million to 10 million cells/mL with 1× Permeabilization Buffer. 100 µL cell suspension was added into the tubes containing dilutions of appropriate antibodies to CD3 and to IFNγ. Cells were incubated in dark at room temperature for 20-30 minutes, followed by twice washing procedure with FACS Wash Buffer. Cells were resuspend in 500 µL FACS Wash Buffer and analyzed by Flow Cytometry.

Flow cytometric analyses were performed with a BD LSR II instrument equipped with 355 nm Ultraviolet, 405 nm Violet, 488 nm Blue and 640 nm red excitation laser sources. Emissions derived from each laser excitation source were collected using the optical filters indicated in each figure.

Immunofluorescence Method

Human frozen tonsil tissue block were sectioned with Cryostat machine (Leica) and placed on positive charged microscope slides. Human frozen tonsil tissue on the microscope slides were fixed with 4% PFA for ten minutes and blocked with 5% FBS for 30 minutes. Then, the tissue was stained with 5 µg/mL of MY-118-1 directly conjugated anti-human CD3 antibody (green) overnight at 4° C. On the next day, tissue was washed with PBS twice for 5 minutes and mount with ProLong Gold (fisher scientific) antifade solution and cover slips. The image was scanned with a 10× objective and stitched with MetaMorph® software.

Example 26

Figure 13A:
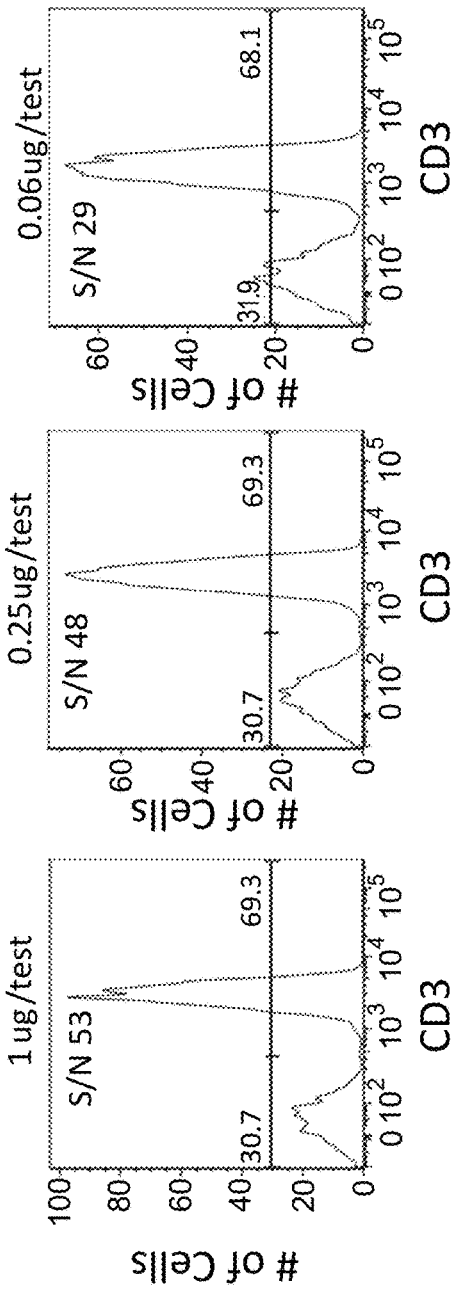
FIGS. 13 A-B illustrate surface flow cytometric analysis of anti-human CD3 clone UCHT1 conjugated with fluorophore P84 at 405 nm excitation; 400-500 nm emission (A); or 355 nm excitation; 400-500 nm emission (B).
Figure 13B:
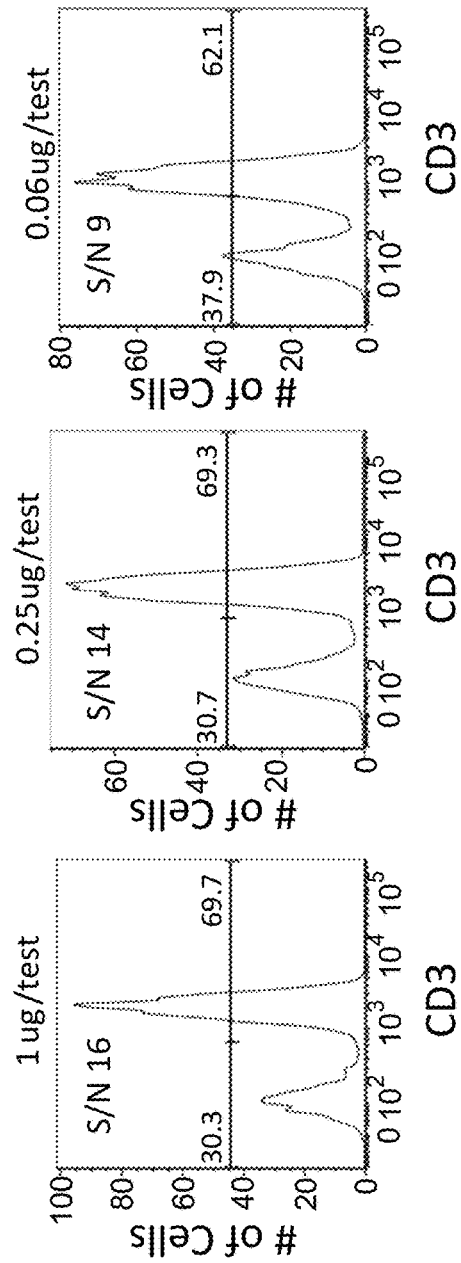

Cell surface flow cytometric analysis of human Lysed Washed Blood samples stained with P84 polymer fluorophore conjugated to anti-CD3 antibody. Human Lysed Washed Blood (LWB) samples were stained with 1.0, 0.25 or 0.06 ug/test of polymeric fluorophore P84 conjugated to the UCHT1 clone monoclonal antibody. Samples were analyzed on a BD LSR IIB flow cytometer using the indicated excitation laser sources and emission collection parameters shown in FIG. 13A and FIG. 13B. S/N value indicates the signal to noise ratio. The results show that the P84 antibody conjugate is able to stain and identify the surface CD3+ cell populations in the LWB heterogeneous cell mixture.

Example 27

Figure 14A:
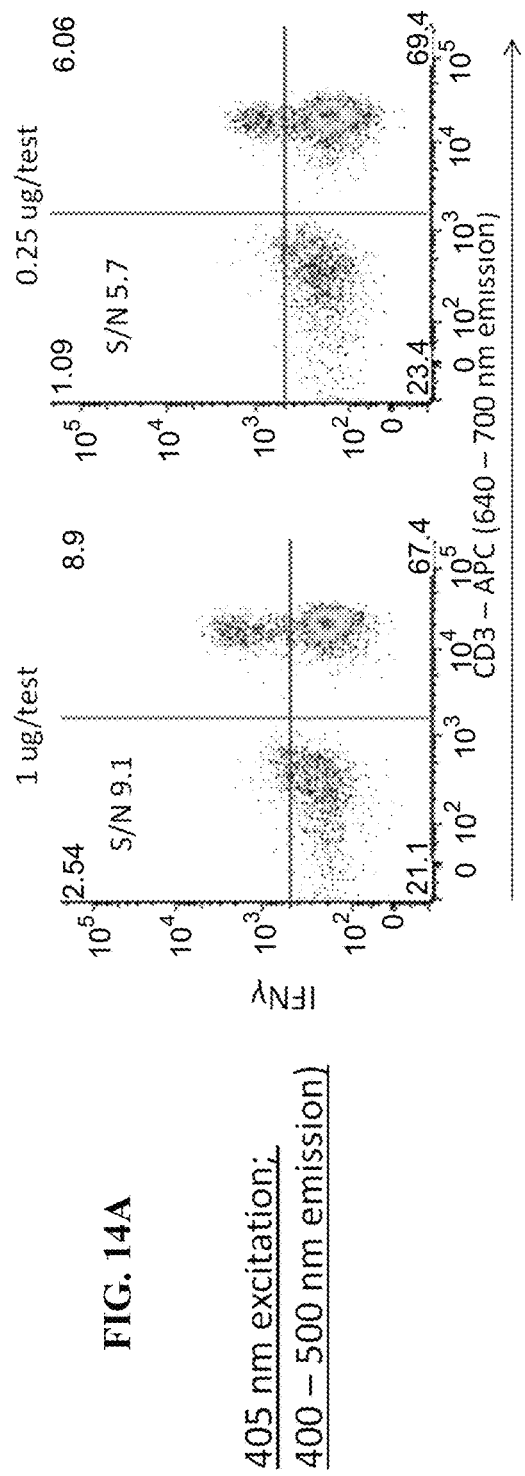
FIGS. 14 A-B illustrate intracellular flow cytometric analysis of anti-human IFNγ clone 4S.B3 conjugated with compound P84 at 405 nm excitation; 400-500 nm emission (A); or 355 nm excitation; 400-500 nm emission (B).
Figure 14B:
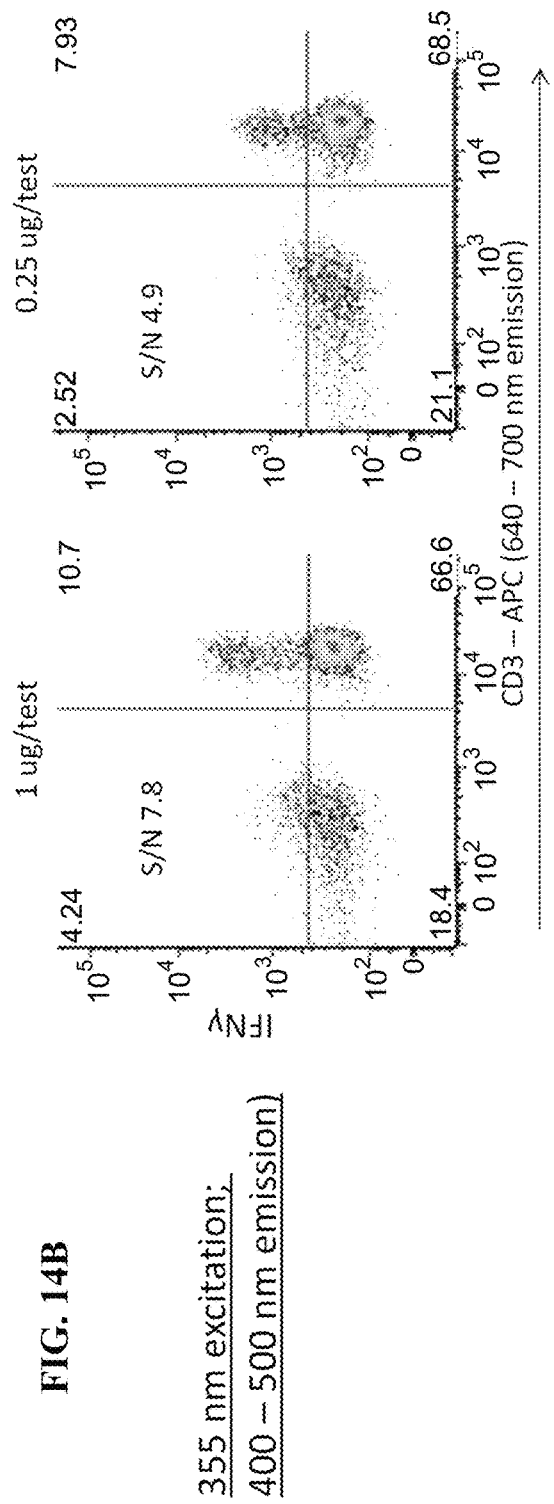

Intracellular flow cytometric analysis of IFNγ with P84 polymer fluorophore conjugated to anti-human IFNγ monoclonal antibody 4S.B3. Conjugated antibody was used to stain intracellular IFNγ in activated human peripheral blood mononuclear cell (PBMC) samples. Samples were also surface stained with allophycocyanin (APC)-conjugated anti-CD3 antibody to simultaneously identify T cells. Conjugated anti-IFNγ antibody was used at 1.0 ug/test and 0.25 ug/test. Samples were analyzed on a BD LSR IIB flow cytometer using the indicated excitation laser sources and emission collection parameters shown in FIG. 14A and FIG. 14B. Data is plotted as IFNγ on the ordinate and CD3 on the abscissa. The results show that the P84 fluorophore can be used in an intracellular staining protocol, and in combination with a surface staining antibody conjugated with a different fluorophore to identify IFNγ producing CD3+ T cells.

Example 28

Figure 15A:
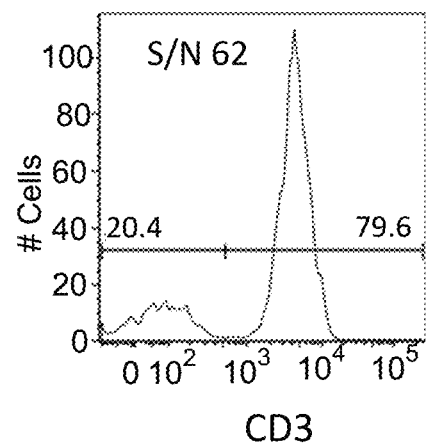
FIGS. 15 A-B illustrate surface flow cytometric analysis of anti-human CD3 clone UCHT1 conjugated with compound P114 at 405 nm excitation; 400-500 nm emission (A); or 355 nm excitation; 400-500 nm emission (B).
Figure 15B:
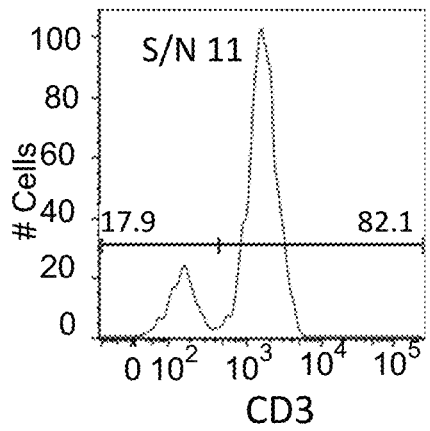

Cell surface flow cytometric analysis of human Lysed Washed Blood samples stained with P114 polymer fluorophore conjugated to anti-CD3 antibody. Human Lysed Washed Blood (LWB) samples were stained with 1.0 ug/test of polymeric fluorophore P114 conjugated to the UCHT1 clone monoclonal antibody. Samples were analyzed on a BD LSR IIB flow cytometer using the indicated excitation laser sources and emission collection parameters shown in FIG. 15A and FIG. 15B. The results show that the P114 antibody conjugate is able to clearly stain and identify the surface CD3+ cell populations in the LWB heterogeneous cell mixture. The results also illustrate that a second and distinct form of the invention is able to be used productively in a flow cytometry experiment.

Example 29

Figure 16A:
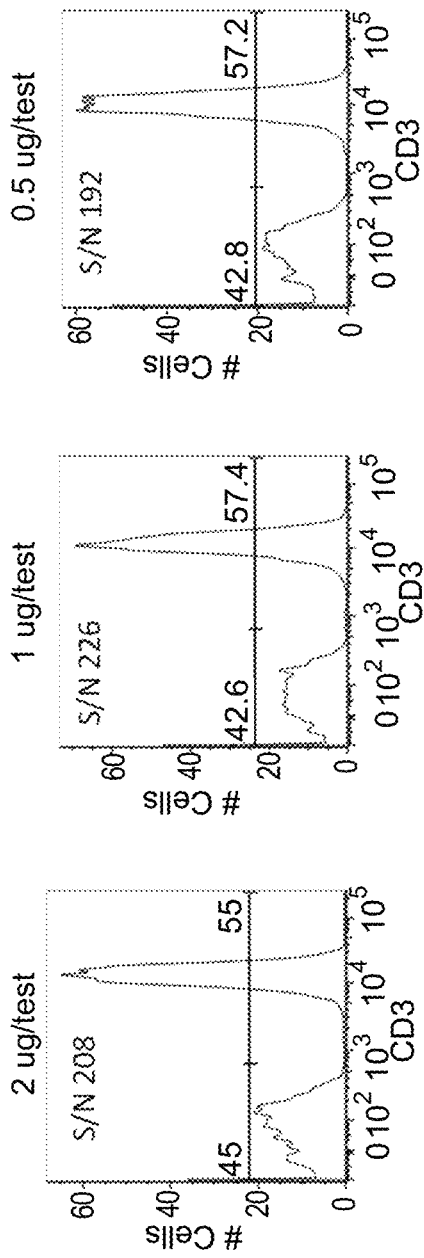
FIGS. 16A-B illustrate surface flow cytometric analysis of anti-human CD3 clone UCHT1 conjugated with compound P118-1 at 405 nm excitation; 400-500 nm emission (A); or 355 nm excitation; 400-500 nm emission (B).
Figure 16B:
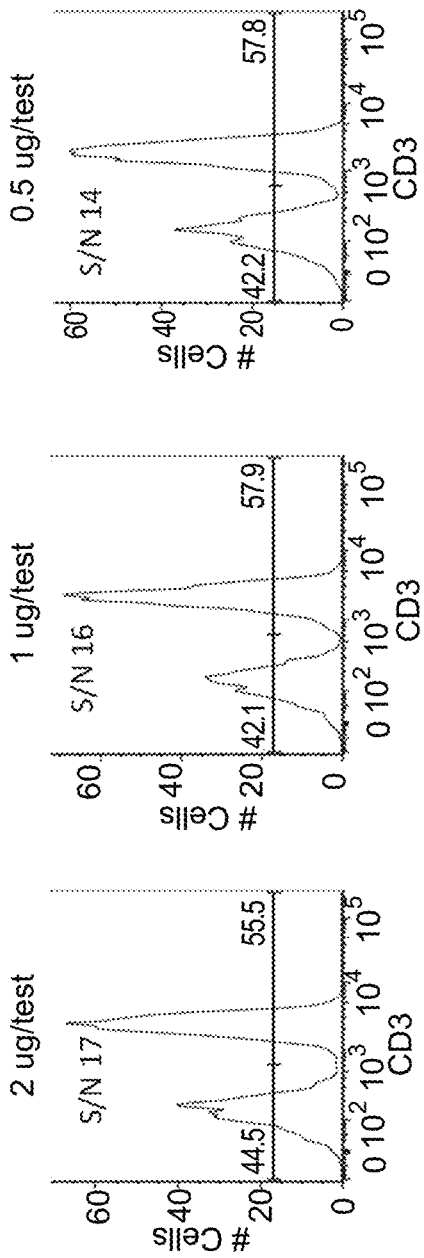

Cell surface flow cytometric analysis of LWB samples stained with anti-human CD3 clone UCHT1 conjugated with compound P118-1. Conjugated antibody was used to surface stain Lysed Washed Human Whole Blood (LWB) samples at three different amounts (2-, 1- and 0.5 ug/test). Samples were analyzed on a BD LSR IIB flow cytometer using the indicated excitation laser sources and emission collection parameters shown in FIG. 16A and FIG. 16B. The results show that the P118-1 antibody conjugate is able to clearly stain and identify the surface CD3+ cell populations in the LWB heterogeneous cell mixture. The results also illustrate that a third and distinct form of the invention is able to be used productively in a flow cytometry experiment.

Example 30

Figure 17A:
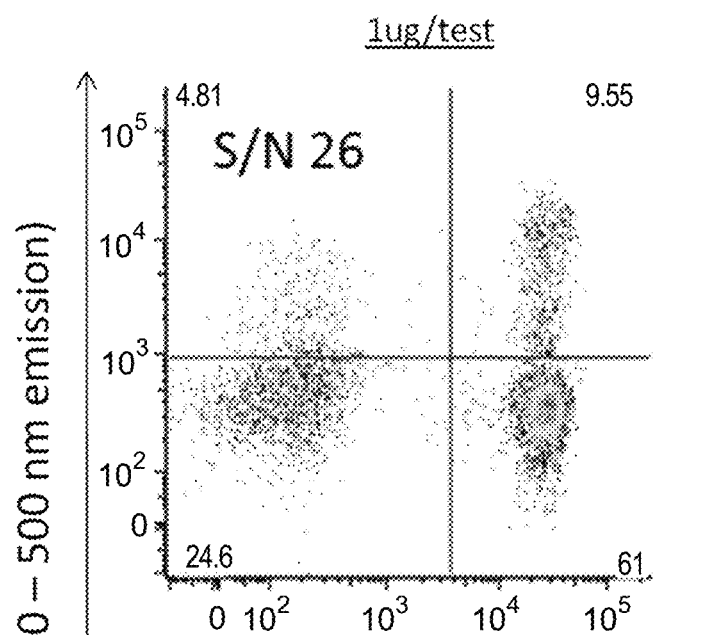
FIGS. 17A-B illustrate intracellular flow cytometric analysis of anti-human IFNγ clone 4S.B3 conjugated with compound P118-1 at 405 nm excitation; 400-500 nm emission with 1 μg/test (A); or 0.5 μg/test (B).
Figure 17B:
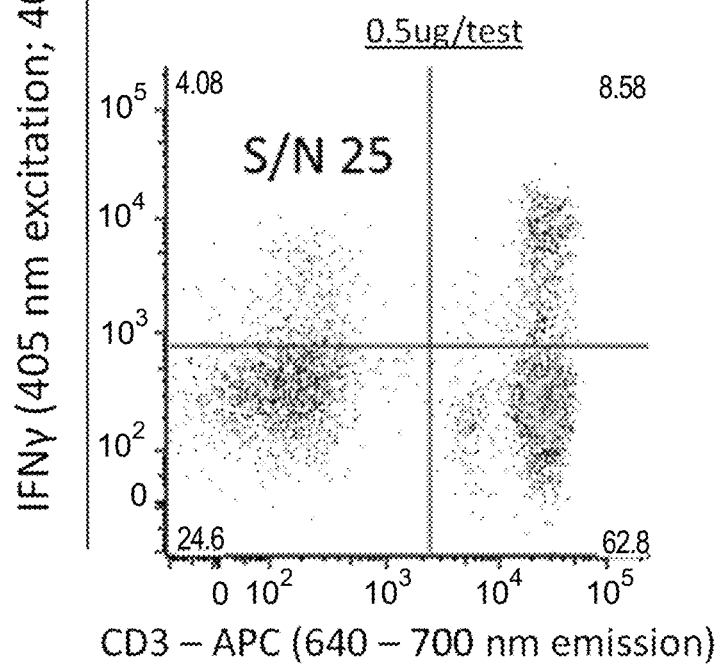

Intracellular flow cytometric analysis of anti-human IFNγ clone 4S.B3 conjugated with compound P118-1. Conjugated antibody was used to stain intracellular IFNγ in activated human peripheral blood mononuclear cell (PBMC) samples. Samples were also surface stained with allophycocyanin (APC)-conjugated anti-CD3 antibody to simultaneously identify T cells. P118-1-conjugated anti-IFNγ antibody was used at 1.0 ug/test and 0.5 ug/test. Samples were analyzed on a BD LSR IIB flow cytometer using the indicated excitation laser sources and emission collection parameters shown in FIG. 17A and FIG. 17B. Data is plotted as IFNγ on the ordinate and CD3 on the abscissa. The results show that a third and distinct fluorophore form of the invention can be used in an intracellular staining protocol, and in combination with a surface staining antibody conjugated with a different fluorophore to identify IFNγ producing CD3+ T cells.

Example 31

Figure 18:
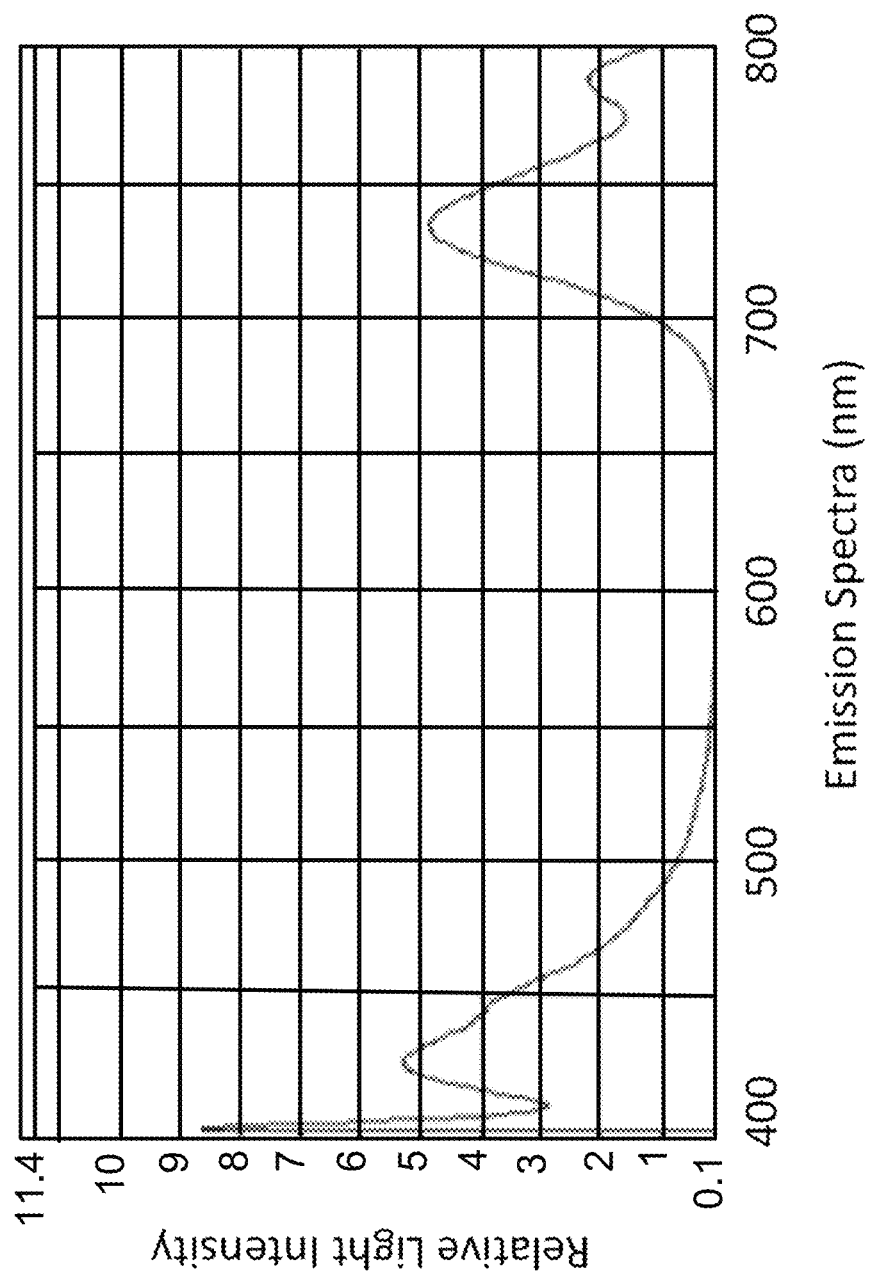
FIG. 18 illustrates emission spectra of tandem dye P114-700 conjugated to UCHT1 antibody.

FIG. 18 is a scanning emission spectrum of tandem dye P114-700 conjugated to UCHT1 antibody. The P114 fluorophore form of the invention was conjugated with the small molecule Alexa Fluor 700, serving as an acceptor dye, to create the "tandem" fluorophore construct P114-700. Such a construct may serve to transfer excitation light energy via the emissions of the P114 dye to the Alexa Fluor 700 dye when the P114 is excited at its optimal excitation wavelength (385 nm). In such a "tandem" double fluorophore construct the conjugated Alexa Fluor 700 dye is expected to yield long wavelength emissions (>700 nm) when the complex is excited with light (385 nm) well below the optimal excitation wavelengths (695 nm) of the Alexa Fluor 700. These results show that the P114-700 construct, when conjugated to a monoclonal antibody, provides substantial emissions at wavelengths greater than 700 nm.

Example 32

Figure 19A:
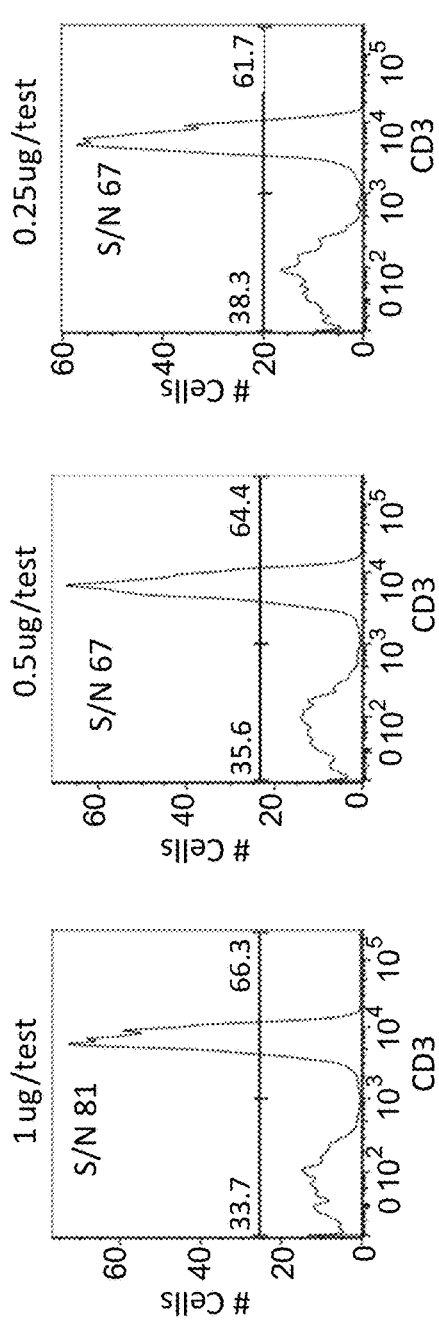
FIGS. 19A-B illustrate flow cytometric analysis of anti-human CD3 clone UCHT1 conjugated with compound P114-700 tandem fluorophore at 405 nm excitation; 685-760 nm emission (A); or 405 nm excitation; 750-840 nm emission (B).
Figure 19B:
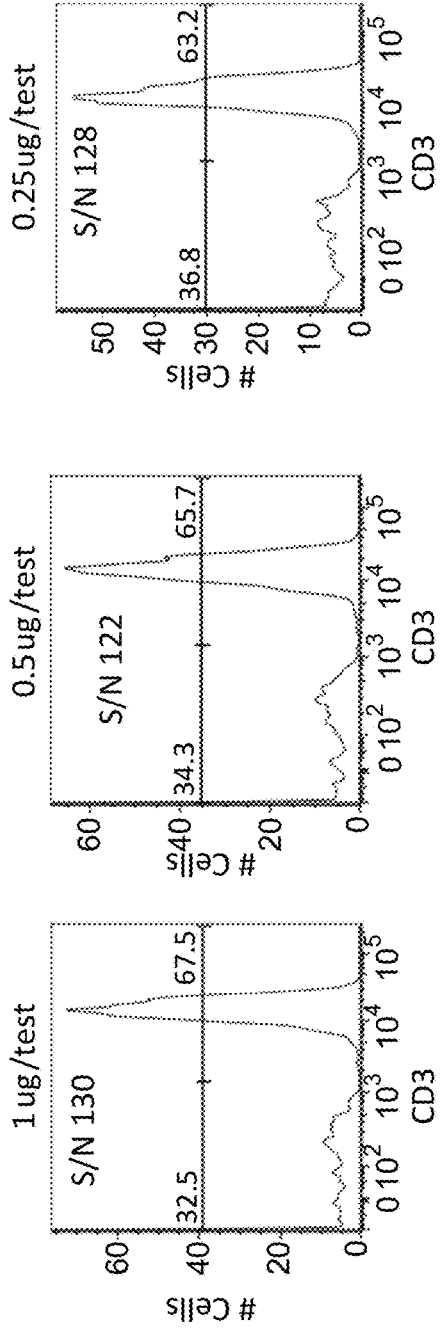

Flow cytometric analysis of anti-human CD3 clone UCHT1 conjugated with compound P114-700 tandem fluorophore. P114-700 tandem fluorophore-conjugated antibody was used to surface stain Lysed Washed Human Whole Blood (LWB) samples. Three different amounts of conjugated anti-CD3 were tested (1 ug/test, 0.5 ug/test, and 0.25 ug/test). Samples were analyzed on a BD LSR IIB flow cytometer using the indicated excitation laser sources and emission collection parameters shown in FIG. 19A and FIG. 19B. The results show that the P114-700 tandem fluorophore can be used to successfully identify the CD3+ cells present in a complex heterogeneous mixture of cells such as the LWB preparation.

Example 33

Figure 20A:
FIGS. 20A-B illustrates imaging results of anti-human CD3 clone UCHT1 conjugated with compound P118-1 used to stain frozen human tonsil tissue. Human tonsil tissue was frozen, microsectioned and then directly stained with P-118-1-conjugated UCHT1 antibody to identify CD3+ cells in the tonsil section by immunofluorescent imaging (FIG. 20A). For comparison, another microsection of the frozen tonsil was stained with BV421-conjugated UCHT1 (FIG. 20B).
Figure 20B:
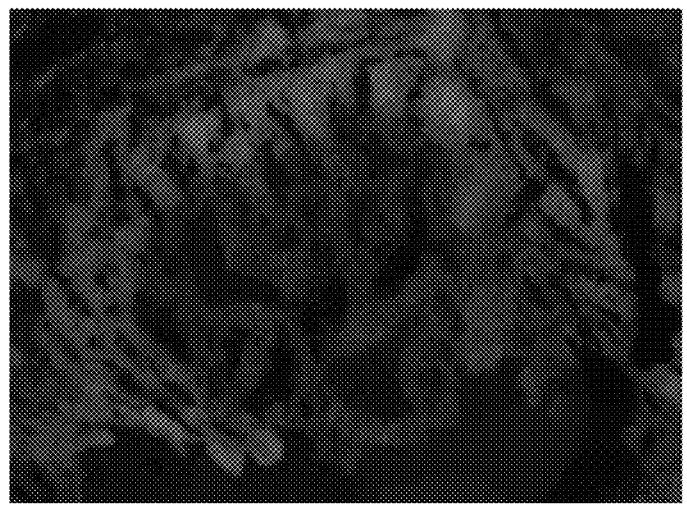

Imaging results of anti-human CD3 clone UCHT1 conjugated with compound P118-1 used to stain frozen human tonsil tissue. Human tonsil tissue was frozen, microsectioned and then directly stained with P118-1-conjugated UCHT1 antibody to identify CD3+ cells in the tonsil section by immunofluorescent imaging (FIG. 20A). For comparison, another microsection of the frozen tonsil was stained with BV421-conjugated UCHT1 (FIG. 20B). The results show that P118-1-conjugated antibody can be used in an immunofluorescent imaging protocol to identify and localize antigen bearing cells within tissues.

All patents, patent applications, and publications mentioned in the specification are indicative of the levels of those of ordinary skill in the art to which the invention pertains. All patents, patent applications, and publications are herein incorporated by reference in their entirety for all purposes and to the same extent as if each individual publication was specifically and individually indicated to be incorporated by reference in its entirety for any and all purposes.

What is claimed is:
1. A macromer of formula I:

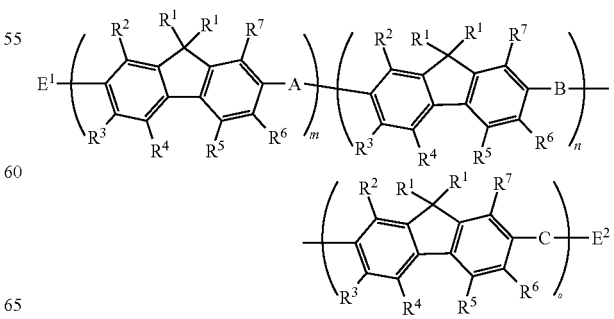

wherein adjacent $R^1$ groups on the same carbon atom form an optionally substituted 4-, 5-, or 6-membered ring selected from the group consisting of an optionally substituted $C_4$-$C_6$ cycloalkyl group and an optionally substituted $C_4$-$C_6$ heterocyclyl group, or alternatively, when at least one of $R^2$, $R^3$, $R^4$, $R^5$, $R^6$, or $R^7$ is other than hydrogen on a given monomer, each $R^1$ on the same monomer may be the same of different and is selected from the group consisting of hydrogen, an optionally substituted $C_1$-$C_{18}$ alkyl, an optionally substituted $C_1$-$C_{18}$ alkoxy, an optionally substituted $C_6$-$C_{18}$ aryl, an optionally substituted $C_4$-$C_{18}$ acyl, an optionally substituted $C_4$-$C_{18}$ acyloxy, a functional group for conjugation to a molecule or biomolecule, ethylene oxide oligomers and ethylene oxide polymer wherein the compound of Formula I contains at least one or more ethylene oxide oligomers or ethylene oxide polymer;

each $R^2$, $R^3$, $R^4$, $R^5$, $R^6$, and $R^7$ is independently selected from the group consisting of hydrogen, nitro, cyano, an optionally substituted amino, an optionally substituted $C_1$-$C_{18}$ alkyl, an optionally substituted $C_1$-$C_{18}$ alkoxy, optionally substituted $C_6$-$C_{18}$ aryl, optionally substituted $C_4$-$C_{18}$ acyl, optionally substituted $C_4$-$C_{18}$ acyloxy, a water solubilizing group, ethylene oxide oligomers, ethylene oxide polymer, and a functional group for conjugation to a biomolecule or dye, and wherein each of $R^2$, $R^3$, $R^4$, $R^5$, $R^6$, and $R^7$ may be the same or different within o, n and m;

m is a value selected from the group consisting of 1-200;
n is a value selected from the group consisting of 1-200;
o is a value selected from the group consisting of 0-10,000,
wherein the monomers within m, n, and o may be the same or different;

each of A, B, and C can be present or absent and can each be the same or different, and each is selected from the group consisting of an aromatic group or heteroaromatic group, which group completes a n-conjugated backbone and is a divalent substituent member selected from the group consisting of benzene, naphthalene, anthracene, benzodiathiazolyl, fluorene, indenofluorene, thiophene, thienothiophene, dithienothiophene, 3,4-ethylenedioxythiophene, furan, pyridine, pyrrole, fused pyrrole, tetrahydropyrene and oxadiazole, wherein each of the foregoing is optionally substituted with a ethylene oxide oligomers or ethylene oxide polymer; and $E^1$ and $E^2$ are each independently a member selected from the group consisting of hydrogen, halogen, alkynyl, optionally substituted aryl, optionally substituted heteroaryl, halo, substituted aryl, boronic acid substituted aryl, boronic ester substituted aryl, boronic ester, boronic acid, optionally substituted fluorene and aryl or heteroaryl substituted with one or more pendant chains terminated with: i) a functional group selected from amine, carbamate, carboxylic acid, carboxylate, maleimide, activated esters, N-hydroxysuccinimidyl, hydrazines, hydrazids, hydrazones, azide, alkyne, aldehydes, thiols, and protected groups thereof for conjugation to a molecule or biomolecule; or ii) a conjugated organic dye or biomolecule, wherein the molecular weight ($M_n$) of the macromer is about 5000 to about 100,000.

2. The macromer of claim 1, wherein the macromer has a molecular weight which is a member selected from the group consisting of about 5 kDa, about 6 kDa, about 7 kDa, about 8 kDa, about 9 kDa, about 10 kDa, about 11 kDa, about 12 kDa, about 13 kDa, about 14 kDa, about 15 kDa, about 16 kDa, about 17 kDa, about 18 kDa, about 19 kDa, about 20 kDa, about 21 kDa, about 22 kDa, about 23 kDa, about 24 kDa, about 25 kDa, about 26 kDa, about 27 kDa, about 28 kDa, about 29 kDa, about 30 kDa, about 31 kDa, about 32 kDa, about 33 kDa, about 34 kDa, about 35 kDa, about 36 kDa, about 37 kDa, about 38 kDa, about 39 kDa, about 40 kDa, about 41 kDa, about 42 kDa, about 43 kDa, about 44 kDa, about 45 kDa, about 46 kDa, about 47 kDa, about 48 kDa, about 49 kDa, about 50 kDa, about 51 kDa, about 52 kDa, about 53 kDa, about 54 kDa, about 55 kDa, about 56 kDa, about 57 kDa, about 58 kDa, about 59 kDa, about 60 kDa, and about 70 kDa.

3. The macromer of claim 1, wherein $E^1$ and/or $E^2$ is conjugated to an organic dye.

4. The macromer of claim 1, wherein the macromer has an emission wavelength of about 300 nm to about 500 nm.

5. The macromer of claim 1, wherein each of $R^2$, $R^3$, $R^4$, $R^5$, $R^6$, and $R^7$ is independently selected from the group consisting of hydrogen, a nitro, a cyano, and an optionally substituted amino.

6. The macromer of claim 1, wherein each of A, B, and C, is present and, is a divalent substituent member selected from the group consisting of benzene, naphthalene, anthracene, benzodiathiazolyl, fluorene, indenofluorene, thiophene, thienothiophene, dithienothiophene, 3,4-ethylenedioxythiophene, furan, pyridine, pyrrole, fused pyrrole, tetrahydropyrene and oxadiazole, wherein each of the foregoing is optionally substituted with a ethylene oxide oligomers or ethylene oxide polymer.

7. The macromer of claim 1, wherein two adjacent $R^1$ groups on the same carbon form an optionally substituted 4-, 5-, or 6-membered ring selected from the group consisting of optionally substituted $C_4$-$C_6$ cycloalkyl group and an optionally substituted $C_4$-$C_6$ heterocyclyl group.

8. The macromer of claim 1, wherein at least one of $R^2$, $R^3$, $R^4$, $R^5$, $R^6$, and $R^7$ is a functional group for conjugation which is a member selected from the group of an amine, a carbamate, a carboxylic acid, a carboxylate, a maleimide, an activated ester, N-hydroxysuccinimidyl, a hydrazine, a hydrazid, a hydrazone, an azide, an alkyne, an aldehyde, a thiol, and protected groups thereof for conjugation to a molecule or biomolecule.

9. A method for detecting a target biomolecule in a sample, said method comprising:
providing a sample that is suspected of containing a target analyte;
providing a macromer according to claim 1 conjugated to a capture molecule, wherein the capture molecule is capable of interacting with the target analyte;
contacting the sample with the capture molecule and the conjugated macromer under conditions in which the capture molecule can bind to the target analyte, if present; and
applying a light source to the sample that excites the conjugated macromer; and detecting whether light is emitted from the conjugated macromer.

10. The method of claim 9, wherein the method is performed in vitro.

11. The method of claim 9, wherein the sample comprises a fixed cell.

12. The method of claim 9, wherein the sample comprises a permeabilized cell.

* * * * *